United States Patent
Hester, Jr.

(10) Patent No.: US 7,049,443 B2
(45) Date of Patent: May 23, 2006

(54) AMIDE-CONTAINING COMPOUND HAVING IMPROVED SOLUBILITY AND METHOD OF IMPROVING THE SOLUBILITY OF AN AMIDE-CONTAINING COMPOUND

(75) Inventor: Jackson B. Hester, Jr., Galesburg, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 591 days.

(21) Appl. No.: 10/194,914

(22) Filed: Jul. 12, 2002

(65) Prior Publication Data

US 2004/0014967 A1 Jan. 22, 2004

Related U.S. Application Data

(60) Provisional application No. 60/304,808, filed on Jul. 12, 2001.

(51) Int. Cl.
*C07D 263/04* (2006.01)

(52) U.S. Cl. .................................. 548/229; 514/376
(58) Field of Classification Search ................. 548/229; 514/376

See application file for complete search history.

(56) References Cited

U.S. PATENT DOCUMENTS 6,313,307 B1 * 11/2001 Ennis et al. ................. 548/229

\* cited by examiner

*Primary Examiner*—Shailendra Kumar
(74) *Attorney, Agent, or Firm*—Lucy X. Yang; Terryence F. Chapman

(57) ABSTRACT

The present invention is directed to novel amide-containing compounds which have an improved solubility and a method of improving the solubility of amide-containing compounds. The amide-containing compounds include oxazolidinone compounds and the bioavailability of these oxazolidinone compounds is improved by improving the solubility thereof.

14 Claims, No Drawings

AMIDE-CONTAINING COMPOUND HAVING IMPROVED SOLUBILITY AND METHOD OF IMPROVING THE SOLUBILITY OF AN AMIDE-CONTAINING COMPOUND

This application claims benefit of 60/304,808, filed Jul. 12, 2001.

FIELD OF THE INVENTION

The present invention is directed to amide-containing compounds having an improved water solubility and a method for improving the water-solubility of amide-containing compounds in general and, specifically, to oxazolidinone compounds having improved water solubility and a method of improving the water-solubility of oxazolidinone compounds.

BACKGROUND OF THE INVENTION

There are many compounds that contain amide groups which have desirable pharmacological activity. For example, oxazolidinone derivatives containing an amide group are known to exhibit a variety of biological activities.

Oxazolidinone derivatives have been shown to be inhibitors of monoamine oxidase-B, an enzyme implicated in Parkinson's disease. Ding et al., *J. Med. Chem.* 36:3606–3610 (1993).

Scientists have reported that certain oxazolidinone derivatives exhibit beneficial antibacterial effects. For instance, N-[3-[3-fluoro-4-(morpholin-4-yl)phenyl]2-oxooxazolidin-5(s)-ylmethyl] acetamide (below) has been reported to be useful for the treatment of bacterial infections. Lizondo et al., *Drugs of the Future,* 21:1116–1123 (1996).

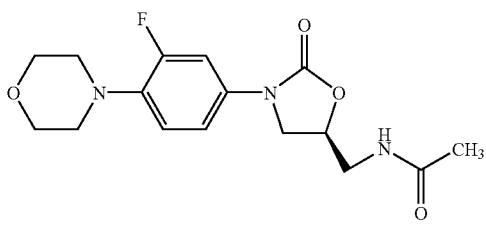

A ten step synthesis of oxazolidinone antibiotics has been described in U.S. Pat. No. 5,547,950. A four step synthesis of the antibacterial compound U-100592 also has been reported. Schauss et al., *Tetrahedron Letters,* 37:7937–7940 (1996). A five step preparation of enantiomerically pure cis- and trans-N-(propionyl)hexahydrobenzoxazolidin-2-ones further was reported in De Parrodi et al., *Tetrahedron: Asymmetry,* 8:1075–1082 (1997).

The synthesis of the oxazolidinone antibacterial agent shown below has been reported. Wang et al., *Tetrahedron,* 45:1323–1326 (1989). This oxazolidinone was made using a process that included the reaction of an aniline with glycidol to provide an amino alcohol, and the diethylcarbonate mediated cyclization of the amino alcohol to afford an oxazolidinone.

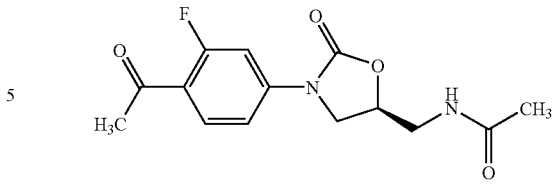

The synthesis of oxazolidinone antibacterial agents, including the compound shown below has been reported. U.S. Pat. No. 4,705,799. The process used to make the compound shown below included a metal mediated reduction of a sulfonyl chloride to provide a sulfide.

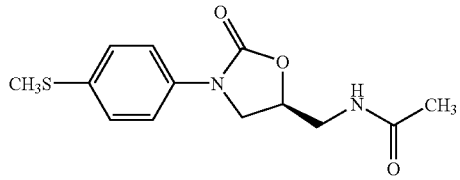

The synthesis of oxazolidinone antibacterial agents, including the pyridyl compound shown below has been reported. U.S. Pat. No. 4,948,801. The process used included an organometallic mediated coupling of an organotin compound and an aryl iodide.

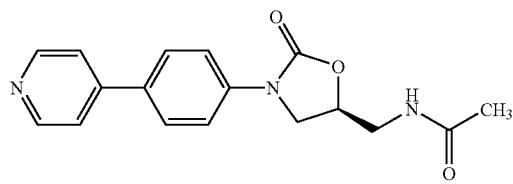

U.S. Pat. No. 5,652,238 discloses carboxylic and phosphate esters of substituted-hydroxyacetyl piperazine phenyl oxazolidinones.

U.S. Pat. No. 5,688,792 discloses substituted oxazine and thiazine oxazolidinone useful as antibacticals.

PCT International Publication WO 98/54161 discloses oxazolidinone antibacterial agents having a thiocarbonyl functionality.

U.S. Pat. No. 5,968,962 and PCT International Publication WO 99/29688 discloses phenyloxazolidinones having a C—C bond to 4–8 membered heterocyclic rings.

U.S. Pat. No. 5,952,324 discloses bicyclic oxazine and thiazine oxazolidinone useful as antibacticals.

PCT publications, WO 99/64416, WO 99/64417, and WO 00/21960 disclose oxazolidinone derivatives useful as antibacterial agents.

PCT Publication, WO 00/10566 discloses isoxazolinones useful as antibacterial agents.

U.S. Pat. No. 5,880,118 discloses substituted oxazine and thiazine oxazolidinone antimocrobials.

U.S. Pat. No. 6,968,962 discloses phenyloxazolidinones having a C—C bond to 4–8 membered heterocyclic rings.

U.S. Pat. No. 5,981,528 discloses antibiotic oxazolidinone derivatives.

U.S. patent application Ser. No. 60/236,595 discloses N-({(5S)-3-[4-(1,1-dioxido-4-thiomorpholinyl)-3,5-difluorophenyl]-2-oxo-1,3-oxazolidin-5-yl}methyl) acetamide.

PCT publications, WO 99/64416, WO 99/64417, and WO 00/21960 disclose isoxazolinone derivatives useful as antibacterial agents.

PCT publication, WO 00/10566 discloses isoxazolinones useful as antibacterial agents.

U.S. Pat. No. 5,164,510 discloses 5'-indolinyloxazolidin-2-ones of formula XI

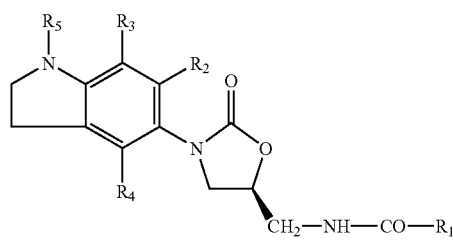

XI which are useful as antibacterial agents.

U.S. Pat. Nos. 5,036,092; 5,036,093; 5,039,690; 5,032,605 and 4,965,268 disclose aminomethyl oxazolidinyl aza cycloalkylbenzene derivatives useful as antibacterial agents.

U.S. Pat. Nos. 5,792,765 and 5,684,023 disclose substituted isoxazolinones useful as antibacterial agents.

International Publication No. WO 97/09328 discloses phenyloxazolidinones having a C—C bond to 4–8 membered heterocyclic rings useful as antimicrobial agents.

PCT International Publication WO 93/23384 discloses oxazolidinones containing a substituted diazine moiety and their use as antimicrobials.

PCT International Publication WO 95/07271 discloses substituted oxazine and thiazine oxazolidinones and their use as antimicrobials.

However, even though some amide-containing compounds have been shown to be extremely effective in the treatment of certain physiological disorders, some of these compounds have a low bioavailability due to their low water solubility and/or low permeability through biological barriers, such as the blood brain barrier and the intestinal barrier.

In order to increase the bioavailability of certain amines, peptides and peptidomimetics, prodrugs of these compounds, have been proposed. Zheng et al, *Tetrahedron Letters*, 55:4237–4254 (1999), Wang et al, *Journal of Controlled Release*, 65:245–251 (2000) and Wang et al, *Bioorganic & Medicinal Chemistry*, 6:417–426 (1998). These prodrugs derivatize certain polar functional groups transiently and bioreversably to mask undesirable physical chemical characteristics of the groups without permanently altering the pharmacological properties of the molecules and have been used very successfully in cases where the prodrug derivatization involves converting a carboxyl or a hydroxyl functional group into an ester which can be readily hydrolyzed in vivo either chemically or enzymatically. However, this strategy has not been successfully used in the case of an amide group due to the chemical stability thereof.

As such, there is a need for amide-containing compounds having an improved water-solubility and bioavailability and for methods for synthesizing these compounds.

SUMMARY OF THE INVENTION

The objects of the present invention are met by providing an oxazolidinone derivative of Formula (I)

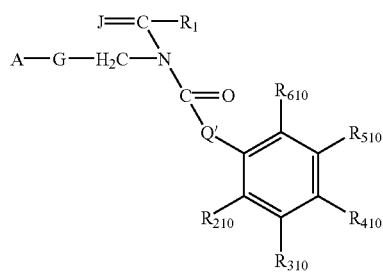

(I)

wherein J is O or S;

Q' is a)

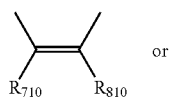

or b)

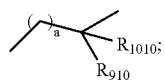

$R_{210}$ is a)

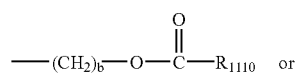

or b)

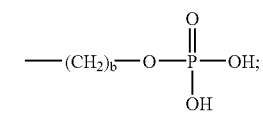

$R_{310}$, $R_{410}$ and $R_{510}$ each independently are
  a) H,
  b) $C_{1-4}$ alkyl,
  c) halogen,
  d) $C_{1-4}$ alkoxy,
  e) hydroxy,
  f) $(CH_2)_cOP(O)(OH)_2$,
  g) $C_{1-4}$ acyloxy, or
  h) $C_{1-4}$ alkyl substituted by halogen, hydroxy, acyloxy, $NR_{1210}R_{1310}$, or alkoxy;

$R_{610}$, $R_{710}$ and $R_{810}$ each independently are
  a) H,
  b) $CH_3$, or
  c) $C_2H_5$;

$R_{910}$ and $R_{1010}$ each independently are
  a) H,
  b) $CH_3$,
  c) $C_2H_5$, or
  d) combine to form a $C_{3-5}$ cycloalkyl;

$R_{1110}$ is H or $C_{1-6}$ alkyl;

$R_{1210}$ and $R_{1310}$ each independently are
  a) H, b) $C_{1-4}$ alkyl, or
c) combine to form a heterocyclic ring;
wherein a is 0 or 1, b is 0 or 1, and c is 0 or 1, with the proviso that when Q' is

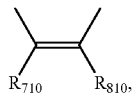

b is 0 and a+b is 0 or 1;
$R_1$ is
  a) $C_{1-4}$ alkyl,
  b) $C_{2-4}$ alkenyl,
  c) $OC_{1-4}$ alkyl,
  d) $C_{3-6}$ cycloalkyl,
  e) $C_{1-4}$ alkyl substituted with 1–3F, 1–2Cl, CN, —$COOC_{1-4}$ alkyl or a $C_{3-6}$ cycloalkyl; or
  f) H
A is

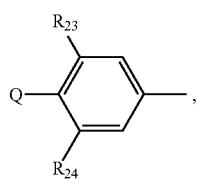

$R_4$ is
  a) $C_{1-4}$ alkyl optionally substituted with one or more halos, OH, CN, $NR_{10}R_{11}$, or —$CO_2R_{13}$,
  b) $C_{2-4}$ alkenyl,
  c) —$NR_{16}R_{18}$,
  d) —$N_3$,
  e) —NHC(=O)$R_7$,
  f) —$NR_{20}$C(=O)$R_7$,
  g) —$N(R_1)_2$,
  h) —$NR_{16}R_{19}$, or
  i) —$NR_{19}R_{20}$,
$R_5$ and $R_6$ at each occurrence are the same or different and are
  a) $C_{1-2}$ alkyl, or
  b) $R_5$ and $R_6$ taken together are —$(CH_2)_k$—;
$R_7$ is $C_{1-4}$ alkyl optionally substituted with one or more halos;
$R_{10}$ and $R_{11}$ at each occurrence are the same or different and are
  a) H,
  b) $C_{1-4}$ alkyl, or
  c) $C_{3-8}$ cycloalkyl;
$R_{13}$ is
  a) H, or
  b) $C_{1-4}$ alkyl;
$R_{14}$ and $R_{15}$ at each occurrence are the same or different and are
  a) $C_{1-4}$ alkyl, or
  b) $R_{14}$ and $R_{15}$ taken together are —(CH)$_i$—;
$R_{16}$ is
  a) H,
  b) $C_{1-4}$ alkyl, or
  c) $C_{3-8}$ cycloalkyl;

$R_{17}$ is
  a) $C_{1-4}$ alkyl, or
  b) $C_{3-8}$ cycloalkyl;
$R_{18}$ is
  a) H,
  b) $C_{1-4}$ alkyl,
  c) $C_{2-4}$ alkenyl,
  d) $C_{3-4}$ cycloalkyl,
  e) —$OR_{13}$ or
  f) —$NR_{21}R_{22}$;
$R_{19}$ is
  a) Cl,
  b) Br, or
  c) I;
$R_{20}$ is a physiologically acceptable cation;
$R_{21}$ and $R_{22}$ at each occurrence are the same or different and are
  a) H,
  b) $C_{1-4}$ alkyl, or
  c) —$NR_{91}R_{22}$ taken together are —$(CH_2)_m$—;
wherein $R_{23}$ and $R_{24}$ at each occurrence are the same or different and are
  a) H,
  b) F,
  c) Cl,
  d) $C_{1-2}$ alkyl,
  e) CN
  f) OH,
  g) $C_{1-2}$ alkoxy,
  h) nitro, or
  i) amino;
Q is a)

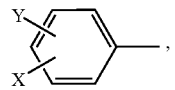

b)

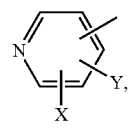

c)

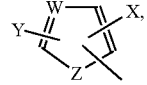

d)

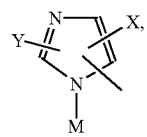

e)

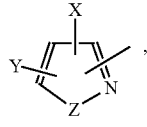

-continued
f) 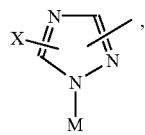
g) 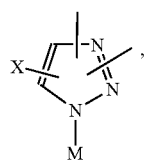
h) 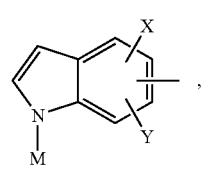
i) 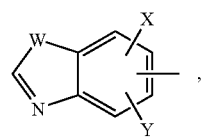
j) 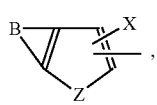
k) 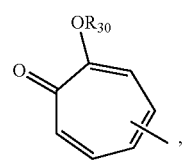
l) 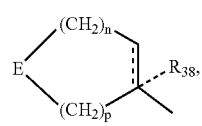
m) a diazinyl group optionally substituted with X and Y,
n) a triazinyl group optionally substituted with X and Y,
o) a quinolinyl group optionally substituted with X and Y,
p) a quinoxalinyl group optionally substituted with X and Y,
q) a naphthyridinyl group optionally substituted with X and Y,
r) 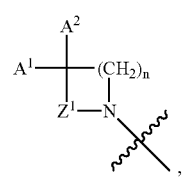
-continued
s) 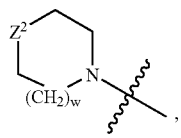
t) 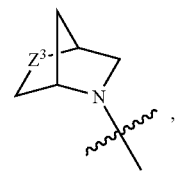
u) 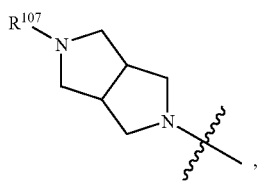
v) 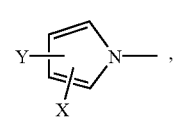
w) 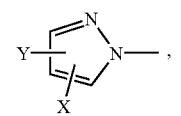
x) 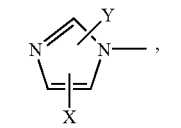
y) 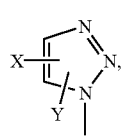
z) 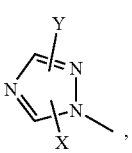
aa) 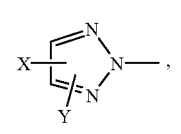

-continued bb)
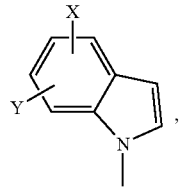

cc)
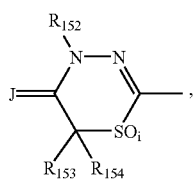

dd)
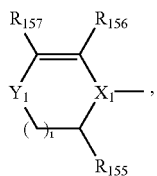

ee)
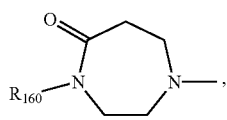

ff)
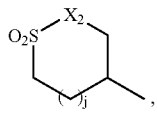

gg)
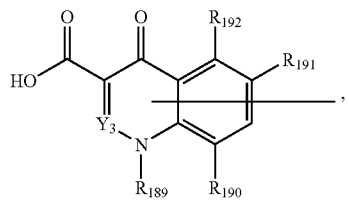

hh)
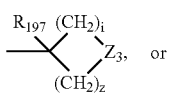

ii)
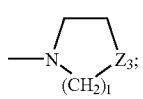

Q and $R_{24}$ taken together are

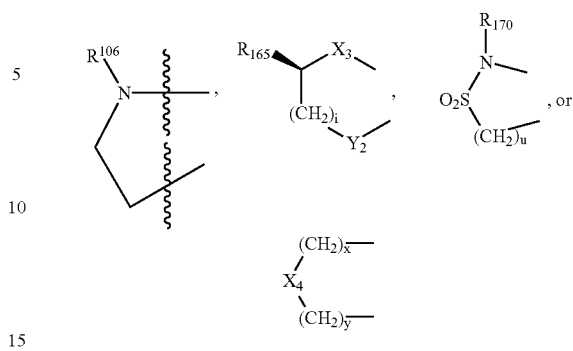

wherein $Z^1$ is
  a) —CH$_2$—,
  b) —CH($R^{104}$)—CH$_2$—,
  c) —C(O)—, or
  d) —CH$_2$CH$_2$CH$_2$—;
wherein $Z^2$ is
  a) —O$_2$S—,
  b) —O—,
  c) —N($R^{107}$)—,
  d) —OS—,
  e) —S—, or
  f) S(O)(NR$_{190}$);
wherein $Z^3$ is
  a) —O$_2$S—,
  b) —O—,
  c) —OS—,
  d) —S—, or
  e) S(O)(NR$_{190}$)
wherein $A^1$ is
  a) H—, or
  b) CH$_3$;
wherein $A^2$ is
  a) H—,
  b) HO—,
  c) CH$_3$—,
  d) CH$_3$O—,
  e) $R^{102}$O—CH$_2$—C(O)—NH—,
  f) $R^{103}$O—C(O)—NH—,
  g) (C$_1$–C$_2$)alkyl-O—C(O)—,
  h) HO—CH$_2$—,
  i) CH$_3$O—NH—,
  j) (C$_1$–C$_3$)alkyl-O$_2$C—,
  k) CH$_3$—C(O)—,
  l) CH$_3$—C(O)—CH$_2$—,
  m)
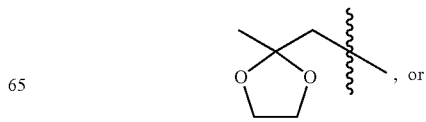

n) 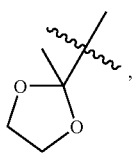, $A^1$ and $A^2$ taken together are:

a) 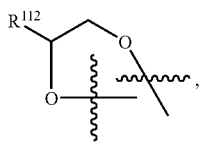, b) 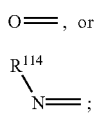

c) $O=$, or

;

wherein $R^{102}$ is
  a) H—,
  b) $CH_3$—,
  c) phenyl-$CH_2$—, or
  d) $CH_3C(O)$—;
wherein $R^{103}$ is
  a) $(C_1–C_3)$alkyl-, or
  b) phenyl-;
wherein $R^{104}$ is
  a) H—, or
  b) HO—;
wherein $R^{106}$ is
  a) $CH_3$—C(O)—,
  b) H—C(O)—,
  c) $Cl_2CH$—C(O)—,
  d) $HOCH_2$—C(O)—,
  e) $CH_3SO_2$—, f) 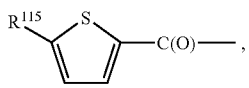, g) F2CHC(O)—, h) 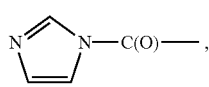, i) $H_3C$—C(O)—O—$CH_2$—C(O)—,
j) H—C(O)—O—$CH_2$—C(O)—;

k) 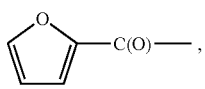, l) HC≡C—$CH_2$O—$CH_2$—C(O)—, or
m) phenyl-$CH_2$—O—$CH_2$—C(O)—;

wherein $R^{107}$ is
  a) $R^{102}$—C($R^{110}$)($R^{111}$)—C(O)—,
  b) $R^{103}$O—C(O)—
  c) $R^{108}$—C(O)—, d) 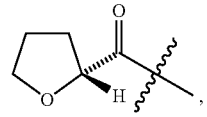, e) 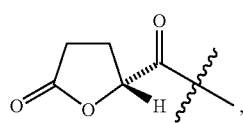, f) $H_3C$—C(O)—$(CH_2)_2$—C(O)—,
g) $R^{109}$—$SO_2$—, h) 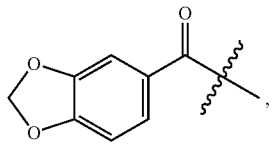, i) HO—$CH_2$—C(O)—,
j) $R^{116}$—$(CH_2)_2$—,
k) $R^{113}$—C(O)—O—$CH_2$—C(O)—,
l) $(CH_3)_2N$—$CH_2$—C(O)—NH—,
m) NC—$CH_2$—,
n) $F_2$—CH—$CH_2$—, or
o) $R^{150}R^{151}NSO_2$
p) $C(O)CR_{180}R_{180}R_{181}OR_{182}$,
q) $C(O)CH_2S(O)_tCH_3$,
r) $C(O)CH_2S(O)(NR_{183})CH_3$,
s) $C(S)R_{184}$,
t) $C(O)CH_2OR_{185}$,
u) $C(O)(CH_2)C(O)CH_3$,
v) $C(O)(CH_2OH)_2CH_3$,
w) $C(O)CH_2CH_2OR_{189}$, or
x) —CN;
wherein $R^{108}$ is
  a) H—,
  b) $(C_1–C_4)$alkyl,
  c) aryl —$(CH_2)_p$,
  d) $ClH_2C$—,
  e) $Cl_2HC$—,
  f) $FH_2C$—,
  g) $F_2HC$—, h) $(C_3–C_6)$cycloalkyl, or
i) $CNCH_2—$.
wherein $R^{109}$ is
a) alkyl$C_1–C_4$,
b) $—CH_2Cl$
c) $—CH_2CH=CH_2$,
d) aryl, or
e) $—CH_2CN$;
wherein $R^{110}$ and $R^{111}$ are independently
a) $H—$,
b) $CH_3—$; or
wherein $R^{112}$ is
a) $H—$,
b) $CH_3O—CH_2O—CH_2—$, or
c) $HOCH_2—$;
wherein $R^{113}$ is
a) $CH_3—$,
b) $HOCH_2—$,
c) $(CH_3)_2$N-phenyl, or
d) $(CH_3)_2N—CH_2—$;
wherein $R^{114}$ is
a) $HO—$,
b) $CH_3O—$,
c) $H_2N—$,
d) $CH_3O—C(O)—O—$,
e) $CH_3—C(O)—O—CH_2—C(O)O—$,
f) phenyl-$CH_2—O—CH_2—C(O)—O—$,
g) $HO—(CH_2)_2—O—$,
h) $CH_3O—CH_2—O—(CH_2)_2—O—$, or
i) $CH_3O—CH_2—O—$;
wherein $R^{115}$ is
a) $H—$, or
b) $Cl—$;
wherein $R^{116}$ is
a) $HO—$
b) $CH_3O—$, or
c) F;
wherein $R^{150}$ and $R^{151}$ are each H or alkyl $C_1–C_4$ or $R^{150}$ and $R^{151}$ taken together with the nitrogen atom to which each is attached form a monocyclic heterocyclic ring having from 3 to 6 carbon atoms;
$R_{152}$ is
a) H,
b) $C_{1-4}$alkyl,
c) $C_{1-4}$heteroalkyl,
d) $(CH_2)_tC(=O)OC_{1-4}$alkyl,
e) $(CH_2)_tC(=O)C_{1-4}$alkyl,
f) aryl, or
g) het$^1$;
$R_{153}$ and $R_{154}$ are independently
a) H,
b) F,
c) $C_{1-4}$alkyl,
d) $C_{3-6}$cycloalkyl,
e) $C_{1-4}$heteroalkyl,
f) aryl,
g) het$^1$,
h) $OC_{1-4}$alkyl,
i) $O(C=O)C_{1-4}$alkyl,
j) $(C=O)OC_{1-4}$alkyl; or
k) $R_{153}$ and $R_{154}$ taken together are $C_{3-6}$cycloalkyl;
$R_{155}$ is
a) H,
b) F,
c) $C_{1-4}$alkyl,
d) $OC_{1-4}$alkyl,
e) $SC_{1-4}$alkyl, or
f) $NHC_{1-4}$alkyl;
$R_{156}$ is
a) H,
b) $C_{1-4}$alkyl,
c) $OC_{1-4}$alkyl,
d) $SC_{1-4}$alkyl, or
e) $NHC_{1-4}$alkyl;
$R_{157}$ is
a) $—H$,
b) $—F$,
c) $—Cl$,
d) $—NH_2$,
e) $—OH$,
f) $—CN$,
g) $—C_{1-4}$alkyl,
h) $—OC_{1-4}$alkyl,
i) $—C_{1-4}$alkyl-W—$C_{1-4}$alkyl,
j) $—NHC_{1-4}$alkyl,
k) $—(CH_2)_tC_{3-6}$cycloalkyl,
l) $—C(=O)C_{1-4}$alkyl,
m) $—OC(=O)C_{1-4}$alkyl,
n) $—C(=O)OC_{1-4}$alkyl,
o) $—S(O)_tC_{1-4}$alkyl, or
p) $—C(=O)NHC_{1-4}$alkyl;
$R_{158}$ is
a) $—H$,
b) $—CH_3$,
c) $—F$, or
d) $—OH$;
$R_{159}$ is
a) $—H$,
b) $—C_{1-4}$alkyl,
c) $—C(=O)C_{1-4}$alkyl,
d) $—C(=O)NHC_{1-4}$alkyl,
e) $—OC(=O)C_{1-4}$alkyl,
f) $—C(=O)OC_{1-4}$alkyl, or
g) $—S(O)_tC_{1-4}$alkyl, or
h) $—C_{1-4}$alkyl-$W_1$—$C_{1-4}$alkyl;
$R_{160}$ is H, $C_{2-6}$ alkenyl, $C_{2-7}$alkynyl, $C_{1-6}$ alkyl substituted with one or two of the following:
a) F,
b) Cl,
c) $CF_3$,
d) $—OH$,
e) $C_{1-4}$alkoxy,
f) $—CH_2C(=O)C_{1-4}$alkyl,
g) $—OC(=O)N(R_{161})_2$,
h) $C_{1-4}$alkyl $S(O)_n$, (wherein n is 0, 1 or 2),
i) $—CN$,
j) carboxy, k) —$C_{1-4}$alkoxycarbonyl,
l) —C(=O)N($R_{161}$)$_2$,
m) —N($R_{161}$)SO$_2$C$_{1-4}$ alkyl,
n) —N($R_{161}$)C(=O)C$_{1-4}$ alkyl,
o) —N($R_{161}$)C(=O)N($R_4$)$_2$,
p) —N($R_{161}$)C(=O)C$_{1-4}$ alkoxy,
q) aryl, or
r) Het$_1$;

$R_{161}$ is
a) H, or
b) $C_{1-3}$ alkyl;

$R_{162}$ is
a) H,
b) $C_{1-8}$ alkyl, optionally substituted with one to three F, Cl, OH, CN, NH$_2$, OC(=O)C$_{1-4}$alkyl, or OC$_{1-4}$ alkyl,
c) $C_{3-8}$ alkene, or
d) C(=O)NR$_{163}$R$_{164}$;

$R_{163}$ and $R_{164}$ are independently
a) H, or
b) $C_{1-8}$ alkyl, optionally substituted with one to three F, Cl, OH, CN, or NH$_2$;

$R_{165}$ is $C_{1-4}$ alkyl, optionally substituted with 1–3 $R_{168}$;

$R_{166}$ is
a) $C_{1-8}$ alkyl, optionally substituted with 1–3 halo, CN, NO$_2$, OH, SH or NH$_2$;
b) —C(=O)R$_{167}$ or
c) —C(=S)NHC$_{1-4}$ alkyl;

$R_{167}$ is
a) H,
b) $C_{1-6}$ alkyl, optionally substituted with OH, C$_{1-4}$ alkoxy, NH$_2$, SH or halo, or
c) —CH$_2$OC(=O)C$_{1-4}$ alkyl;

$R_{168}$ is
j) halo,
k) —CN,
l) —OH,
m) —SH,
n) —NH$_2$,
o) —OR$_{169}$,
p) —NHR$_{169}$,
q) —N(R$_{169}$)$_2$, or
r) —S(=O)$_t$R$_{169}$;

$R_{169}$ is
g) $C_{1-6}$ alkyl,
h) —C(=O)C$_{1-4}$ alkyl,
i) —C(=O)O C$_{1-4}$ alkyl,
j) —C(=O)NH$_2$,
k) —C(=O)NH C$_{1-4}$ alkyl, or
l) —SO$_2$C$_{1-4}$ alkyl;

with the proviso that where j is 0, Y$_2$ is —CH$_2$—.

$R_{170}$ is
a) H,
b) $C_{1-12}$ alkyl, optionally substituted with phenyl or CN, or
c) $C_{2-12}$ alkyl substituted with OH, SH, NH$_2$, —OC$_{1-6}$ alkyl, —NHC$_{1-6}$ alkyl, —NHCOC$_{1-6}$ alkyl, —NHSO$_2$C$_{1-6}$ alkyl, —S(O)$_t$C$_{1-6}$ alkyl, or one to three halo;

$R_{172}$ is
a) H,
b) $C_{1-8}$ alkyl,
c) aryl,
d) het$_1$,
e) C(=W)R$_{174}$,
f) C(=O)OR$_{175}$, or
g) S(=O)$_t$R$_{176}$;

$R_{173}$ is
a) H, or
b) $C_{1-8}$ alkyl;

$R_{174}$ is
a) H,
b) aryl,
c) het$_1$,
d) NR$_{177}$R$_{178}$, or
e) $C_{1-8}$ alkyl;

$R_{175}$ is
a) $C_{1-8}$ alkyl,
b) aryl, or
c) het$_1$;

$R_{176}$ is
a) aryl,
b) het$_1$,
c) NR$_{177}$R$_{178}$, or
d) $C_{1-8}$ alkyl;

$R_{177}$ and $R_{178}$ are independently
a) H,
b) $C_{1-8}$ alkyl, or
c) aryl;

$R_{180}$ and $R_{181}$ taken together form $C_{3-5}$ cycloalkyl;
$R_{182}$ is H, CH$_3$ or C$_{1-4}$ alkanoyl;
$R_{183}$ is H, C$_{1-4}$ alkyl, C$_{1-4}$ alkanoyl, —C(=O)NH—C$_{1-4}$ alkyl or —CO$_2$C$_{1-4}$ alkyl;
$R_{184}$ is C$_{1-4}$ alkyl, CH$_2$OR$_{186}$, S—C$_{1-4}$ alkyl, OC$_{1-4}$ alkyl, or NR$_{187}$R$_{188}$;
$R_{185}$ is phenyl, —CO$_2$—(CH$_2$)$_2$—OCH$_3$, —P(=O)(OH)$_2$, —C(=O)—NR$_{187}$R$_{186}$, or —C(=O)—(CH$_2$)$_2$—CO$_2$H;
$R_{186}$ is H, phenyl, benzyl, CH$_3$ or C(=O)CH$_3$;
$R_{187}$ and $R_{188}$ are independently H or C$_{1-3}$ alkyl; or $R_{187}$ and $R_{188}$ taken together form a 5- or 6-membered saturated heterocycle, wherein said saturated heterocycle may further contain one or two additional hetero-atoms selected from a group consisting of O, S(O)$_n$ or NR$_{182}$;
$R_{189}$ is H, CH$_3$ or benzyl;

$R_{190}$ is
a) H,
b) $C_{1-4}$ alkyl,
c) C(=O)C$_{1-4}$ alkyl,
d) C(=O)OC$_{1-4}$ alkyl,
e) C(=O)NHR$_{191}$, or
f) C(=S)NHR$_{191}$;

$R_{191}$ is H, C$_{1-4}$ alkyl, or phenyl;
at each occurrence, alkyl in $R_{190}$ and $R_{191}$ is optionally substituted with one or more halo, CN, NO$_2$, phenyl, C$_{3-6}$ cycloalkyl, OR$_{192}$, C(=O)R$_{192}$, OC(=O)R$_{192}$, C(=O)OR$_{192}$, SC(=O)$_t$R$_{192}$, S(=O)$_t$NR$_{192}$R$_{192}$, NR$_{192}$R$_{192}$, NR$_{192}$SO$_2$R$_{192}$, NR$_{192}$SO$_2$R$_{192}$R$_{192}$, NR$_{192}$C(=O)R$_{192}$, C(=O)NR$_{192}$R$_{192}$, NR$_{192}$R$_{192}$, oxo or oxime;
$R_{192}$ is H, C$_{1-4}$ alkyl, or phenyl;
at each occurrence, phenyl in $R_{191}$ and $R_{192}$ is optionally substituted with one or more halo, CN, NO$_2$, phenyl, $C_{3-6}$ cycloalkyl, $OR_{192}$, $C(=O)R_{192}$, $OC(=O)R_{192}$, $C(=O)OR_{192}$, $S(=O)R_{196}$, $S(=O)_iNR_{192}R_{192}$, $NR_{192}SO_2R_{192}$, $NR_{192}SO_2NR_{192}R_{192}$, $NR_{192}C(=O)R_{192}$, $C(=O)NR_{192}R_{192}$, or $NR_{192}R_{192}$;

$R_{193}$ is selected from the group consisting of null, H, $C_1$–$C_4$alkyl, $C_3$–$C_5$cycloalkyl, $C_1$–$C_4$haloalkyl, and halophenyl;

$R_{194}$ is selected from the group consisting of H, alkyl, $C_1$–$C_2$alkoxy, halo, and haloalkoxy, or $R_{193}$ and $R_{194}$ can be taken together to form a 5- or 6-membered, optionally substituted, heteroalkyl or heteroaryl ring;

$R_{195}$ is H or F;

$R_{196}$ is selected from the group consisting of H, methyl, amino, and F;

$R_{197}$ is H, $CH_3$, or F;

B is an unsaturated 4-atom linker having one nitrogen and three carbons;

M is
  a) H,
  b) $C_{1-8}$ alkyl,
  c) $C_{3-8}$ cycloalkyl,
  d) —$(CH_2)_mOR_{13}$, or
  e) —$(CH_2)_n$—$NR_{21}R_{22}$;

Z is
  a) O,
  b) S, or
  c) NM;

W is
  a) CH,
  b) N, or
  c) S or O when Z is NM;

Y is
  a) H,
  b) F,
  c) Cl,
  d) Br,
  e) $C_{1-3}$ alkyl, or
  f) $NO_2$;

X is
  a) H,
  b) —CN,
  c) $OR_{27}$,
  d) halo,
  e) $NO_2$,
  f) tetrazoyl,
  g) —SH,
  h) —$S(=O)_iR_4$,
  i) —$S(=O)_2$—$N=S(O)_jR_5R_6$,
  j) —$SC(=O)R_7$,
  k) —$C(=O)R_{25}$,
  l) —$C(=O)NR_{27}R_{28}$,
  m) —$C(=NR_{29})R_{25}$,
  n) —$C(R_{25})(R_{28})$—$OR_{13}$,
  o) —$C(R_{25})(R_{28})$—$OC(=O)R_{13}$,
  p) —$C(R_{28})(OR_{13})$—$(CH_2)_n$—$NR_{27}R_{28}$,
  q) —$NR_{27}R_{28}$,
  r) —$N(R_{27})C(=O)R_7$,
  s) —$N(R_{27})$—$S(=O)_iR_7$,
  t) —$C(OR_{14})(OR_{15})R_{28}$,
  u) —$C(R_{25})(R_{16})$—$NR_{27}R_{26}$, or
  v) $C_{1-8}$ alkyl substituted with one or more halos, OH, =O other than at alpha position, —$S(=O)_iR_{17}$, —$NR_{27}R_{28}$, $C_{2-5}$ alkenyl, $C_{2-5}$ alkynyl, or $C_{3-8}$ cycloalkyl;

$X_1$ is N or $CR_{158}$;

$Y_1$ is
  a) $S(O)_i$,
  b) $S(NR_{159})$, or
  c) $S(NR_{159})(O)$;

$W_1$ is O or S;

$X_2$ is O or $NR_{162}$;

$X_3$ is $S(O)_i$ or $NR_{166}$;

$Y_2$ is
  a) O,
  b) NH,
  c) $CH_2$, or
  d) $S(O)_i$;

$X_4$ is
  a) O,
  b) $NR_{172}$,
  c) $S(O)_i$, or
  d) $S(O)(NR_{173})$; and $Y_3$ is CH or N;

$R_4$, $R_5$, $R_6$, $R_7$, $R_{13}$, $R_{14}$, $R_{15}$, $R_{16}$, and $R_{17}$ are the same as defined above;

$R_{25}$ is
  a) H,
  b) $C_{1-8}$ alkyl optionally substituted with one or more halos, $C_{3-8}$ cycloalkyl, $C_{1-4}$ alkyl substituted with one or more of —$S(=O)_iR_{17}$, —$OR_{13}$, or $OC(=O)R_{13}$, $NR_{27}R_{28}$, or
  c) $C_{2-5}$ alkenyl optionally substituted with CHO, or $CO_2R_{13}$;

$R_{26}$ is
  a) $R_{28}$, or
  b) $NR_{27}NR_{28}$;

$R_{27}$ and $R_{28}$ at each occurrence are the same or different and are
  a) H,
  b) $C_{1-8}$ alkyl,
  c) $C_{3-8}$ cycloalkyl,
  d) —$(CH_2)_mOR_{13}$,
  e) —$(CH_2)_n$—$NR_{21}R_{22}$, or
  f) $R_{27}$ and $R_{28}$ taken together are —$(CH_2)_2O(CH_2)_2$—, —$(CH_2)_nCH(COR_7)$—, or —$(CH_2)_2N(CH_2)_2(R_7)$;

$R_{29}$ is
  a) —$NR_{27}R_{28}$,
  b) —$OR_{27}$, or
  c) —$NHC(=O)R_{28}$;

wherein $R_{30}$ is
  a) H,
  b) $C_{1-8}$ alkyl optionally substituted with one or more halos, or
  c) $C_{1-8}$ alkyl optionally substituted with one or more OH, or $C_{1-6}$ alkoxy;

wherein E is
  a) $NR_{39}$,
  b) —$S(=O)_i$;
  c) O, or
  d) $S(O)(NR_{190})$;

$R_{38}$ is
  a) H,
  b) $C_{1-6}$ alkyl,
  c) —$(CH_2)_q$-aryl, or
  d) halo;
$R_{39}$ is
  a) H,
  b) $C_{1-6}$ alkyl optionally substituted with one or more OH, halo, or —CN,
  c) —$(CH_2)_q$-aryl,
  d) —$CO_2R_{40}$,
  e) —$COR_{41}$,
  f) —C(=O)—$(CH_2)_q$—C(=O)$R_{40}$,
  g) —S(=O)$_2$—$C_{1-16}$ alkyl,
  h) —S(=O)$_2$—$(CH_2)_q$-aryl, or
  i) —(C=O)$_j$-Het;
$R_{40}$ is
  a) H,
  b) $C_{1-6}$ alkyl optionally substituted with one or more OH, halo, or —CN,
  c) —$(CH_2)_q$-aryl, or
  d) —$(CH_2)_q$—$OR_{42}$;
$R_{41}$ is
  a) $C_{1-6}$ alkyl optionally substituted with one or more OH, halo, or —CN,
  b) —$(CH_2)_q$-aryl, or
  c) —$(CH_2)_q$—$OR_{42}$;
$R_{42}$ is
  a) H,
  b) $C_{1-6}$ alkyl,
  c) —$(CH_2)_q$-aryl, or
  d) —C(=O)—$C_{1-6}$ alkyl;
aryl is
  a) phenyl,
  b) pyridyl, or
  c) napthyl; a to c optionally substituted with one or more halo, —CN, OH, SH, $C_{1-6}$ alkyl, $C_{1-6}$ alkoxy, or $C_{1-6}$ alkylthio;
h is 1, 2, or 3;
i is 0, 1, or 2;
j is 0 or 1, with the proviso that when j is 0, $Y_2$ is —$CH_2$—;
k is 3, 4, or 5;
l is 2 or 3;
m is 4 or 5;
n is 0, 1, 2, 3, 4, or 5;
p is 0, 1, 2, 3, 4, or 5; with the proviso that n and p together are 1, 2, 3, 4, or 5;
q is 1, 2, 3, or 4;
u is 1 or 2;
w is 0, 1, 2, or 3;
x is 0, 1, 2, 3 or 4; and
y is 0, 1, 2, 3 or 4; with the proviso that x and y taken together are 3 or 4;
z is 1, 2, 3, 4 or 5, provided that i and z taken together are 2, 3, 4 or 5; and G is

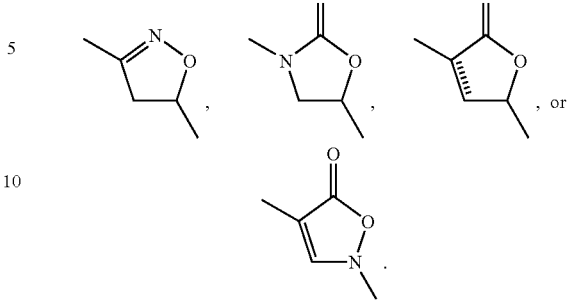

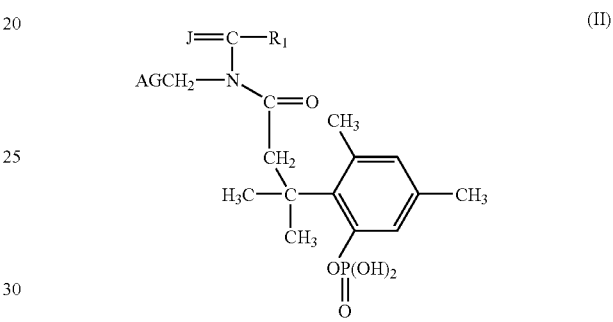

The present invention also provides an oxazolidinone derivative of Formula (II)

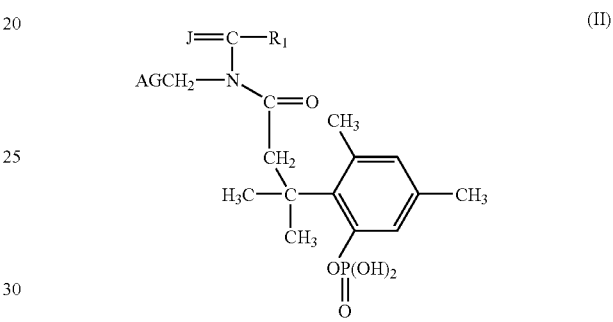

(II)

wherein J, $R_1$, G and A are as defined above.

The present invention also is directed to an oxazolidinone derivative of formula (VIII) having an improved solubility, wherein R is —$CH_2$-G-A and $R_1$, G and A are as defined above.

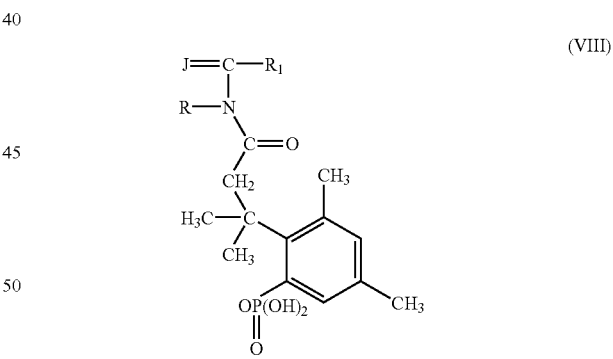

(VIII)

The present invention also is directed to a method of improving the solubility of an amide of Formula (III)

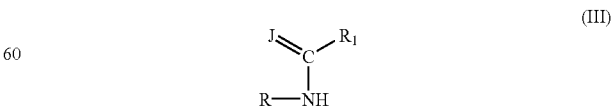

(III)

in which the compound of Formula (VIII) is prepared, wherein R is —$CH_2$-G-A and $R_1$, G and A are as defined above.

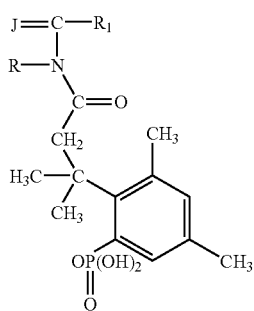
(VIII)

The present invention also is directed to a method of improving the solubility of an amide of Formula (III)

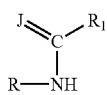
(III)

in which the compound of Formula (XII) is prepared, wherein R is —CH$_2$-G-A, with G, A, Q; R$_{310}$, R$_{410}$, R$_{510}$ and R$_{610}$ being as defined above.

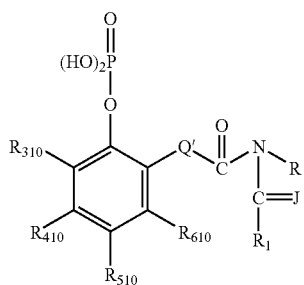
(XII)

The present invention is also directed to an oxazolidinone derivative of formula (XIII)

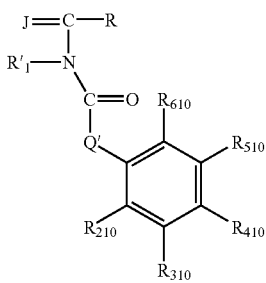
(XIII)

wherein R is -G-A;
J, G and A being as defined above;
R$_1$' is
  a) H,
  b) OH,
  c) alkyl,
  d) alkoxy,
  e) alkenyl,
  f) amino,
  g) substituted alkyl,
  h) substituted alkoxy,
  i) substituted alkenyl, or
  j) substituted amino,

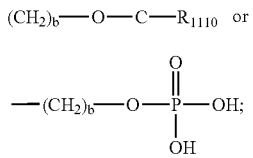
a)

b)
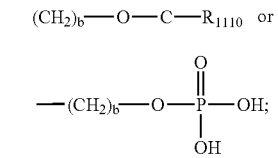

R$_{210}$ is a) $(CH_2)_b$—O—C—R$_{1110}$  or b) —$(CH_2)_b$—O—P(=O)(OH)—OH;

R$_{310}$, R$_{410}$ and R$_{510}$ each independently are
  a) H,
  b) C$_{1-4}$ alkyl,
  c) halogen,
  d) C$_{1-4}$ alkoxy,
  e) hydroxy,
  f) (CH$_2$)$_c$OP(O)(OH)$_2$,
  g) C$_{1-4}$ acyloxy, or
  h) C$_{1-4}$ alkyl substituted by halogen, hydroxy, acyloxy, NR$_{1210}$R$_{1310}$, or alkoxy; and R$_{610}$ is
  a) H,
  b) CH$_3$, or
  c) C$_2$H$_5$.

The present invention is also directed to a method of preparing an oxazolidinone derivative having an improved water solubility comprising the steps of providing an amide of formula (XVI)

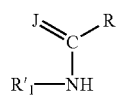
(XVI)

reacting the amide with a compound of formula (XIV)

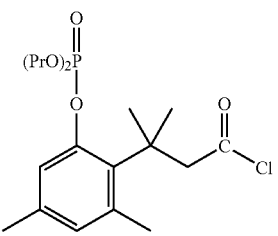
(XIV)

to form a compound of formula (XVII)

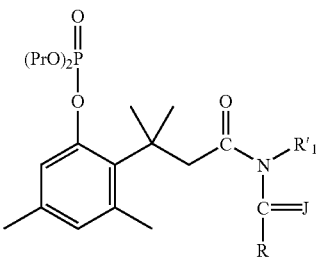

(XVII)

and removing the protecting groups to form a compound of formula (XVIII)

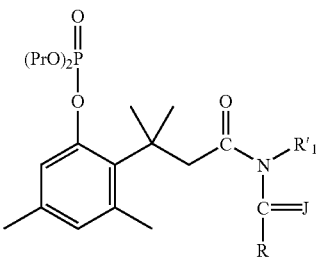

(XVIII)

wherein R is -G-A and J, $R'_1$, G, A and Pr are as described above.

DETAILED DESCRIPTION OF THE INVENTION

For the purpose of the present invention, the carbon content of various hydrocarbon containing moieties is indicated by a prefix designating the minimum and maximum number of carbon atoms in the moiety, i.e., the prefix $C_{i-j}$ defines the number of carbon atoms present from the integer "i" to the integer "j", inclusive. Thus, $C_{1-4}$ alkyl refers to alkyl of 1–4 carbon atoms, inclusive, or methyl, ethyl, propyl, butyl and isomeric forms thereof.

The terms "$C_{1-2}$ alkyl", "$C_{1-3}$ alkyl", "$C_{1-4}$ alkyl", "$C_{1-5}$ alkyl", "$C_{1-6}$ alkyl", "$C_{1-8}$ alkyl", and "$C_{1-16}$ alkyl" refer to an alkyl group having one to two, one to three, one to four, one to five, one to six, one to eight, or one to sixteen carbon atoms respectively such as, for example, methyl, ethyl, propyl, butyl, pentyl, hexyl, heptyl, octyl, nonyl, decyl, undecyl, dodecyl, tridecyl, tetradecyl and their isomeric forms thereof.

The terms "$C_{2-4}$ alkenyl", "$C_{2-5}$ alkenyl", "$C_{2-8}$ alkenyl", "$C_{2-14}$ alkenyl" and "$C_{2-16}$ alkenyl" refer to at least one double bond alkenyl group having two to four, two to five, two to eight, two to fourteen, or two to sixteen carbon atoms, respectively such as, for example, ethenyl, propenyl, butenyl, pentenyl, pentdienyl, hexenyl, hexdienyl, heptenyl, heptdienyl, octenyl, octdienyl, octatrienyl, nonenyl, nonedienyl, nonatrienyl, undecenyl, undecdienyl, dodecenyl, tridecenyl, tetradecenyl and their isomeric forms thereof.

The terms "$C_{2-5}$ alkynyl", "$C_{2-8}$ alkynyl", and "$C_{2-10}$ alkynyl" refer to at least one triple bond alkynyl group having two to five, two to eight, or two to ten carbon atoms respectively such as, for example, ethynyl, propynyl, butynyl, pentynyl, pentdiynyl, hexynyl, hexdiynyl, heptynyl, heptdiynyl, octynyl, octdiynyl, octatriynyl, nonynyl, nonediynyl, nonatriynyl and their isomeric forms thereof.

The terms "$C_{3-4}$ cycloalkyl", "$C_{3-6}$ cycloalkyl", "$C_{5-6}$ cycloalkyl", and "$C_{3-8}$ cycloalkyl" refer to a cycloalkyl having three to four, three to six, five to six, or three to eight carbon atoms respectively such as, for example, cyclopropyl, cyclobutyl, cyclopentyl, cyclohexyl, cycloheptyl, cyclooctyl, and their isomeric forms thereof.

The terms "$C_{1-4}$ alkoxy", "$C_{1-6}$ alkoxy", and "$C_{1-8}$ alkoxy" refer to an alkyl group having one to four, one to six, or one to eight carbon atoms respectively attached to an oxygen atom such as, for example, methoxy, ethoxy, propyloxy, butyloxy, pentyloxy, hexyloxy, heptyloxy, or octyloxy and their isomeric forms thereof.

The terms "$C_{1-6}$ alkylamino", and "$C_{1-8}$ alkylamino" refer to an alkyl group having one to six, or one to eight carbon atoms respectively attached to an amino moiety such as, for example, methylamino, ethylamino, propylamino, butylamino, pentylamino, hexylamino, heptylamino, or octoylamino and their isomeric forms thereof.

The terms "$C_{1-6}$ dialkylamino", and "$C_{1-8}$ dialkylamino" refer to two alkyl groups having one to six, or one to eight carbon atoms respectively attached to an amino moiety such as, for example, dimethylamino, methylethylamino, diethylamino, dipropylamino, methypropylamino, ethylpropylamino, dibutylamino, dipentylamino, dihexylamino, methylhecylamino, diheptylamino, or dioctoylamino and their isomeric forms thereof.

The terms "$C_{1-3}$ acyl", "$C_{1-4}$ acyl", "$C_{1-5}$ acyl", "$C_{1-6}$ acyl", "$C_{1-8}$ acyl", and "$C_{2-8}$ acyl" refer to a carbonyl group having an alkyl group of one to three, one to four, one to five, one to six, one to eight, or two to eight carbon atoms.

The terms "$C_{1-4}$ alkoxycarbonyl", "$C_{1-6}$ alkoxycarbonyl", and "$C_{1-8}$ alkoxycarbonyl" refer to an ester group having an alkyl group of one to four, one to six, or one to eight carbon atoms.

The term "$C_{1-8}$ alkyl phenyl" refers to an alkyl group having one to eight carbon atoms and isomeric forms thereof which is substituted with at least one phenyl radical.

The term "$C_{2-8}$ alkenyl phenyl" refers to a at least one double bond alkenyl group having one to eight carbon atoms and isomeric forms thereof which is substituted with at least one phenyl radical.

The term "$C_{1-8}$ alkyl pyridyl" refers to an alkyl group having one to eight carbon atoms and isomeric forms thereof which is substituted with at least one pyridyl radical.

The term "$C_{1-8}$ hydroxyl" refers to an alkyl group having one to eight carbon atoms and isomeric forms thereof attached to a hydroxy group.

The term "$C_{1-8}$ alkylsulfonyl" refers to an alkyl group having one to eight carbon atoms and isomeric forms thereof attached to a $SO_2$ moiety.

The term "$C_{1-6}$ alkylthio" refers to an alkyl group having one to six carbon atoms and isomeric forms thereof attached to a sulfur atom.

The term "Het" refers to 5 to 10 membered saturated, unsaturated or aromatic heterocyclic rings containing one or more oxygen, nitrogen, and sulfur forming such groups as, for example, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5,- dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl, 1-purinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone. Each of these moieties may be substituted as appropriate.

The term het$^1$ at each occurrence is independently a C-linked 5- or 6-membered heterocyclic ring having 1 to 4 heteroatoms selected from the group consisting of oxygen, nitrogen, and sulfur within the ring.

The term het$^2$ at each occurrence is independently a N-linked 5- or 6-membered heterocyclic ring having 1 to 4 nitrogen and optionally having one oxygen or sulfur within the ring.

The term Het$_1$ is a 5- or 6-membered heteroaromatic moiety having 1–3 N, O or S atoms, optionally substituted with the following:
  a) F,
  b) Cl,
  c) $C_{1-3}$ alkoxy,
  d) $C_{1-3}$ alkylthio, or
  e) CN.

The term het$_1$ is a C-linked 5- or 6-membered saturated or unsaturated heterocyclic ring having 1, 2, or 3 heteroatoms selected from the group consisting of oxygen, sulfur, and nitrogen, which is optionally fused to a benzene ring.

The term halo refers to fluoro, chloro, bromo, or iodo.

The term Pr refers to a suitable phosphate protecting group, such as benzyl, alkyl, tert-butyl, etc.

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form.

When Q is the structure of

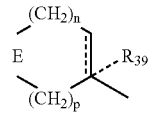

the dotted line in the heterocyclic ring means that this bond can be either single or double. In the case where the dotted line is a double bond, the $R_{39}$ group will not be present.

The compounds of this invention contain a chiral center at C5 of the isoxazoline ring, and as such there exist two enantiomers or a racemic mixture of both. This invention relates to both the enantiomers, as well as mixtures containing both the isomers. In addition, depending on substituents, additional chiral centers and other isomeric forms may be present in any of A or $R_1$ group, and this invention embraces all possible stereoisomers and geometric forms in these groups.

The compounds of this invention are useful for treatment of microbial infections in humans and other warm blooded animals, under both parenteral and oral administration. The inventive compounds have antibacterial activity against a number of human and veterinary pathogens including Gram-positive aerobic bacteria such as multiply-resistant staphylococci, streptococci and enterococci, Gram-negative organisms such as *H. influenzae* and *M. catarrhalis*, anaerobic organisms such as *Bacteroides* spp. and *Clostridasppa, Mycobacterium tuberculosis, M. avium* and *M.* spp. and organisms such as *Mycoplasma* spp.

The pharmaceutical compositions of this invention may be prepared by combining the compounds of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound according to this invention.

The quantity of active component, that is the compound according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., 2–4 four times per day.

When the compounds according to this invention are administered parenterally, i.e., by injection, for example, by intravenous injection or by other parenteral routes of administration. Pharmaceutical compositions for parenteral administration will generally contain a pharmaceutically acceptable amount of the compound or a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compound of this invention generally will be dissolved in the carrier in an amount sufficient to provide a pharmaceutically acceptable injectable concentration in the range of about 1 mg/mL to about 400 mg/mL of solution. The resulting liquid pharmaceutical composition will be administered so as to obtain the above-mentioned antibacterially effective amount of dosage. The compounds according to this invention are advantageously administered orally in solid and liquid dosage forms.

As a topical treatment an effective amount of Formula I is admixed in a pharmaceutically acceptable gel or cream vehicle that can be applied to the patient's skin at the area of treatment. Preparation of such creams and gels is well known in the art and can include penetration enhancers.

The present invention improves the solubility and bioavailability of an amide of Formula III

by converting it into a prodrug of Formula (VIII). The general scheme for preparing the prodrug of Formula (VIII) is shown below in Schemes 1 and 2.

Scheme 1

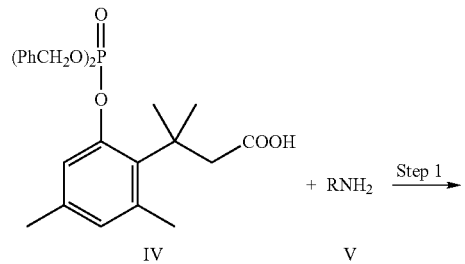

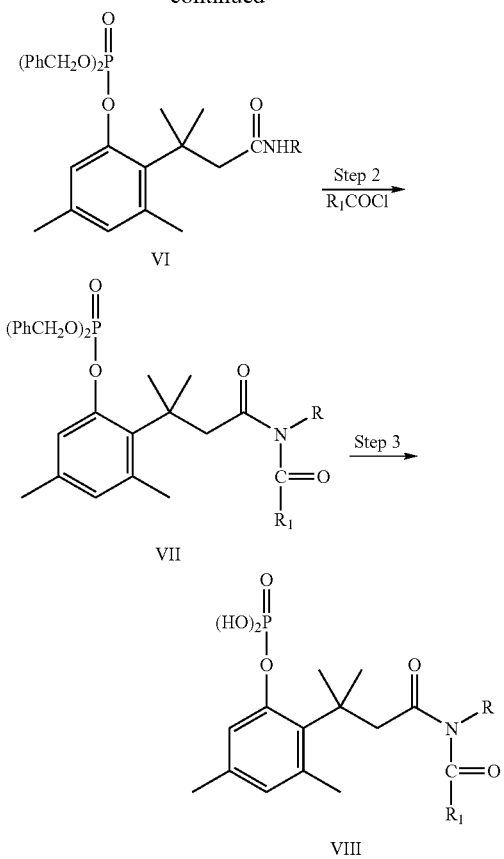

In the above reaction scheme, the carboxylic acid derivative of Formula IV is prepared as described in M. G. Nicolaou, C.-S. Yuan and R. T. Borchardt, *J. Med. Chem.* 1996, 61, 8636–8641. Condensation of the amine of Formula V with the carboxylic acid of IV is accomplished by methods known in the art for amide or peptide bond formation. Examples include 1-(3-dimethylaminopropyl)-3-ethylcarbodiimide hydrochloride and 4-(dimethylamino)pyridine and solvents such as methylene chloride at reaction temperatures of 0 to 24° C., 1-(3-dimethylaminopropyl)-3-ethylcarbodiimide hydrochloride and 1-hydroxybenzotriazole and solvents such as dimethylformamide at 0 to 24° C., and bis(2-oxo-3-oxazolidinyl)phosphinic chloride and triethylamine and solvents such as methylene chloride at 0 to 24° C.

In Step 2 of Scheme 1, the amide of VI undergoes an acylation reaction to give the compound of VII, wherein J is an oxygen atom. This reaction is conveniently carried out by allowing the compound of VI to react with an acid chloride in the presence of an efficient acid scavenger. Solvents such as methylene chloride, ethylene chloride or carbon tetrachloride at a temperature of from 24° C. to the reflux temperature of the solvent can be used. Acid scavengers such as 3 Å units molecular sieves, propylene oxide, 1,8-bis(dimethylamino)naphthalene and methyl trimethylsilyl-carbamate are suitable for use in this reaction. In Step 3 of Scheme 1, the phosphate esters of Formula VII are deprotected. This can be carried out by hydrogenolysis at atmospheric pressure and ambient temperature with a palladium catalyst. Solvents such as tetrahydrofuran, diethylether, or 1,2-dimethoxyethane can be used for this reaction.

Alternatively, compounds of formula (VIII) can be prepared according to the following Scheme 2. In Scheme 2, $P_r$ of formula (XIII) represents a suitable phosphate protecting group, such as benzyl, alkyl or tert-butyl.

Scheme 2

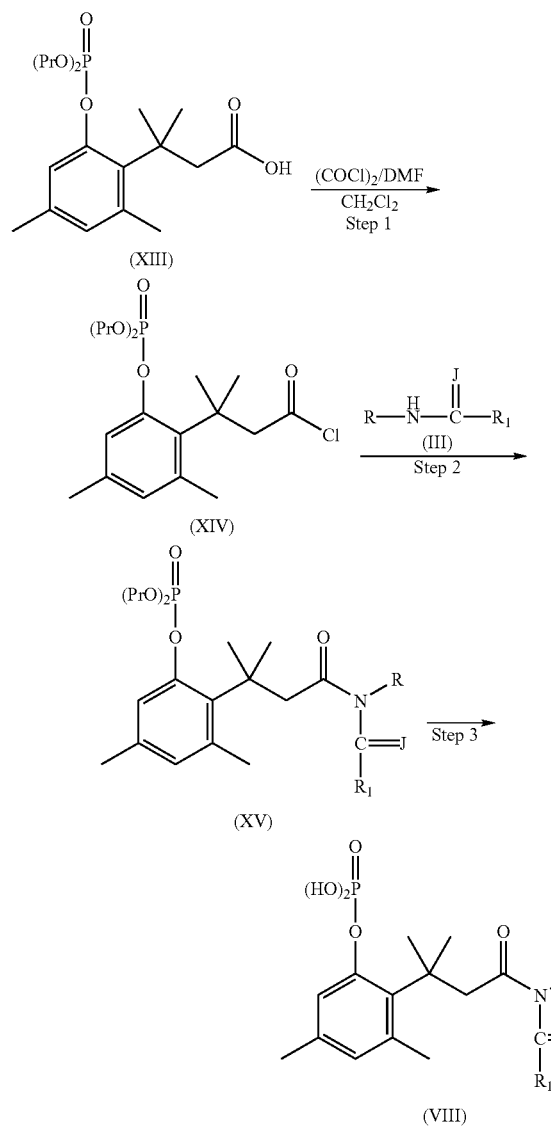

In Step 1, the acid (XIII) is converted to the acid chloride (XIV) with, for example, oxalyl chloride and dimethylformamide in a solvent, such as methylene chloride, at temperatures of from 0 to 30° C. In Step 2, the compound of formula (XIV) is allowed to react with the compound of formula (III) in a solvent, such as methylene chloride, ethylene chloride or acetonitrile, in the presence of an efficient acid scavenger, such as methyl trimethylsilylcarbamate, at the reflux temperature of the solvent. In Step 3, the phosphate protecting groups of the compound of formula (XV) is removed by methods known in the art.

Examples of amides containing oxazolidinone groups that can be used in the present invention are shown below. The preparation of the following amides of Examples 1–434 are shown in U.S. Pat. No. 6,362,189 B1, the disclosure of which is herein incorporated by reference thereto.

TABLE A

EXAMPLE 1: (S)-N-[[3-[3-Fluoro-4-(4-morpholinyl)phenyl]-2-oxo-5-oxazolidinyl]methyl]thioacetamide (I)
EXAMPLE 2: (S)-N-[[3-[3-Fluoro-4-[4-(5-methyl-1,3,4-thiadiazol-2-yl)-1-piperazinyl]phenyl]-2-oxo-5-oxazolidinyl]methyl]thioacetamide (2)
EXAMPLE 3: (S)-N-[[3-[3-Fluoro-4-[2',5'-dioxospiro[piperidine-4,4'-imidazolidine]-1-yl]phenyl]-2-oxo-5-oxazolidinyl]methyl]thioacetamide (3).
EXAMPLE 4: (S)-N-[[3-[3-Fluoro-4-(4-morpholinyl)phenyl]-2-oxo-5-oxazolidinyl]methyl]thioacetamide (4).
EXAMPLE 5: (S)-cis-N-[[3-[3-Fluoro-4-(tetrahydro-1-oxido-2H-thiopyran-4-yl)phenyl]-2-oxo-5-oxazolidinyl]methyl]ethanethioamide
EXAMPLE 6: (S)-trans-N-[[3-[3-Fluoro-4-(tetrahydro-1-oxido-2H-thiopyran-4-yl)phenyl]-2-oxo-5-oxazolidinyl]methyl]ethanethioamide
EXAMPLE 7: (S)-N-[[3-[3-Fluoro-4-(tetrahydro-1,1-dioxido-2H-thiopyran-4-yl)phenyl]-2-oxo-5-oxazolidinyl]methyl]ethanethioamide
EXAMPLE 8: (S)-N-[[3-[3-Fluoro-4-(4-morpholinyl)phenyl]-2-oxo-5-oxazolidinyl]methyl]-thioformamide (7).
EXAMPLE 9: (S)-N-[[3-[3-Fluoro-4-(4-morpholinyl)phenyl]-2-oxo-5-oxazolidinyl]methyl]thiopropion-amide (9).
EXAMPLE 10: (S)-N-[[3-[3-Fluoro-4-(4-morpholinyl)phenyl]-2-oxo-5-oxazolidinyl]methyl]-2-chlorothioacetamide (11).
EXAMPLE 11: (S)-N-[[3-[3-Fluoro-4-(4-moropholinyl)phenyl]-2-oxo-5-oxazolidinyl]methyl]-α,α,α-trifluorothioacetamide (13).
EXAMPLE 12: (S)-N-[[3-[3-Fluoro-4-(4-morpholinyl)phenyl]-2-oxo-5-oxazolidinyl]methyl]-α-fluorothioacetamide (15).
EXAMPLE 13: (S)-N-[[3-[3-Fluoro-4-(4-morpholinyl)phenyl]-2-oxo-5-oxazolidinyl]methyl]-α,α-difluorothioacetamide (17).
EXAMPLE 14: (S)-N-[[3-[3-Fluoro-4-(4-morpholinyl)phenyl]-2-oxo-5-oxazolidinyl]methyl]-α-cyanothioacetamide (19).
EXAMPLE 15: (S)-N-[[3-[3-Fluoro-4-(4-morpholinyl)phenyl]-2-oxo-5-oxazolidinyl]methyl]-α,α-dichlorothioacetamide (21).
EXAMPLE 16: (S)-N-[[3-[3-Fluoro-4-(4-morpholinyl)phenyl]-2-oxo-5-oxazolidinyl]methyl]-α-(methoxycarbonyl)thioacetamide (23).
EXAMPLE 17: (S)-N-[[3-[4-[1-[1,2,4]Triazolyl]phenyl]-2-oxo-5-oxazolidinyl]methyl]thioacetamide (25).
EXAMPLE 18: (S)-N-[[3-[4-[1-[1,2,4]Triazolyl]phenyl]-2-oxo-5-oxazolidinyl]methyl]thioacetamide (25).
EXAMPLE 19: (S)-N-[[3-[1-(Hydroxyacetyl)-5-indolinyl]-2-oxo-5-oxazolidinyl]methyl]thioacetamide (28).
EXAMPLE 20: (S)-N-[[3-[3-Fluoro-4-[4-(hydroxyacetyl)-1-piperazinyl]phenyl]-2-oxo-5-oxazolidinyl]methyl]thioacetamide (30).
EXAMPLE 21: (S)-N-[[3-[3-Fluoro-4-(4-thiomorpholinyl)phenyl]-2-oxo-5-oxazolidinyl]methyl]thio-acetamide (32).
EXAMPLE 22: (S)-N-[[3-[3-Fluoro-4-(4-thiomorpholinyl)phenyl]-2-oxo-5-oxazolidinyl]methyl]thio-acetamide, thiomorpholine S-oxide (34).
EXAMPLE 23: (S)-N-[[3-[3-Fluoro-4-(4-thiomorpholinyl)phenyl]-2-oxo-5-oxazolidinyl]methyl]thio-acetamide, thiomorpholine S, S-dioxide (36).
EXAMPLE 24: (S)-N-[[3-[3,5-Difluoro-4-[4-(hydroxyacetyl)-1-piperazinyl]phenyl]-2-oxo-5-oxazolidinyl]methyl]thioacetamide (38).

TABLE B

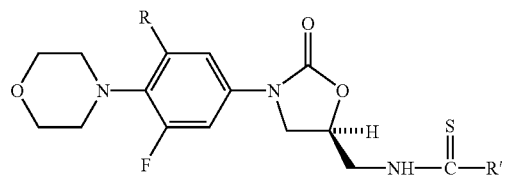

| Example No. | Compound | R, R' |
|---|---|---|
| 25 | (S)-N-[[3-[3-Fluoro-4-(4-morpholinyl)-phenyl]-2-oxo-5-oxazolidinyl]methyl]-2-methylpropanethioamide; mp 152–153°C. (dec.); Anal. calcd for C₁₈H₂₄FN₃O₃S: C, 56.67; H, 6.34; N, 11.02. Found: C, 56.58; H, 6.41; N, 10.81 | R = H, R' = CH(CH₃)₂ |

TABLE B-continued

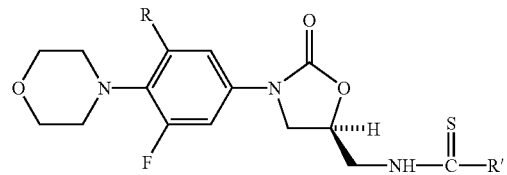

| Example No. | Compound | R, R' |
|---|---|---|
| 26 | (S)-N-[[3-[3-Fluoro-4-(4-morpholinyl)-phenyl]-2-oxo-5-oxazolidinyl]methyl]-cyclopropane-carbothioamide; mp 155–156° C.; Anal. calcd for C₁₈H₂₂FN₃O₃S: C, 56.98; H, 5.84; N, 11.07. Found: C, 56.98; H, 5.85; N, 10.97 | |
| 27 | (S)-N-[[3-[3,5-Difluoro-4-(4-morpholinyl)-phenyl]-2-oxo-5-oxazolidinyl]methyl]thioacetamide | R = F, R' = CH₃ |

TABLE C

| Example No. | Compound | Amine | Dithio Compound (from Prepartion Z) |
|---|---|---|---|
| 28 | (S)-N-[[3-[3-Fluoro-4-(4-thiomorpholinyl)-phenyl]-2-oxo-5-oxazolidinyl]methyl]-propanethioamide, thiomorphoilne S-oxide; mp 196–197° C.; Anal. calcd for C₁₇H₂₂FN₃O₃S₂: C, 51.11; H, 5.55; N, 10.52; S, 16.05. Found: C, 50.99; H, 5.60; N, 10.55; S, 15.75 | 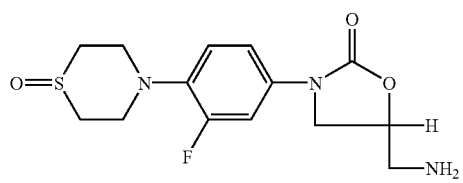 | Z (a) |
| 29 | S)-N-[[3-[3-Fluoro-4-(4-thiomorpholinyl)-phenyl]-2-oxo-5-oxazolidinyl]methyl]-2-methylpropanethioamide, thiomorpholine S-oxide; mp 195–196° C.; Anal. calcd for C₁₈H₂₄FN₃O₃S₂: C, 52.28; H, 5.85; N, 10.16; S, 15.51. Found: C, 52.24; H, 5.97; N, 10.16; S, 15.28 | Same as above | Z (b) |

TABLE C-continued

| Example No. | Compound | Amine | Dithio Compound (from Prepartion Z) |
|---|---|---|---|
| 30 | (S)-N-[[3-[3-Fluoro-4-(4-thiomorpholinyl)-phenyl]-2-oxo-5-oxazolidinyl]methyl]-cyclopropanecarbothioamide, thiomorpholine S-oxide; mp 109–110° C.; Anal. calcd for $C_{18}H_{22}FN_3O_3S_2$: C, 52.54; H, 5.39; N, 10.21; S, 15.58. Found: C, 52.48; H, 5.51; N, 10.28; S, 15.29 | Same as above | Z (c) |
| 31 | (S)-N-[[3-[3-Fluoro-4-(4-thiomorphoriny 1)phenyl]-2-oxo-5 oxazolidinyl]methyl] butanethioamide, thiomorpholine S-oxide | Same as above | Z (d) |
| 32 | (S)-N-[[3-[3-Fluoro-4-(4-thiomorpholinyl) phenyl]-2-oxo-5 oxazolidinyl]methyl]-3 methylbutanethioamide, thiomorpholine S-oxide | Same as above | Z (e) |
| 33 | (S)-N-[[3-[3-Fluoro-4-(4-thiomorpholinyl) phenyl]-2-oxo-5 oxazolidinyl]methyl]-2 methylbutanethioamide, thiomorpholine S-oxide | Same as above | Z (f) |
| 34 | (S)-N-[[3-[3-Fluoro-4-(4-thiomorpholinyl) phenyl]-2-oxo-5 oxazolidinyl]methyl] 3,3-dimethylbutanethio-amide, thiomorpholine S-oxide | Same as above | Z (g) |
| 35 | (S)-N-[[3-[3-Fluoro-4-(4-thiomorpholinyl) phenyl]-2-oxo-5 oxazolidinyl]methyl] cyclobutanecarbothioamide, thiomorpholine S-oxide | Same as above | Z (h) |
| 36 | (S)-N-[[3-[3-Fluoro-4-(4-thiomorpholinyl) phenyl]-2-oxo-5 oxazolidinyl]methyl]-1-cyclopentanecarbothio-amide, thiomorpholine S-oxide | Same as above | Z (i) |
| 37 | (S)-N-[[3-[3-Fluoro-4-(4-thiomorpholinyl) phenyl]-2-oxo-5 oxazolidinyl]methyl] cyclohexanecarbothio-amide, thiomorpholine S-oxide | Same as above | Z(j) |
| 38 | (S)-N-[(3-[3-Fluoro-4-(4-thiomorpholinyl)-phenyl]-2-oxo-5 oxazolidinyl]methyl]-2-cyclopropylethanethio-amide, thiomorpholine S-oxide | Same as above | Z (k) |

TABLE C-continued

| Example No. | Compound | Amine | Dithio Compound (from Prepartion Z) |
|---|---|---|---|
| 39 | (S)-N-[[3-[3-Fluoro-4-(4-thiomorpholinyl)-phenyl]-2-oxo-5 oxazolidinyl]methyl]-2-cyclobutylethanethio-amide, thiomorpholine S-oxide | Same as above | Z (l) |
| 40 | (S)-N-[[3-[3-Fluoro-4-(4-thiomorpholinyl)-phenyl]-2-oxo-5 oxazolidinyl]methyl]-2-cyclopentylethanethio-amide, thiomorpholine S-oxide | Same as above | Z (m) |
| 41 | (S)-N-[[3-[3-Fluoro-4-(4-thiomorpholinyl)-phenyl]-2-oxo-5 oxazolidinyl]methyl]-thioacetamide, thiomorpholine S-oxide | [structure: 2,6-difluorophenyl with 4-(thiomorpholine S-oxide) and 5-(aminomethyl)-2-oxo-oxazolidinyl substituents] | Ethyl dithioacetate |
| 42 | (S)-N-[[3-[3-Fluoro-4-(4-thiomorpholinyl)-phenyl]-2-oxo-5 oxazolidinyl]methyl]-propanethioamide, thiomorpholine S-oxide | Same as above | Z (a) |
| 43 | (S)-N-[[3-[3-Difluoro-4-(4-thiomorpholinyl)-phenyl]-2-oxo-5-oxazolidinyl]methyl]-2-methylpropanethio-amide, thiomorpholine S-oxide | Same as above | Z (b) |
| 44 | (S)-N-[[3-[3-Difluoro-4-(4-thiomorpholinyl)-phenyl]-2-oxo-5-oxazolidinyl]methyl]-cyclopropanecarbothio-amide, thiomorpholine S-oxide | Same as above | Z (c) |
| 45 | (S)-N-[[3-[4-(4 thiomorpholinyl)-phenyl]-2-oxo-5-oxazolidinyl]methyl]-thioacetamide, thiomorpholine S-oxide | [structure: phenyl with 4-(thiomorpholine S-oxide) and 5-(aminomethyl)-2-oxo-oxazolidinyl substituents] | Ethyl dithioacetate |
| 46 | (S)-N-[[3-[4-(4 thiomorpholinyl)-phenyl]-2-oxo-5-oxazolidinyl]methyl]-propanethioamide, thiomorpholine S-oxide | Same as above | Z (a) |
| 47 | (S)-N-[[3-[4-(4 thiomorpholinyl)-phenyl]-2-oxo-5-oxazolidinyl]methyl]-2-methylpropanethio-amide, thiomorpholine S-oxide | Same as above | Z (b) |

TABLE C-continued

| Example No. | Compound | Amine | Dithio Compound (from Prepartion Z) |
|---|---|---|---|
| 48 | (S)-N-[[3-[4-(4 thiomorpholinyl)-phenyl]-2-oxo-5-oxazolidinyl]methyl]-cyclopropanecarbothio-amide, thiomorpholine S-oxide | Same as above | Z (c) |
| 49 | (S)-N-[[3-[3,5-Difluoro-4-(4-hydroxyacetyl)-1-piperazinyl]pheny1]-2-oxo-5-oxazolidinyl]-methyl]propanethioamide | | Z (a) |
| 50 | (S)-N-[[3-[3,5-Difluoro-4-(4-hydroxyacetyl)-1-piperazinyl]pheny-1]-2-oxo-5-oxazolidinyl]-methyl]-2-methyl-propanethioamide | Same as above | Z (b) |
| 51 | (S)-N-[[3-[3,5-Difluoro-4-(4-hydroxyacetyl)-1-piperazinyl]pheny-1]-2-oxo-5-oxazolidinyl]-methyl]cyclopropanethio-amide | Same as above | Z (c) |
| 52 | (S)-N-[[3-[3-[4 (hydroxyacetyl)-1-piperazinyl]pheny1]-2-oxo-5-oxazolidinyl]-methyl]propanethioamide | | Z (a) |
| 53 | (S)-N-[[3-[3-[4 (hydroxyacetyl)-1-piperazinyl]pheny1]-2-oxo-5-oxazolidinyl]-methyl]-2-methyl-propanethio-amide | Same as above | Z (b) |
| 54 | (S)-N-[[3-[3-[4 (hydroxyacetyl)-1-piperazinyl]pheny1]-2-oxo-5-oxazolidinyl]-methyl]cyclopropane-carbothio-amide | Same as above | Z (c) |

TABLE D

| Example No. | Compound | Amine | Dithio Compound (from Preparation Z) |
|---|---|---|---|
| 55 | (S)-N-[[3-[3-Fluoro-4-(4-thiomorpholinyl)-phenyl]-2-oxo-5-oxazolidinyl]methyl]-propanethioamide, thiomorpholine S,S-dioxide | 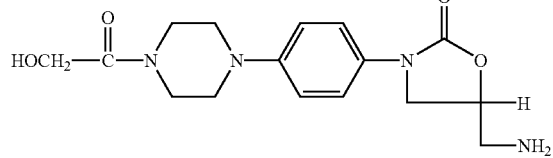 | Z (a) |
| 56 | (S)-N-[[3-[3-Fluoro-4-(4-thiomorpholinyl)-phenyl]-2-oxo-5-oxazolidinyl]methyl]-2-methylpropanethioamide, thiomorpholine S,S-dioxide | Same as above | Z (b) |
| 57 | (S)-N-[[3-[3-Fluoro-4-(4-thiomorpholinyl)-phenyl]-2-oxo-5-oxazolidinyl]methyl]-cyclopropanecarbothioamide, thiomorpholine S,S-dioxide | Same as above | Z (c) |
| 58 | (S)-N-[[3-[3,5-Difluoro-4-(4-thiomorpholinyl)-phenyl]-2-oxo-5-oxazolidinyl]-methyl]thioacetamide, thiomorpholine S,S-dioxide | 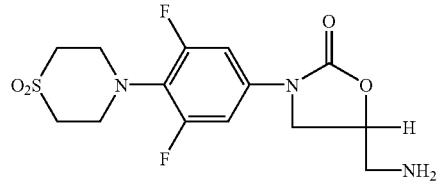 | |
| 59 | (S)-N-[[3-[3,5-Difluoro-4-(4-thiomorpholinyl)-phenyl]-2-oxo-5-oxazolidinyl]methyl]-propanethioamide, thiomorpholine S,S-dioxide | Same as above | Z (a) |
| 60 | (S)-N-[[3-[3,5-Difluoro-4-(4-thiomorpholinyl)-phenyl]-2-oxo-5-oxazolidinyl]methyl]-2-methylpropanethioamide, thiomorpholine S,S-dioxide | Same as above | Z (b) |

TABLE D-continued

| Example No. | Compound | Amine | | Dithio Compound (from Preparation Z) |
|---|---|---|---|---|
| 61 | (S)-N-[[3-[3,5-Difluoro-4-(4-thiomorpholinyl)-phenyl]-2-oxo-5-oxazolidinyl]methyl]cyclopropanecarbothioamide, thiomorpholine S,S-dioxide | Same as above | | Z (c) |
| 62 | (S)-N-[[3-[4-(4-thiomorpholinyl)phenyl]-2-oxo-5-oxazolidinyl]-methyl]thioacetamide, thiomorpholine S,S-dioxide | 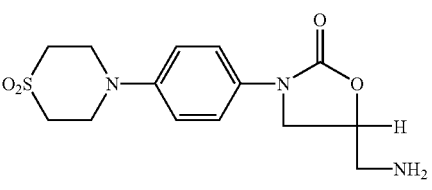 | | Ethyl dithioacetate |
| 63 | (S)-N-[[3-[4-(4-thiomorpholinyl)phenyl]-2-oxo-5-oxazolidinyl]-methyl]propanethioamide, thiomorpholine S,S-dioxide | Same as above | | Z (a) |
| 64 | (S)-N-[[3-[4-(4-thiomorpholinyl)phenyl]-2-oxo-5-oxazolidinyl]-methyl]-2-methyl-propanethioamide, thiomorpholine S,S-dioxide | Same as above | | Z (b) |
| 65 | (S)-N-[[3-[4-(4-thiomorpholinyl)phenyl]-2-oxo-5-oxazolidinyl]-methyl]cyclopropane-carbothioamide, thiomorpholine S,S-dioxide | Same as above | | Z (c) |

TABLE E

| Example No. | Compound | Amine | | Dithio Compound (from Preparation Z) |
|---|---|---|---|---|
| 66 | (S)-N[[3-[3-Fluoro-4-(4-thiomorpholinyl)-phenyl]-2-oxo-5-oxazolidinyl]methyl]-propanethioamide | 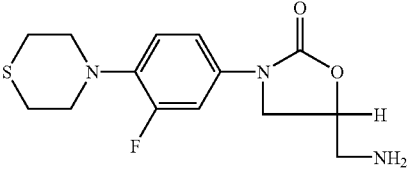 | | Z (a) |

TABLE E-continued

| Example No. | Compound | Amine | Dithio Compound (from Preparation Z) |
|---|---|---|---|
| 67 | (S)-N-[[3-[3-Fluoro-4-(4-thiomorpholinyl)-phenyl]-2-oxo-5-oxazolidinyl]methyl]-2-methylpropanethioamide | Same as above | Z (b) |
| 68 | (S)-N-[[3-[3-Fluoro-4-(4-thiomorpholinyl)-phenyl]-2-oxo-5-oxazolidinyl]methyl]-cyclopropanecarbothioamide | Same as above | Z (c) |
| 69 | (S)-N-[[3-[3-Fluoro-4-(4-thiomorpholinyl)-phenyl]-2-oxo-5-oxazolidinyl]methyl] butanethioamide | Same as above | Z (d) |
| 70 | (S)-N-[[3-[3-Fluoro-4-(4-thiomorpholinyl)-phenyl]-2-oxo-5-oxazolidinyl]methyl]-3-methylbutanethioamide | Same as above | Z (e) |
| 71 | (S)-N-[[3-[3-Fluoro-4-(4-thiomorpholinyl)-phenyl]-2-oxo-5-oxazolidinyl]methyl]-2-methylbutanethioamide | Same as above | Z (f) |
| 72 | (S)-N-[[3-[3-Fluoro-4-(4-thiomorpholinyl)-phenyl]-2-oxo-5-oxazolidinyl]methyl]-3,3-dimenthylbutanethioamide | Same as above | Z (g) |
| 73 | (S)-N-[[3-[3-Fluoro-4-(4-thiomorpholinyl)-phenyl]-2-oxo-5-oxazolidinyl]methyl]-cyclobutanecarbothioamide | Same as above | Z (h) |

TABLE E-continued

| Example No. | Compound | Amine | Dithio Compound (from Preparation Z) |
|---|---|---|---|
| 74 | (S)-N-[[3-[3-Fluoro-4-(4-thiomorpholinyl)-phenyl]-2-oxo-5-oxazolidinyl]methyl]-cyclopentanecarbothioamide | Same as above | Z (i) |
| 75 | (S)-N-[[3-[3-Fluoro-4-(4-thiomorpholinyl)-phenyl]-2-oxo-5-oxazolidinyl]methyl]-cyclohexanecarbothioamide | Same as above | Z (j) |
| 76 | (S)-N-[[3-[3-Fluoro-4-(4-thiomorpholinyl)-phenyl]-2-oxo-5-oxazolidinyl]methyl]-2-cyclopropylethanethioamide | Same as above | Z (k) |
| 77 | (S)-N-[[3-[3-Fluoro-4-(4-thiomorpholinyl)-phenyl]-2-oxo-5-oxazolidinyl]methyl]-2-cyclobutylethanethioamide | Same as above | Z (l) |
| 78 | (S)-N-[[3-[3-Fluoro-4-(4-thiomorpholinyl)-phenyl]-2-oxo-5-oxazolidinyl]methyl]-2-cyclopentylethanethioamide | Same as above | Z (m) |
| 79 | (S)-N-[[3-[3,5-Difluoro-4-(4-thiomorpholinyl)-phenyl]-2-oxo-5-oxazolidinyl]methyl]thioacetamide | (structure shown) | Ethyl dithioacetate |
| 80 | (S)-N-[[3-[3,5-Difluoro-4-(4-thiomorpholinyl)-phenyl]-2-oxo-5-oxazolidinyl]methyl]propanethioamide | Same as above | Z (a) |

TABLE E-continued

| Example No. | Compound | Amine | Dithio Compound (from Preparation Z) |
|---|---|---|---|
| 81 | (S)-N-[[3-[3,5-Difluoro-4-(4-thiomorpholinyl)-phenyl]-2-oxo-5-oxazolidinyl]methyl]-2-methylpropanethioamide | Same as above | Z (b) |
| 82 | (S)-N-[[3-[3,5-Difluoro-4-(4-thiomorpholinyl)-phenyl]-2-oxo-5-oxazolidinyl]methyl]cyclopropanecarbothio-amide | Same as above | Z (c) |
| 83 | (S)-N-[[3-[4-(4-thio-morpholinyl)phenyl]-2-oxo-5-oxazolidinyl]-methyl]thioacetamide | | |
| 84 | (S)-N-[[3-[4-(4-thio-morpholinyl)phenyl]-2-oxo-5-oxazolidinyl]-methyl]propanethio-amide | Same as above | Z (a) |
| 85 | (S)-N-[[3-[4-(4-thio-morpholinyl)phenyl]-2-oxo-5-oxazolidinyl]-methyl]-2-methyl-propanethioamide | Same as above | Z (b) |
| 86 | (S)-N-[[3-[4-(4-thio-morpholinyl)phenyl]-2-oxo-5-oxazolidinyl]-methyl]cyclopropane-carbothioamide | Same as above | Z (c) |

EXAMPLE 87

(S)-N-[[3-[3-Fluoro-4-(4-thiomorpholinyl)phenyl]-2-oxo-5-oxazolidinyl]methyl]-1-azetidinecarbothioamide, thiomorpholine S-oxide; Anal. Calcd for $C_{18}H_{23}FN_4O_3S_2$, C, 50.69; H, 5.43; N, 13.14. Found: C, 50.79; H, 5.45; N, 12.82; mp 213–214° C.

EXAMPLE 88

(S)-N-[[3-[3-Fluoro-4-(4-thiomorpholinyl)phenyl]-2-oxo-5-oxazolidinyl]methyl]-1-azetidinecarbothioamide

EXAMPLE 89

(S)-N-[[3-[3-Fluoro-4-[4-(hydroxyacetyl)-1-piperazinyl]phenyl-2-oxo-5-oxazolidinyl]methyl]propanethioamide

TABLE F

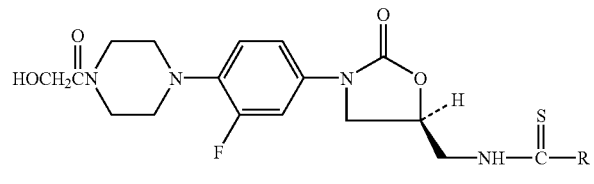

| Example No. | Compound | |
|---|---|---|
| 90 | (S)-N-[[3-[3-Fluoro-4-[4-(hydroxyacetyl)-1-piperazinyl]phenyl]-2-oxo-5-oxazolidinyl]methyl]-2-methylpropane-thioamide; Anal. calcd for $C_{20}H_{27}FN_4O_4S$: C, 54.78; H, 6.21; N, 12.78; S, 7.21. Found: C, 54.67; H, 6.34; N, 12.41; S, 7.15 | R = CH(CH$_3$)$_2$ |
| 91 | (S)-N-[[3-[3-Fluoro-4-(hydroxyacetyl)-1-piperazinyl]phenyl]-2-oxo-5-oxazolidinyl]methyl]cyclopropane-carbothioamide; mp 179–181° C.; Anal. calcd for $C_{20}H_{25}FN_4O_4S$: C, 55.03; H, 5.77; N, 12.84; 5, 7.34. Found: C, 55.15; H, 5.72; N, 12.76; 5, 7.09 | R = ▷ (cyclopropyl) |
| 92 | (S)-N-[[3-[3-Fluoro-4-(hydroxyacetyl)-1-piperazinyl]phenyl]-2-oxo-5-oxazolidinyl]methyl]butane thioamlde | R = CH$_2$—CH$_2$—CH$_3$ |
| 93 | (S)-N-[[3-[3-Fluoro-4-(hydroxyacetyl)-1-piperazinyl]phenyl]-2-oxo-5-oxazolidinyl]methyl]-3-methylbutane-thioamide | R = CH$_2$—CH(CH$_3$)—CH$_3$ |
| 94 | (S)-N-[[3-[3-Fluoro-4-(hydroxyacetyl)-1-piperazinyl]phenyl]-2-oxo-5-oxazolidinyl]methyl]-2-methylbutane thioamide | R = CH(CH$_3$)—CH$_2$—CH$_3$ |
| 95 | (S)-N-[[3-[3-Fluoro-4-(hydroxyacetyl)-1-piperazinyl]phenyl]-2-oxo- oxazolidinyl oxazolidinyl]methyl]-3,3-dimethyl-butanethioamide | R = CH$_2$—C(CH$_3$)$_3$ |
| 96 | (S)-N-[[3-[3-Fluoro-4-(hydroxyacetyl)-1-piperazinyl]phenyl]-2-oxo-5-oxazolidinyl]methyl]cyclobutane-carbothioamide | R = ◇ (cyclobutyl) |

TABLE F-continued

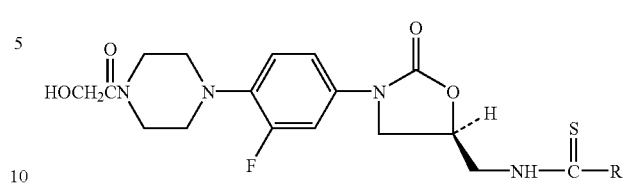

| Example No. | Compound | |
|---|---|---|
| 97 | (S)-N-[[3-[3-Fluoro-4-(hydroxyacetyl)-1-piperazinyl]phenyl]-2-oxo-5-oxazolidinyl]methyl]cyclopentane-carbothioamide | R = cyclopentyl |
| 98 | (S)-N-[[3-[3-Fluoro-4-(hydroxyacetyl)-1-piperazinyl]phenyl]-2-oxo-5-oxazolidinyl]methyl]cyclohexane-carbothioamide | R = cyclohexyl |
| 99 | (S)-N-[[3-[3-Fluoro-4-(hydroxyacetyl)-1-piperazinyl]phenyl]-2-oxo-5-oxazolidinyl]methyl]-2-cyclopropyl-ethanethioamide | R = CH$_2$—cyclopropyl |
| 100 | (S)-N-[[3-[3-Fluoro-4-(hydroxyacetyl)-1-piperazinyl]phenyl]-2-oxo-5-oxazolidinyl]methyl]-2-cyclobutyl ethanethioamide | R = CH$_2$—cyclobutyl |
| 101 | (S)-N-[[3-[3-Fluoro-4-(hydroxyacetyl)-1-piperazinyl]phenyl]-2-oxo-5-oxazolidinyl]methyl]-2-cyclopentylethanethioamide | R = CH$_2$—cyclopentyl |

EXAMPLE 102

(S)-N-[[3-[3-Fluoro-4-[4-(hydroxyacetyl)-1-piperazinyl]phenyl]-2oxo-5-oxazolidinyl]methyl]-1-azetidinecarbothioamide

EXAMPLE 103

(S)-N-[[3-Fluoro-4-(4-acetyl-1-piperazinyl)phenyl]-2-oxo-5-oxazolidinyl]methyl]thioacetamide

TABLE G

| Example No. | Product | Amine | Dithio Compound |
|---|---|---|---|
| 104 | (S)-N-[[3-[3-Fluoro-4-(4-acetyl-1-piperazinyl)phenyl]-2-oxo-5-oxazolidinyl]methyl]propanethioamide; mp 161–162° C.; Anal. calcd for $C_{19}H_{25}FN_4O_3S$: C, 55.87; H, 6.17; N, 13.72; S, 7.85. Found: C, 55.79; H, 6.26; N, 13.60; S, 7.71 | P-90 | Z (a) |
| 105 | (S)-N-[[3-[3-Fluoro-4-(4-acetyl-1-piperazinyl)phenyl]-2-oxo-5-oxazolidinyl]methyl]-2-methylpropane-thioamide | P-90 | Z (b) |
| 106 | (S)-N-[[3-[3-Fluoro-4-(4-acetyl-1-piperazinyl)phenyl]-2-oxo-5-oxazolidinyl]methyl]cyclopropanecarbo-thioamide; mp 159–160° C.; Anal. calcd for $C_{20}H_{25}FN_4O_3S$: C, 57.13; H, 5.99; N, 13.32; S, 7.62. Found: C, 57.05; H, 6.01; N, 13.15; S, 7.45. | P-90 | Z (c) |
| 107 | (S)-N-[[3-[3-Fluoro-4-(4-acetyl-1-piperazinyl)phenyl]-2-oxo-5-oxazolidinyl]methyl]butanethioamide | P-90 | Z (d) |
| 108 | (S)-N-[[3-[3-Fluoro-4-(4-acetyl-1-piperazinyl)phenyl]-2-oxo-5-oxazolidinyl]methyl]-3-methylbutanethioamide | P-90 | Z (e) |
| 109 | (S)-N-[[3-[3-Fluoro-4-(4-acetyl-1-piperazinyl)phenyl]-2-oxo-5-oxazolidinyl]methyl]-2-methylbutane-thioamide | P-90 | Z (f) |
| 110 | (S)-N-[[3-[3-Fluoro-4-(4-acetyl-1-piperazinyl)phenyl]-2-oxo-5-oxazolidinyl]methyl]-3,3-dimethylbutane-thioamide | P-90 | Z (g) |
| 111 | (S)-N-[[3-[3-Fluoro-4-(4-acetyl-1-piperazinyl)phenyl]-2-oxo-5-oxazolidinyl]methyl]cyclobutanecarbo-thioamide | P-90 | Z (h) |
| 112 | (S)-N-[[3-[3-Fluoro-4-(4-acetyl-1-piperazinyl)phenyl]-2-oxo-5-oxazolidinyl]methyl]cyclopentanecarbo-thioamide | P-90 | Z (i) |
| 113 | (S)-N-[[3-[3-Fluoro-4-(4-acetyl-1-piperazinyl)phenyl]-2-oxo-5-oxazolidinyl]methyl]cyclohexanecarbo-thioamide | P-90 | Z (j) |
| 114 | (S)-N-[[3-[3-Fluoro-4-(4-acetyl-1-piperazinyl)phenyl]-2-oxo-5-oxazolidinyl]methyl]-2-cyclopropylethane-thioamide | P-90 | Z (k) |
| 115 | (S)-N-[[3-[3-Fluoro-4-(4-acetyl-1-piperazinyl)phenyl]-2-oxo-5-oxazolidinyl]methyl]-2-cyclobutylethane-thioamide | P-90 | Z (l) |
| 116 | (S)-N-[[3-[3-Fluoro-4-(4-acetyl-1-piperazinyl)phenyl]-2-oxo-5-oxazolidinyl]methyl]-2-cyclopentylethane-thioamide | P-90 | Z (m) |
| 117 | (S)-N-[[3-[3,5-Difluoro-4-(4-acetyl-1-piperazinyl)-phenyl]-2-oxo-5-oxazolidinyl]methyl]thioacetamide | P-91 | Ethyl dithio-acetate |
| 118 | (S)-N-[[3-[3,5-Difluoro-4-(4-acetyl-1-piperazinyl)-phenyl]-2-oxo-5-oxazolidinyl]methyl]propane-thioamide | P-91 | Z (a) |
| 119 | (S)-N-[[3-[3,5-Difluoro-4-(4-acetyl-1-piperazinyl)-phenyl]-2-oxo-5-oxazolidinyl]methyl]-2-methyl-propanethioamide | P-91 | Z (b) |
| 120 | (S)-N-[[3-[3, 5-Difluoro-4-(4-acetyl-1-piperazinyl)-phenyl]-2-oxo-5-oxazolidinyl]methyl]cyproane-carbothioamide | P-91 | Z (c) |
| 121 | (S)-N-[[3-[4-(4-Acetyl-1-piperazinyl)-2-oxo-5-oxazolidinyl]methyl]thioacetamide | P-92 | Ethyl dithio-acetate |

TABLE G-continued

| | | | |
|---|---|---|---|
| 122 | (S)-N-[[3-[4-(4-Acetyl-1-piperazinyl)-2-oxo-5-oxazolidinyl]methyl]propanethioamide | P-92 | Z (a) |
| 123 | (S)-N-[[3-[4-(4-Acetyl-1-piperazinyl)-2-oxo-5-oxazolidinyl]methyl]-2-methylpropanethioamide | P-92 | Z (b) |
| 124 | (S)-N-[[3-[4-(4-Acetyl-1-piperazinyl)-2-oxo-5-oxazolidinyl]methyl]cyclopropane-carbothioamide | P-92 | Z (c) |
| 125 | (S)-N-[[3-[3-Fluoro-4-[4-(methoxyacetyl)-1-piperazinyl]phenyl]-2-oxo-5-oxazolidinyl]methyl]-thioacetamide | P-93 | Ethyl dithio-acetate |
| 126 | (S)-N-[[3-[3-Fluoro-4-[4-(methoxyacetyl)-1-piperazinyl]phenyl]-2-oxo-5-oxazolidinyl]methyl]-propanethioamide | P-93 | Z (a) |
| 127 | (S)-N-[[3-[3-Fluoro-4-[4-(methoxyacetyl)-1-piperazinyl]phenyl]-2-oxo-5-oxazolidinyl]methyl]-propanethioamide | P-93 | Z (b) |
| 128 | (S)-N-[[3-[3-Fluoro-4-[4-(methoxyacetyl)-1-piperazinyl]phenyl]-2-oxo-5-oxazolidinyl]methyl]-methylpropanethioamide | P-93 | Z (c) |
| 129 | (S)-N-[[3-[3-Fluoro-4-[4-(methoxyacetyl)-1-piperazinyl]phenyl]-2-oxo-5-oxazolidinyl]methyl]-butanethioamide | P-93 | Z (d) |
| 130 | (S)-N-[[3-[3-Fluoro-4-[4-(methoxyacetyl)-1-(methoxyacetyl)-1-piperazinyl]phenyl]-2-oxo-5-oxazolidinyl]methyl]-3-methylbutanethioamide | P-93 | Z (e) |
| 131 | (S)-N-[[3-[3-Fluoro-4-[4-(methoxyacetyl)-1-piperazinyl]phenyl]-2-oxo-5-oxazolidinyl]methyl]-2-methylbutanethioamide | P-93 | Z (f) |
| 132 | (S)-N-[[3-[3-Fluoro-4-[4-(methoxyacetyl)-1-piperazinyl]phenyl]-2-oxo-5-oxazolidinyl]methyl]-3,3-dimethylbutanethioamide | P-93 | Z (g) |
| 133 | (S)-N-[[3-[3-Fluoro-4-[4-(methoxyacetyl)-1-piperazinyl]phenyl]-2-oxo-5-oxazolidinyl]methyl]-cyclobutanecarbothioamide | P-93 | Z (h) |
| 134 | (S)-N-[[3-[3-Fluoro-4-[4-(methoxyacetyl)-1-piperazinyl]phenyl]-2-oxo-5-oxazolidinyl]methyl]-cyclopentanecarbothioamide | P-93 | Z (i) |
| 135 | (S)-N-[[3-[3-Fluoro-4-[4-(methoxyacetyl)-1-piperazinyl]phenyl]-2-oxo-5-oxazolidinyl]methyl]-cyclohexanecarbothioamide | P-93 | Z (j) |
| 136 | (S)-N-[[3-[3-Fluoro-4-[4-(methoxyacetyl)-1-piperazinyl]phenyl]-2-oxo-5-oxazolidinyl]methyl]-2-cyclopropylethanethioamide | P-93 | Z (k) |
| 137 | (S)-N-[[3-[3-Fluoro-4-[4-(methoxyacetyl)-1-piperazinyl]phenyl]-2-oxo-5-oxazolidinyl]methyl]-2-cyclobutylethanethioamide | P-93 | Z (l) |

TABLE G-continued

| | | | |
|---|---|---|---|
| 138 | (S)-N-[[3-[3-Fluoro-4-[4-(methoxyacetyl)-1-piperazinyl]phenyl]-2-oxo-5-oxazolidinyl]methyl]-2-cyclopentylethanethioamide | P-93 | Z (m) |
| 139 | (S)-N-[[3-[3,5-Difluoro-[4-[4-(methoxyacetyl)-1-piperazinyl]phenyl]-2-oxo-5-oxazolidinyl]methyl]-thioacetamide | P-94 | Ethyl dithio-acetate |
| 140 | (S)-N-[[3-[3,5-Difluoro-[4-[4-(methoxyacetyl)-1-piperazinyl]phenyl]-2-oxo-5-oxazolidinyl]methyl]-propanethioamide | P-94 | Z (a) |
| 141 | (S)-N-[[3-[3, 5-Difluoro-[4-[4-(methoxyacetyl)-1-piperazinyl]phenyl]-2-oxo-5-oxazolidinyl]methyl]-2-methylpropanethioamide | P-94 | Z (b) |
| 142 | (S)-N-[[3-[3,5-Difluoro-[4-[4-(methoxyacetyl)-1-piperazinyl]phenyl]-2-oxo-5-oxazolidinyl]methyl]-cyclopropanecarbothioamide | P-94 | Z (c) |
| 143 | (S)-N-[[3-[4-[4-(methoxyacetyl)-1-piperazinyl]phenyl]-2-oxo-5-oxazolidinyl]methyl]thioacetamide | P-95 | Ethyl dithio-acetate |
| 144 | (S)-N-[[3-[4-[4-(methoxyacetyl)-1-piperazinyl]phenyl]-2-oxo-5-oxazolidinyl]methyl]propanethioamide | P-95 | Z (a) |
| 145 | (S)-N-[[3-[4-[4-(methoxyacetyl)-1-piperazinyl]phenyl]-2-oxo-5-oxazolidinyl]methyl]-2-methylpropane-thioamide | P-95 | Z (b) |
| 146 | (S)-N-[[3-[4-[4-(methoxyacetyl)-1-piperazinyl]phenyl]-2-oxo-5-oxazolidinyl]methyl]cyclopropanecarbothioamide | P-95 | Z (c) |
| 147 | (S)-N-[[3-[3-Fluoro-4-[4-(cyanoacetyl)-1-piperazinyl]-phenyl]-2-oxo-5-oxazolidinyl]methyl]thioacetamide | P-96 | Ethyl dithio-acetate |
| 148 | (S)-N-[[3-[3-Fluoro-4-[4-(cyanoacetyl)-1-piperazinyl]-phenyl]-2-oxo-5-oxazolidinyl]methyl]propanethioamide | P-96 | Z (a) |
| 149 | (S)-N-[[3-[3-Fluoro-4-(cyanoacetyl)-1-piperazinyl]-phenyl]-2-oxo-5-oxazolidinyl]methyl]-2-methyl-propanethioamide | P-96 | Z (a) |
| 150 | (S)-N-[[3-[3-Fluoro-4-(cyanoacetyl)-1-piperazinyl]-phenyl]-2-oxo-5-oxazolidinyl]methyl]cyclopropane-carbothioamide | P-96 | Z (b) |
| 151 | (S)-N-[[3-[3,5-Difluoro-4-[4-(cyanoacetyl)-1-piperazinyl]phenyl]-2-oxo-5-oxazolidinyl]-methyl]thioacetamide | P-97 | Ethyl dithio-acetate |
| 152 | (S)-N-[[3-[3,5-Difluoro-4-[4-(cyanoacetyl)-1-piperazinyl]phenyl]-2-oxo-5-oxazolidinyl]-methyl]propanethioamide | P-97 | Z (a) |
| 153 | (S)-N-[[3-[3,5-Difluoro-4-[4-(cyanoacetyl)-1-piperazinyl]phenyl]-2-oxo-5-oxazolidinyl]methyl]-2-methylpropanethioamide | P-97 | Z (b) |
| 154 | (S)-N-[[3-[3,5-Difluoro-4-[4-(cyanoacetyl)-1-piperazinyl]phenyl]-2-oxo-5-oxazolidinyl]-methyl]cyclopropanecarbothioamide | P-97 | Z (c) |
| 155 | (S)-N-[[3-[4-[4-(Cyanoacetyl)-1-piperazinyl]phenyl]-2-oxo-5-oxazolidinyl]mazinyl]phenyl]-2-oxo-5-oxazolidinyl]methyl]thioacetamide | P-98 | Ethyl dithio-dithio-acetate |

TABLE G-continued

| | | | |
|---|---|---|---|
| 156 | (S)-N-[[3-[4-[4-(Cyanoacetyl)-1-piperazinyl]phenyl]-2-oxo-5-oxazolidinyl]methyl]propanethioamide | P-98 | Z (a) |
| 157 | (S)-N-[[3-[4-[4-(Cyanoacetyl)-1-piperazinyl]phenyl]-2-oxo-5-oxazolidinyl]methyl]-2-methylpropanethioamide | P-98 | Z (b) |
| 158 | (S)-N-[[3-[4-[4-(Cyanoacetyl)-1-piperazinyl]phenyl]-2-oxo-5-oxazolidinyl]methyl]cycopropanecarbothioamide | P-98 | Z (c) |
| 159 | (S)-N-[[3-[3-Fluoro-4-[4-(acetoxyacetyl)-1-piperazinyl]phenyl]-2-oxo-5-oxazolidinyl]methyl]-thioacetamide | P-99 | Ethyl dithio-acetate |
| 160 | (S)-N-[[3-[3-Fluoro-4-[4-(acetoxyacetyl)-1-piperazinyl]phenyl]-2-oxo-5-oxazolidinyl]methyl]-propanethioamide | P-99 | Z (a) |
| 161 | (S)-N-[[3-[3-Fluoro-4-[4-(acetoxyacetyl)-1-piperazinyl]phenyl]-2-oxo-5-oxazolidinyl]methyl]-2-methylpropanethioamide | P-99 | Z (b) |
| 162 | (S)-N-[[3-[3-Fluoro-4-[4-(acetoxyacetyl)-1-piperazinyl]phenyl]-2-oxo-5-oxazolidinyl]methyl]-cyclopropanecarbothioamide | P-99 | Z (c) |
| 163 | (S)-N-[[3-[3-Fluoro-4-[4-(acetoxyacetyl)-1-piperazinyl]phenyl]-2-oxo-5-oxazolidinyl]methyl]-butanethioamide | P-99 | Z (d) |
| 164 | (S)-N-[[3-[3-Fluoro-4-[4-(acetoxyacetyl)-1-piperazinyl]phenyl]-2-oxo-5-oxazolidinyl]methyl]-3-methylbutanethioamide | P-99 | Z (e) |
| 165 | (S)-N-[[3-[3-Fluoro-4-[4-(acetoxyacetyl)-1-piperazinyl]phenyl]-2-oxo-5-oxazolidinyl]methyl]-2-methylbutanethioamide | P-99 | Z (f) |
| 166 | (S)-N-[[3-[3-Fluoro-4-[4-(acetoxyacetyl)-1-piperazinyl]phenyl]-2-oxo-5-oxazolidinyl]methyl]-3,3-dimethylbutanethioamide | P-99 | Z (g) |
| 167 | (S)-N-[[3-[3-Fluoro-4-[4-(acetoxyacetyl)-1-piperazinyl]phenyl]-2-oxo-5-oxazolidinyl]methyl]-cyclobutanecarbothioamide | P-99 | Z (h) |
| 168 | (S)-N-[[3-[3-Fluoro-4-[4-(acetoxyacetyl)-1-piperazinyl]phenyl]-2-oxo-5-oxazolidinyl]methyl]-cyclopentanecarbothioamide | P-99 | Z (i) |
| 169 | (S)-N-[[3-[3-Fluoro-4-[4-(acetoxyacetyl)-1-piperazinyl]phenyl]-2-oxo-5-oxazolidinyl]methyl]-cyclohexanecarbothioamide | P-99 | Z (j) |
| 170 | (S)-N-[[3-[3-Fluoro-4-[4-(acetoxyacetyl)-1-piperazinyl]phenyl]-2-oxo-5-oxazolidinyl]methyl]-2-cyclopropylethanethioamide | P-99 | Z (k) |
| 171 | (S)-N-[[3-[3-Fluoro-4-[4-(acetoxyacetyl)-1-piperazinyl]phenyl]-2-oxo-5-oxazolidinyl]methyl]-2-cyclobutylethanethioamide | P-99 | Z (l) |
| 172 | (S)-N-[[3-[3-Fluoro-4-[4-(acetoxyacetyl)-1-piperazinyl]phenyl]-2-oxo-5-oxazolidinyl]methyl]-2-cyclopentylethanethioamide | P-99 | Z (m) |

TABLE G-continued

| | | | |
|---|---|---|---|
| 173 | (S)-N-[[3-[3,5-Difluoro-4-[4-(acetoxyacetyl)-1-piperazinyl]phenyl]-2-oxo-5-oxazolidinyl]methyl]-thioacetamide | P-100 | Ethyl dithio-acetate |
| 174 | (S)-N-[[3-[3,5-Difluoro-4-[4-(acetoxyacetyl)-1-piperazinyl]phenyl]-2-oxo-5-oxazolidinyl]methyl]-propanethioamide | P-100 | Z (a) |
| 175 | (S)-N-[[3-[3,5-Difluoro-4-[4-(acetoxyacetyl)-1-piperazinyl]phenyl]-2-oxo-5-oxazolidinyl]methyl]-2-methylpropanethioamide | P-100 | Z (b) |
| 176 | (S)-N-[[3-[3,5-Difluoro-4-[4-(acetoxyacetyl)-1-piperazinyl]phenyl]-2-oxo-5-oxazolidinyl]methyl]-cyclopropanecarbothioamide | P-100 | Z (c) |
| 177 | (S)-N-[[3-[4-[4-(Acetoxyacetyl)-1-piperazinyl]phenyl]-2-oxo-5-oxazolidinyl]methyl]thioacetamide | P-100 | Ethyl dithio-acetate |
| 178 | (S)-N-[[3-[4-[4-(Acetoxyacetyl)-1-piperazinyl]phenyl]-2-oxo-5-oxazolidinyl]methyl]propanethioamide | P-101 | Z (a) |
| 179 | (S)-N-[[3-[4-[4-(Acetoxyacetyl)-1-piperazinyl]phenyl]-2-oxo-5-oxazolidinyl]methyl]-2-methylpropane-thioamide | P-101 | Z (b) |
| 180 | (S)-N-[[3-[4-[4-(Acetoxyacetyl)-1-piperazinyl]phenyl]-2-oxo-5-oxazolidinyl]methyl] cyclopropanecarbo-thioamide | P-101 | Z (c) |
| 181 | (S)-N-[[3-[3-Fluoro-4-[4-(benzyloxyacetyl)-1-piperazinyl]phenyl]-2-oxo-5-oxazolidinyl]methyl]-thioacetamide | P-102 | Ethyl dithio-acetate |
| 182 | (S)-N-[[3-[3-Fluoro-4-[4-(benzyloxyacetyl)-1-piperazinyl]phenyl]-2-oxo-5-oxazolidinyl]methyl]-propanethioamide | P-102 | Z (a) |
| 183 | (S)-N-[[3-[3-Fluoro-4-[4-(benzyloxyacetyl)-1-piperazinyl]phenyl]-2-oxo-5-oxazolidinyl]methyl]-2-methylpropanethioamide | P-102 | Z (b) |
| 184 | (S)-N-[[3-[3-Fluoro-4-[4-(benzyloxyacetyl)-1-piperazinyl]phenyl]-2-oxo-5-oxazolidinyl]methyl]-cyclopropanecarbothioamide | P-102 | Z (c) |
| 185 | (S)-N-[[3-[3,5-Difluoro-4-[4-(benzyloxyacetyl)-1-piperazinyl]phenyl]-2-oxo-5-oxazolidinyl]methyl]-thioacetamide | P-103 | Ethyl dithio-acetate |
| 186 | (S)-N-[[3-[3,5-Difluoro-4-[4-(benzyloxyacetyl)-1-piperazinyl]phenyl]-2-oxo-5-oxazolidinyl]methyl]-propanethioamide | P-103 | Z (a) |
| 187 | (S)-N-[[3-[3,5-Difluoro-4-[4-(benzyloxyacetyl)-1-piperazinyl]phenyl]-2-oxo-5-oxazolidinyl]methyl]-2-methylpropanethioamide | P-103 | Z (b) |
| 188 | (S)-N-[[3-[3,5-Difluoro-4-[4-(benzyloxyacetyl)-1-piperazinyl]phenyl]-2-oxo-5-oxazolidinyl]methyl]-cyclopropanecarbothioamide | P-103 | Z (c) |
| 189 | (S)-N-[[3-[3-Fluoro-4-[4-(methoxycarbonyl)-1-piperazinyl]phenyl]-2-oxo-5-oxazolidinyl]methyl]-thioacetamide | P-105 | Ethyl dithio-acetate |

TABLE G-continued

| | | | |
|---|---|---|---|
| 190 | (S)-N-[[3-[3-Fluoro-4-[4-(methoxycarbonyl)-1-piperazinyl]phenyl]-2-oxo-5-oxazolidinyl]methyl]-propanethioamide | P-105 | Z (a) |
| 191 | (S)-N-[[3-[3-Fluoro-4-[4-(methoxycarbonyl)-1-piperazinyl]phenyl]-2-oxo-5-oxazolidinyl]methyl]-2-methylpropanethioamide | P-105 | Z (b) |
| 192 | (S)-N-[[3-[3-Fluoro-4-[4-(methoxycarbonyl)-1-piperazinyl]phenyl]-2-oxo-5-oxazolidinyl]methyl]-cyclopropanecarbothioamide | P-105 | Z (c) |
| 193 | (S)-N-[[3-[3-Fluoro-4-[4-(methoxycarbonyl)-1-piperazinyl]phenyl]-2-oxo-5-oxazolidinyl]methyl]-butanethioamide | P-105 | Z (d) |
| 194 | (S)-N-[[3-[3-Fluoro-4-[4-(methoxycarbonyl)-1-piperazinyl]phenyl]-2-oxo-5-oxazolidinyl]methyl]-3-methylbutanethioamide | P-105 | Z (e) |
| 195 | (S)-N-[[3-[3-Fluoro-4-[4-(methoxycarbonyl)-1-piperazinyl]phenyl]-2-oxo-5-oxazolidinyl]methyl]-2-methylbutanethioamide | P-105 | Z (f) |
| 196 | (S)-N-[[3-[3-Fluoro-4-[4-(methoxycarbonyl)-1-piperazinyl]phenyl]-2-oxo-5-oxazolidinyl]methyl]-3,3-dimethylbutanethioamide | P-105 | Z (g) |
| 197 | (S)-N-[[3-[3-Fluoro-4-[4-(methoxycarbonyl)-1-piperazinyl]phenyl]-2-oxo-5-oxazolidinyl]methyl]-cyclobutanecarbothioamide | P-105 | Z (h) |
| 198 | (S)-N-[[ 3-[3-Fluoro-4-[4-(methoxycarbonyl)-1-piperazinyl]phenyl]-2-oxo-5-oxazolidinyl]methyl]-cyclopentanecarbothioamide | P-105 | Z (i) |
| 199 | (S)-N-[[3-[3-Fluoro-4-[4-(methoxycarbonyl)-1-piperazinyl]phenyl]-2-oxo-5-oxazolidinyl]methyl]-cyclohexanecarbothioamide | P-105 | Z (j) |
| 200 | (S)-N-[[3-[3-Fluoro-4-[4-(methoxycarbonyl)-1-piperazinyl]phenyl]-2-oxo-5-oxazolidinyl]methyl]-2-cyclopropylethanethioamide | P-105 | Z (k) |
| 201 | (S)-N-[[3-[3-Fluoro-4-[4-(methoxycarbonyl)-1-piperazinyl]phenyl]-2-oxo-5-oxazolidinyl]methyl]-2-cyclobutylethanethioamide | P-105 | Z (l) |
| 202 | (S)-N-[[3-[3-Fluoro-4-[4-(methoxycarbonyl)-1-piperazinyl]phenyl]-2-oxo-5-oxazolidinyl]methyl]-2-cyclopentylethanethioamide | P-105 | Z (m) |
| 203 | (S)-N-[[3-[3,5-Difluoro-4-[4-(methoxycarbonyl)-1-piperazinyl]phenyl]-2-oxo-5-oxazolidinyl]methyl]-thioacetamide | P-106 | Ethyl dithio-acetate |
| 204 | (S)-N-[[3-[3,5-Difluoro-4-[4-(methoxycarbonyl)-1-piperazinyl]phenyl]-2-oxo-5-oxazolidinyl]methyl]-propanethioamide | P-106 | Z (a) |
| 205 | (S)-N-[[3-[3,5-Difluoro-4-[4-(methoxycarbonyl)-1-piperazinyl]phenyl]-2-oxo-5-oxazolidinyl]methyl]-2-methylpropanethioamide | P-106 | Z (b) |

TABLE G-continued

| | | | |
|---|---|---|---|
| 206 | (S)-N-[[3-[3,5-Difluoro-4-[4-(methoxycarbonyl)-1-piperazinyl]phenyl]-2-oxo-5-oxazolidinyl]methyl]-cyclopropanecarbothioamide | P-106 | Z (c) |
| 207 | (S)-N-[[3-[4-[4-(methoxycarbonyl)-1-piperazinyl]phenyl]-2-oxo-5-oxazolidinyl]methyl]-thioacetamide | P-107 | Ethyl dithio-acetate |
| 208 | (S)-N-[[3-[4-[4-(methoxycarbonyl)-1-piperazinyl]phenyl]-2-oxo-5-oxazolidinyl]methyl]-propanethioamide | P-107 | Z (a) |
| 209 | (S)-N-[[3-[4-[4-(methoxycarbonyl)-1-piperazinyl]phenyl]-2-oxo-5-oxazolidinyl]methyl]-2-methylpropanethioamide | P-107 | Z (b) |
| 210 | (S)-N-[[3-[4-[4-(methoxycarbonyl)-1-piperazinyl]phenyl]-2-oxo-5-oxazolidinyl]methyl]-cyclopropanecarbothioamide | P-107 | Z (c) |
| 211 | (S)-N-[[3-[3-Fluoro-4-[4-(methanesulfonyl)-1-piperazinyl]phenyl]-2-oxo-5-oxazolidinyl]methyl]-thioacetamide; mp 197–198° C.; Anal. calcd for $C_{17}H_{23}FN_4O_4S_2$: C, 47.43; H, 5.39; N, 13.01; S, 14.89. Found: C, 47.25; H, 5.40; N, 12.82; S, 14.56. | P-108 | Ethyl dithio-acetate |
| 212 | (S)-N-[[3-[3-Fluoro-4-[4-(methanesulfonyl)-1-piperazinyl]phenyl]-2-oxo-5-oxazolidinyl]methyl]-propanethioamide; mp 207–208° C.; Anal. calcd for $C_{18}H_{25}FN_4O_4S_2$: C, 48.63; H, 5.67; N, 12.60; S, 14.42. Found: C, 48.51; H, 5.59; N, 12.52; S, 14.09. | P-108 | Z (a) |
| 213 | (S)-N-[[3-[3-Fluoro-4-[4-(methanesulfonyl)-1-piperazinyl]phenyl]-2-oxo-5-oxazolidinyl]methyl]-2-methylpropanethioamide; mp 204–206° C.; Anal. calcd for $C_{19}H_{27}FN_4O_4S_2$: C, 49.76; H, 5.93; N, 12.22; S, 13.98. Found: C, 49.63; H, 5.92; N, 14.14; S, 13.91. | P-108 | Z (b) |
| 214 | (S)-N-[[3-[3-Fluoro-4-[4-(methanesulfonyl)-1-piperazinyl]phenyl]-2-oxo-5-oxazolidinyl]methyl]-cyclopropanecarbothioamide; Anal. calcd for $C_{19}H_{25}FN_4O_4S_2$: C, 49.98; H, 5.52; N, 12.27; S, 14.04. Found: C, 49.42; H, 5.50; N, 12.08; S, 13.80. | P-108 | Z (a) |
| 215 | (S)-N-[[3-[3,5-Difluoro-4-[4-(methanesulfonyl)-1-piperazinyl]phenyl]-2-oxo-5-oxazolidinyl]methyl]-thioacetamide | P-109 | Ethyl dithio-acetate |
| 216 | (S)-N-[[3-[3,5-Difluoro-4-[4-(methanesulfonyl)-1-piperazinyl]phenyl]-2-oxo-5-oxazolidinyl]methyl]-propanethioamide | | |
| 217 | (S)-N-[[3-[3,5-Difluoro-4-[4-(methanesulfonyl)-1-piperazinyl]phenyl]-2-oxo-5-oxazolidinyl]methyl]-2-methylpropanethioamide | | |
| 218 | (S)-N-[[3-[3,5-Difluoro-4-[4-(methanesulfonyl)-1-piperazinyl]phenyl]-2-oxo-5-oxazolidinyl]methyl]-cyclopropanecarbothioamide | | |

TABLE G-continued

| | | | |
|---|---|---|---|
| 219 | (S)-N-[[3-[4-[4-(methanesulfonyl)-1-piperazinyl]phenyl]-2-oxo-5-oxazolidinyl]methyl]-thioacetamide | | |
| 220 | (S)-N-[[3-[4-[4-(methanesulfonyl)-1-piperazinyl]phenyl]-2-oxo-5-oxazolidinyl]methyl]-propanethioamide | | |
| 221 | (S)-N-[[3-[4-[4-(methanesulfonyl)-1-piperazinyl]phenyl]-2-oxo-5-oxazolidinyl]methyl]-2-methylpropanethioamide | | |
| 222 | (S)-N-[[3-[4-[4-(methanesulfonyl)-1-piperazinyl]phenyl]-2-oxo-5-oxazolidinyl]methyl]-cyclopropanecarbothioamide | | |
| 223 | (S)-N-[[3-[3-Fluoro-4-[4-(ethanesulfonyl)-1-piperazinyl]phenyl]-2-oxo-5-oxazolidinyl]methyl]-thioacetamide | | |
| 224 | (S)-N-[[3-[3-Fluoro-4-[4-(ethanesulfonyl)-1-piperazinyl]phenyl]-2-oxo-5-oxazolidinyl]methyl]-propanethioamide | | |
| 225 | (S)-N-[[3-[3-Fluoro-4-[4-(ethanesulfonyl)-1-piperazinyl]phenyl]-2-oxo-5-oxazolidinyl]methyl]-2-methylpropanethioamide | P-111 | |
| 226 | (S)-N-[[3-[3-Fluoro-4-[4-(ethanesulfonyl)-1-piperazinyl]phenyl]-2-oxo-5-oxazolidinyl]methyl]-cyclopropanecarbothioamide | P-111 | |
| 227 | (S)-N-[[3-[3,5-Difluoro-4-[4-(ethanesulfonyl)-1-piperazinyl]phenyl]-2-oxo-5-oxazolidinyl]methyl]-thioacetamide | P-112 | |
| 228 | (S)-N-[[3-[3,5-Difluoro-4-[4-(ethanesulfonyl)-1-piperazinyl]phenyl]-2-oxo-5-oxazolidinyl]methyl]-propanethioamide | P-112 | |
| 229 | (S)-N-[[3-[3,5-Difluoro-4-[4-(ethanesulfonyl)-1-piperazinyl]phenyl]-2-oxo-5-oxazolidinyl]methyl]-2-methylpropanethioamide | P-112 | |
| 230 | (S)-N-[[3-[3,5-Difluoro-4-[4-(ethanesulfonyl)-1-piperazinyl]phenyl]-2-oxo-5-oxazolidinyl]methyl]-cyclopropanecarbothioamide | P-112 | |
| 231 | (S)-N-[[3-[4-[4-(ethanesulfonyl)-1-piperazinyl]phenyl]-2-oxo-5-oxazolidinyl]methyl]thioacetamide | P-113 | |
| 232 | (S)-N-[[3-[4-[4-(ethanesulfonyl)-1-piperazinyl]phenyl]-2-oxo-5-oxazolidinyl]methyl]propanethioamide | P-113 | |
| 233 | (S)-N-[[3-[4-[4-(ethanesulfonyl)-1-piperazinyl]phenyl]-2-oxo-5-oxazolidinyl]methyl]-2-methylpropane-thioamide | P-113 | |
| 234 | (S)-N-[[3-[4-[4-(ethanesulfonyl)-1-piperazinyl]phenyl]-2-oxo-5-oxazolidinyl]methyl] cyclopropanecarbothioamide | P-113 | Z (c) |
| 235 | (S)-N-[[3-[3-Fluoro-4-[4-(chloromethanesulfonyl)-1-piperazinyl]phenyl]-2-oxo-5-oxazolidinyl]methyl]-thioacetamide | P-114 | Ethyl dithio-acetate |

TABLE G-continued

| | | | |
|---|---|---|---|
| 236 | (S)-N-[[3-[3-Fluoro-4-[4-(chloromethanesulfonyl)-1-piperazinyl]phenyl]-2-oxo-5-oxazolidinyl]methyl]-propanethioamide | P-114 | Z (a) |
| 237 | (S)-N-[[3-[3-Fluoro-4-[4-(chloromethanesulfonyl)-1-piperazinyl]phenyl]-2-oxo-5-oxazolidinyl]methyl]-2-methylpropanethioamide | P-114 | Z (b) |
| 238 | (S)-N-[[3-[3-Fluoro-4-[4-(chloromethanesulfonyl)-1-piperazinyl]phenyl]-2-oxo-5-oxazolidinyl]methyl]-cyclopropanecarbothioamide | P-114 | Z (c) |
| 239 | (S)-N-[[3-[3,5-Difluoro-4-[4-(chloromethanesulfonyl)-1-piperazinyl]phenyl]-2-oxo-5-oxazolidinyl]methyl]-thioacetamide | P-115 | Ethyl dithio-acetate |
| 240 | (S)-N-[[3-[3,5-Difluoro-4-[4-(chloromethanesulfonyl)-1-piperazinyl]phenyl]-2-oxo-5-oxazolidinyl]methyl]propanethioamide | P-115 | Z (a) |
| 241 | (S)-N-[[3-[3,5-Difluoro-4-[4-(chloromethanesulfonyl)-1-piperazinyl]phenyl]-2-oxo-5-oxazolidinyl]methyl]-2-methylpropanethioamide | P-115 | Z (b) |
| 242 | (S)-N-[[3-[3,5-Difluoro-4-[4-(chloromethanesulfonyl)-1-piperazinyl]phenyl]-2-oxo-5-oxazolidinyl]methyl]-cyclopropanecarbothioamide | P-115 | Z (c) |
| 243 | (S)-N-[[3-[4-[4-(chloromethanesulfonyl)-1-piperazinyl]phenyl]-2-oxo-5-oxazolidinyl]methyl]-thioacetamide | P-116 | Ethyl dithio-acetate |
| 244 | (S)-N-[[3-[4-[4-(chloromethanesulfonyl)-1-piperazinyl]phenyl]-2-oxo-5-oxazolidinyl]methyl]-propanethioamide | P-116 | Z (a) |
| 245 | (S)-N-[[3-[4-[4-(chloromethanesulfonyl)-1-piperazinyl]phenyl]-2-oxo-5-oxazolidinyl]methyl]-2-methylpropanethioamide | P-116 | Z (b) |
| 246 | (S)-N-[[3-[4-[4-(chloromethanesulfonyl)-1-piperazinyl]phenyl]-2-oxo-5-oxazolidinyl]methyl]-cyclopropanecarbothioamide | P-116 | Z (c) |
| 247 | (S)-N-[[3-[3-Fluoro-4-[4-(cyanomethane-sulfonyl)-1-piperazinyl]phenyl]-2-oxo-5-oxazolidinyl]methyl]thioacetamide | P-117 | Ethyl dithio-acetate |
| 248 | (S)-N-[[3-[3-Fluoro-4-[4-(cyanomethane-sulfonyl)-1-piperazinyl]phenyl]-2-oxo-5-oxazolidinyl]methyl]-propanethioamide | P-117 | Z (a) |
| 249 | (S)-N-[[3-[3-Fluoro-4-[4-(cyanomethane-sulfonyl)-1-piperazinyl]phenyl]-2-oxo-5-oxazolidinyl]methyl]-2-methylpropanethioamide | P-117 | Z (b) |
| 250 | (S)-N-[[3-[3-Fluoro-4-[4-(cyanomethane-sulfonyl)-1-piperazinyl]phenyl]-2-oxo-5-oxazolidinyl]methyl]-cyclopropanecarbothioamide | P-117 | Z (c) |
| 251 | (S)-N-[[3-[3,5-Difluoro-4-[4-(cyanomethane-sulfonyl)-1-piperazinyl]phenyl]-2-oxo-5-oxazolidinyl]methyl]thioacetamide | | Ethyl dithio-acetate |

TABLE G-continued

| | | | |
|---|---|---|---|
| 252 | (S)-N-[[3-[3,5-Difluoro-4-[4-(cyanomethane-sulfonyl)-1-piperazinyl]phenyl]-2-oxo-5-oxazolidinyl]methyl]propanethioamide | P-118 | Z (a) |
| 253 | (S)-N-[[3-[3,5-Difluoro-4-[4-(cyanomethane-sulfonyl)-1-piperazinyl]phenyl]-2-oxo-5-oxazolidinyl]methyl]-2-methylpropanethioamide | P-118 | Z (b) |
| 254 | (S)-N-[[3-[3,5-Difluoro-4-[4-(cyanomethane-sulfonyl)-1-piperazinyl]phenyl]-2-oxo-5-oxazolidinyl]methyl]cyclopropanecarbothioamide | P-118 | Z (c) |
| 255 | (S)-N-[[3-[4-[4-(Cyanomethanesulfonyl)-1-piperazinyl]phenyl]-2-oxo-5-oxazolidinyl]methyl]thioacetamide | P-119 | Ethyl dithioacetate |
| 256 | (S)-N-[[3-[4-[4-(Cyanomethanesulfonyl)-1-piperazinyl]phenyl]-2-oxo-5-oxazolidinyl]methyl]propanethioamide | P-119 | Z (a) |
| 257 | (S)-N-[[3-[4-[4-(Cyanomethanesulfonyl)-1-piperazinyl]phenyl]-2-oxo-5-oxazolidinyl]methyl]-2-methylpropanethioamide | P-119 | Z (b) |
| 258 | (S)-N-[[3-[4-[4-(Cyanomethanesulfonyl)-1-piperazinyl]phenyl]-2-oxo-5-oxazolidinyl]methyl]cyclopropanecarbothioamide | P-119 | Z (c) |
| 259 | (S)-N-[[3-[3-Fluoro-4-[4-(N-methylsulfamoyl)-1-piperazinyl]phenyl]-2-oxo-5-oxazolidinyl]methyl]thioacetamide | P-120 | Ethyl dithioacetate |
| 260 | (S)-N-[[3-[3-Fluoro-4-[4-(N-methylsulfamoyl)-1-piperazinyl]phenyl]-2-oxo-5-oxazolidinyl]methyl]propanethioamide | P-120 | Z (a) |
| 261 | (S)-N-[[3-[3-Fluoro-4-[4-(N-methylsulfamoyl)-1-piperazinyl]phenyl]-2-oxo-5-oxazolidinyl]methyl]-2-methylpropanethioamide | P-120 | Z (b) |
| 262 | (S)-N-[[3-[3-Fluoro-4-[4-(N-methylsulfamoyl)-1-piperazinyl]phenyl]-2-oxo-5-oxazolidinyl]methyl]cyclopropanecarbothioamide | P-120 | Z (c) |
| 263 | (S)-N-[[3-[3,5-Difluoro-4-[4-(N-methylsulfamoyl)-1-piperazinyl]phenyl]-2-oxo-5-oxazolidinyl]methyl]thioacetamide | P-121 | Ethyl dithioacetate |
| 264 | (S)-N-[[3-[3,5-Difluoro-4-[4-(N-methylsulfamoyl)-1-piperazinyl]phenyl]-2-oxo-5-oxazolidinyl]methyl]propanethioamide | P-121 | Z (a) |
| 265 | (S)-N-[[3-[3,5-Difluoro-4-[4-(N-methylsulfamoyl)-1-piperazinyl]phenyl]-2-oxo-5-oxazolidinyl]methyl]-2-methylpropanethioamide | P-121 | Z (b) |
| 266 | (S)-N-[[3-[3,5-Difluoro-4-[4-(N-methylsulfamoyl)-1-piperazinyl]phenyl]-2-oxo-5-oxazolidinyl]methyl]cyclopropanecarbothioamide | P-121 | Z (c) |
| 267 | (S)-N-[[3-[4-[4-(N-methylsulfamoyl)-1-piperazinyl]phenyl]-2-oxo-5-oxazolidinyl]methyl]thioacetamide | P-122 | Ethyl dithioacetate |

TABLE G-continued

| | | | |
|---|---|---|---|
| 268 | (S)-N-[[3-[4-[4-(N-methylsulfamoyl)-1-piperazinyl]phenyl]-2-oxo-5-oxazolidinyl]methyl]-propanethioamide | P-122 | Z (a) |
| 269 | (S)-N-[[3-[4-[4-(N-methylsulfamoyl)-1-piperazinyl]phenyl]-2-oxo-5-oxazolidinyl]methyl]-2-methylpropanethioamide | P-122 | Z (b) |
| 270 | (S)-N-[[3-[4-[4-(N-methylsulfamoyl)-1-piperazinyl]phenyl]-2-oxo-5-oxazolidinyl]methyl]-cyclopropanecarbothioamide | P-122 | Z (c) |
| 271 | (S)-N-[[3-[3-Fluoro-4-[4-(N,N-dimethylsulfamoyl)-1-piperazinyl]phenyl]-2-oxo-5-oxazolidinyl]methyl]-thioacetamide | P-123 | Ethyl dithio-acetate |
| 272 | (S)-N-[[3-[3-Fluoro-4-[4-(N,N-dimethylsulfamoyl)-1-piperazinyl]phenyl]-2-oxo-5-oxazolidinyl]methyl]-propanethioamide | P-123 | Z (a) |
| 273 | (S)-N-[[3-[3-Fluoro-4-[4-(N,N-dimethylsulfamoyl)-1-piperazinyl]phenyl]-2-oxo-5-oxazolidinyl]methyl]-2-methylpropanethioamide | P-123 | Z (b) |
| 274 | (S)-N-[[3-[3-Fluoro-4-[4-(N,N-dimethylsulfamoyl)-1-piperazinyl]phenyl]-2-oxo-5-oxazolidinyl]methyl]-cyclopropanecarbothioamide | P-123 | Z (c) |
| 275 | (S)-N-[[3-[3,5-Difluoro-4-[4-(N,N-dimethylsulfamoyl)-1-piperazinyl]phenyl]-2-oxo-5-oxazolidinyl]methyl]-thioacetamide | P-124 | Ethyl dithio-acetate |
| 276 | (S)-N-[[3-[3,5-Difluoro-4-[4-(N,N-dimethylsulfamoyl)-1-piperazinyl]phenyl]-2-oxo-5-oxazolidinyl]methyl]-propanethioamide | P-124 | Z (a) |
| 277 | (S)-N-[[3-[3,5-Difluoro-4-[4-(N,N-dimethylsulfamoyl)-1-piperazinyl]phenyl]-2-oxo-5-oxazolidinyl]methyl]-2-methylpropanethioamide | P-124 | Z (b) |
| 278 | (S)-N-[[3-[3,5-Difluoro-4-[4-(N,N-dimethylsulfamoyl)-1-piperazinyl]phenyl]-2-oxo-5-oxazolidinyl]methyl]-cyclopropanecarbothioamide | P-124 | Z (c) |
| 279 | (S)-N-[[3-[4-[4-(N,N-dimethylsulfamoyl)-1-piperazinyl]phenyl]-2-oxo-5-oxazolidinyl]methyl]-thioacetamide | P-125 | Ethyl dithio-acetate |
| 280 | (S)-N-[[3-[4-[4-(N,N-dimethylsulfamoyl)-1-piperazinyl]phenyl]-2-oxo-5-oxazolidinyl]methyl]-propanethioamide | P-125 | Z (a) |
| 281 | (S)-N-[[3-[4-[4-(N,N-dimethylsulfamoyl)-1-piperazinyl]phenyl]-2-oxo-5-oxazolidinyl]methyl]-2-methylpropanethioamide | P-125 | Z (b) |
| 282 | (S)-N-[[3-[4-[4-(N,N-dimethylsulfamoyl)-1-piperazinyl]phenyl]-2-oxo-5-oxazolidinyl]methyl]-cyclopropanecarbothioamide | P-125 | Z (c) |

TABLE G-continued

| | | | |
|---|---|---|---|
| 283 | (S)-N-[[3-[3-Fluoro-4-[4-(ethoxycarbonyl)-1-piperazinyl]phenyl]-2-oxo-5-oxazolidinyl]methyl]-thioacetamide | P-126 | Ethyl dithio-acetate |
| 284 | (S)-N-[[3-[3-Fluoro-4-[4-(ethoxycarbonyl)-1-piperazinyl]phenyl]-2-oxo-5-oxazolidinyl]methyl]-propanethioamide | P-126 | Z (a) |
| 285 | (S)-N-[[3-[3-Fluoro-4-[4-(ethoxycarbonyl)-1-piperazinyl]phenyl]-2-oxo-5-oxazolidinyl]methyl]-2-methylpropanethioamide | P-126 | Z (b) |
| 286 | (S)-N-[[3-[3-Fluoro-4-[4-(ethoxycarbonyl)-1-piperazinyl]phenyl]-2-oxo-5-oxazolidinyl]methyl]-cyclopropanecarbothioamide | P-126 | Z (c) |
| 287 | (S)-N-[[3-[3-Fluoro-4-[4-(ethoxycarbonyl)-1-piperazinyl]phenyl]-2-oxo-5-oxazolidinyl]methyl]-butanethioamide | P-126 | Z (d) |
| 288 | (S)-N-[[3-[3-Fluoro-4-[4-(ethoxycarbonyl)-1-piperazinyl]phenyl]-2-oxo-5-oxazolidinyl]methyl]-3-methylbutanethioamide | P-126 | Z (e) |
| 289 | (S)-N-[[3-[3-Fluoro-4-[4-(ethoxycarbonyl)-1-piperazinyl]phenyl]-2-oxo-5-oxazolidinyl]methyl]-2-methylbutanethioamide | P-126 | Z (f) |
| 290 | (S)-N-[[3-[3-Fluoro-4-[4-(ethoxycarbonyl)-1-piperazinyl]phenyl]-2-oxo-5-oxazolidinyl]methyl]-3,3-dimethylbutanethioamide | P-126 | Z (g) |
| 291 | (S)-N-[[3-[3-Fluoro-4-[4-(ethoxycarbonyl)-1-piperazinyl]phenyl]-2-oxo-5-oxazolidinyl]methyl]-cyclobutanecarbothioamide | P-126 | Z (h) |
| 292 | (S)-N-[[3-[3-Fluoro-4-[4-(ethoxycarbonyl)-1-piperazinyl]phenyl]-2-oxo-5-oxazolidinyl]methyl]-cyclopentanecarbothioamide | P-126 | Z (i) |
| 293 | (S)-N-[[3-[3-Fluoro-4-[4-(ethoxycarbonyl)-1-piperazinyl]phenyl]-2-oxo-5-oxazolidinyl]methyl]-cyclohexanecarbothioamide | P-126 | Z (j) |
| 294 | (S)-N-[[3-[3-Fluoro-4-[4-(ethoxycarbonyl)-1-piperazinyl]phenyl]-2-oxo-5-oxazolidinyl]methyl]-2-cyclopropylethanethioamide | P-126 | Z (k) |
| 295 | (S)-N-[[3-[3-Fluoro-4-[4-(ethoxycarbonyl)-1-piperazinyl]phenyl]-2-oxo-5-oxazolidinyl]methyl]-2-cyclobutylethanethioamide | P-126 | Z (l) |
| 296 | (S)-N-[[3-[3-Fluoro-4-[4-(ethoxycarbonyl)-1-piperazinyl]phenyl]-2-oxo-5-oxazolidinyl]methyl]-2-cyclopentylethanethioamide | P-126 | Z (m) |
| 297 | (S)-N-[[3-[3,5-Difluoro-4-[4-(ethoxycarbonyl)-1-piperazinyl]phenyl]-2-oxo-5-oxazolidinyl]methyl]-thioacetmide | P-127 | Ethyl dithio-acetate |

TABLE G-continued

| | | | |
|---|---|---|---|
| 298 | (S)-N-[[3-[3,5-Difluoro-4-[4-(ethoxycarbonyl)-1-piperazinyl]phenyl]-2-oxo-5-oxazolidinyl]methyl]-propanethioamide | P-127 | Z (a) |
| 299 | (S)-N-[[3-[3,5-Difluoro-4-[4-(ethoxycarbonyl)-1-piperazinyl]phenyl]-2-oxo-5-oxazolidinyl]methyl]-2-methylpropanethioamide | P-127 | Z (b) |
| 300 | (S)-N-[[3-[3,5-Difluoro-4-[4-(ethoxycarbonyl)-1-piperazinyl]phenyl]-2-oxo-5-oxazolidinyl]methyl]-cyclopropanecarbothioamide | P-127 | Z (c) |
| 301 | (S)-N-[[3-[4-[4-(ethoxycarbonyl)-1-piperazinyl]-phenyl]-2-oxo-5-oxazolidinyl]methyl]thioacetamide | P-127 | Ethyl dithio-acetate |
| 302 | (S)-N-[[3-[4-[4-(ethoxycarbonyl)-1-piperazinyl]-phenyl]-2-oxo-5-oxazolidinyl]methyl]-propanethioamide | P-128 | Z (a) |
| 303 | (S)-N-[[3-[4-[4-(ethoxycarbonyl)-1-piperazinyl]-phenyl]-2-oxo-5-oxazolidinyl]methyl]-2-methylpropanethioamide | P-128 | Z (b) |
| 304 | (S)-N-[[3-[4-[4-(ethoxycarbonyl)-1-piperazinyl]-phenyl]-2-oxo-5-oxazolidinyl]methyl]cyclopropane-carbothioamide | P-128 | Z (c) |
| 305 | (S)-N-[[3-[3-Fluoro-4-(4-sulfamoyl-1-piperazinyl)-phenyl]-2-oxo-5-oxazolidinyl]methyl]thioacetamide | P-129 | Ethyl dithio-acetate |
| 306 | (S)-N-[[3-[3-Fluoro-4-(4-sulfamoyl-1-piperazinyl)-phenyl]-2-oxo-5-oxazolidinyl]methyl]-propanethioamide | P-129 | Z (a) |
| 307 | (S)-N-[[3-[3-Fluoro-4-(4-sulfamoyl-1-piperazinyl)-phenyl]-2-oxo-5-oxazolidinyl]methyl]-2-methylpropanethioamide | P-129 | Z (b) |
| 308 | (S)-N-[[3-[3-Fluoro-4-(4-sulfamoyl-1-piperazinyl)-phenyl]-2-oxo-5-oxazolidinyl]methyl]-cyclopropanecarbothioamide | P-129 | Z (c) |
| 309 | (S)-N-[[3-[3-Fluoro-4-(4-sulfamoyl-1-piperazinyl)-phenyl]-2-oxo-5-oxazolidinyl]methyl]butanethioamide | P-129 | Z (d) |
| 310 | (S)-N-[[3-[3-Fluoro-4-(4-sulfamoyl-1-piperazinyl)phenyl]-2-oxo-5-oxazolidinyl]methyl]-3-methylbutanethioamide | P-129 | Z (e) |
| 311 | (S)-N-[[3-[3-Fluoro-4-(4-sulfamoyl-1-piperazinyl) phenyl]-2-oxo-5-oxazolidinyl] methyl]-2-methylbutanethioamide | P-129 | Z (f) |
| 312 | (S)-N-[[3-[3-Fluoro-4-(4-sulfamoyl-1-piperazinyl)phenyl]-2-oxo-5-oxazolidinyl]methyl]-3,3-dimethylbutanethioamide | P-129 | Z (g) |
| 313 | (S)-N-[[3-[3-Fluoro-4-(4-sulfamoyl-1-piperazinyl)phenyl]-2-oxo-5-oxazolidinyl]methyl]cyclobutanecarbothioamide | P-129 | Z (g) |
| 314 | (S)-N-[[3-[3-Fluoro-4-(4-sulfamoyl-1-piperazinyl)phenyl]-2-oxo-5-oxazolidinyl]methyl]cyclopentanecarbothioamide | P-129 | Z (i) |

TABLE G-continued

| | | | |
|---|---|---|---|
| 315 | (S)-N-[[3-[3-Fluoro-4-(4-sulfamoyl-1-piperazinyl)phenyl]-2-oxo-5-oxazolidinyl]methyl]cyclohexanecarbothioamide | P-129 | Z (j) |
| 316 | (S)-N-[[3-[3-Fluoro-4-(4-sulfamoyl-1-piperazinyl)phenyl]-2-oxo-5-oxazolidinyl]methyl]-2-cyclopropylethanethioamide | P-129 | Z (k) |
| 317 | (S)-N-[[3-[3-Fluoro-4-(4-sulfamoyl-1-piperazinyl)phenyl]-2-oxo-5-oxazolidinyl]methyl]-2-cyclobutylethanethioamide | P-129 | Z (l) |
| 318 | (S)-N-[[3-[3-Fluoro-4-(4-sulfamoyl-1-piperazinyl)phenyl]-2-oxo-5-oxazolidinyl]methyl]-2-cyclopentylethanethioamide | P-129 | Z (m) |
| 319 | (S)-N-[[3-[3,5-Difluoro-4-(4-sulfamoyl-1-piperazinyl)phenyl]-2-oxo-5-oxazolidinyl]methyl]thioacetamide | P-130 | Ethyl dithioacetate |
| 320 | (S)-N-[[3-[3,5-Difluoro-4-(4-sulfamoyl-1-piperazinyl)phenyl]-2-oxo-5-oxazolidinyl]methyl]propanethioamide | P-130 | Z (a) |
| 321 | (S)-N-[[3-[3,5-Difluoro-4-(4-sulfamoyl-1-piperazinyl)phenyl]-2-oxo-5-oxazolidinyl]methyl]-2-methylpropanethioamide | P-130 | Z (b) |
| 322 | (S)-N-[[3-[3,5-Difluoro-4-(4-sulfamoyl-1-piperazinyl)phenyl]-2-oxo-5-oxazolidinyl]methyl]cyclopropanecarbothioamide | P-130 | Z (c) |
| 323 | (S)-N-[[3-[4-(4-sulfamoyl-1-piperazinyl)phenyl]-2-oxo-5-oxazolidinyl]methyl]thioacetamide | P-131 | Ethyl dithioacetate |
| 324 | (S)-N-[[3-[4-(4-sulfamoyl-1-piperazinyl)phenyl]-2-oxo-5-oxazolidinyl]methyl]propanethioamide | P-131 | Z (a) |
| 325 | (S)-N-[[3-[4-(4-sulfamoyl-1-piperazinyl)phenyl]-2-oxo-5-oxazolidinyl]methyl]phenyl]-2-oxo-5-oxazolidinyl]methyl]-2-methylpropanethioamide | P-131 | Z (b) |
| 326 | (S)-N-[[3-[4-(4-sulfamoyl-1-piperazinyl)phenyl]-2-oxo-5-oxazolidinyl]methyl]cyclopropanecarbothioamide | P-131 | Z (c) |
| 327 | (S)-N-[[3-3-Fluoro-4-[4-(cyanomethyl)-1-piperazinyl]phenyl]-2-oxo-5-oxazolidinyl]methyl]thioacetamide | P-132 | Ethyl dithioacetate |
| 328 | (S)-N-[[3-[3-Fluoro-4-[4-(cyanomethyl)-1-piperazinyl]phenyl]-2-oxo-5-oxazolidinyl]methyl]propanethioamide | P-132 | Z (a) |
| 329 | (S)-N-[[3-[3-Fluoro-4-[4-(cyanomethyl)-1-piperazinyl]phenyl]-2-oxo-5-oxazolidinyl]methyl]-2-methylpropanethioamide | P-132 | Z (b) |
| 330 | (S)-N-[[3-[3-Fluoro-4-[4-(cyanomethyl)-1-piperazinyl]phenyl]-2-oxo-5-oxazolidinyl]methyl]cyclopropanecarbothioamide | P-132 | Z (c) |
| 331 | (S)-N-[[3-[3,5-Difluoro-4-[4-(cyanomethyl)-1-piperazinyl]phenyl]-2-oxo-5-oxazolidinyl]methyl]thioacetamide | P-133 | Ethyl dithioacetate |

TABLE G-continued

| | | | |
|---|---|---|---|
| 332 | (S)-N-[[3-[3,5-Difluoro-4-[4-(cyanomethyl)-1-piperazinyl]phenyl]-2-oxo-5-oxazolidinyl]methyl]propanethioamide | P-133 | Z (a) |
| 333 | (S)-N-[[3-[3,5-Difluoro-4-[4-cyanomethyl)-1-piperazinyl]phenyl]-2-oxo-5-oxazolidinyl]methyl]-2-methylpropanethioamide | P-133 | Z (b) |
| 334 | (S)-N-[[3-[3,5-Difluoro-4-[4-(cyanomethyl)-1-piperazinyl]phenyl]-2-oxo-5-oxazolidinyl]methyl]-cyclopropanecarbothioamide | P-133 | Z (c) |
| 335 | (S)-N-[[3-[4-[4-(cyanomethyl)-1-piperazinyl]phenyl]-2-oxo-5-oxazolidinyl]methyl]thioacetamide | P-134 | Ethyl dithio-acetate |
| 336 | (S)-N-[[3-[4-[4-(cyanomethyl)-1-piperazinyl]phenyl]-2-oxo-5-oxazolidinyl]methyl]propanethioamide | P-134 | Z (a) |
| 337 | (S)-N-[[3-[4-[4-(cyanomethyl)-1-piperazinyl]phenyl]-2-oxo-5-oxazolidinyl]methyl]-2-methylpropanethioamide | P-134 | Z (b) |
| 338 | (S)-N-[[3-[4-[4-(cyanomethyl)-1-piperazinyl]phenyl]-2-oxo-5-oxazolidinyl]methyl]cyclopropanecarbothioamide | | |
| 339 | (S)-N-[[3-[3-Fluoro-4-[4-(2-fluoroethyl)-1-piperazinyl]phenyl]-2-oxo-5-oxazolidinyl]methyl]thioacetamide | P-135 | Ethyl dithio-acetate |
| 340 | (S)-N-[[3-[3-Fluoro-4-[4-(2-fluoroethyl)-1-piperazinyl]phenyl]-2-oxo-5-oxazolidinyl]methyl]propanethioamide | P-135 | Z (a) |
| 341 | (S)-N-[[3-[3-Fluoro-4-[4-(2-fluoroethyl)-1-piperazinyl]phenyl]-2-oxo-5-oxazolidinyl]methyl]-2-methylpropanethioamide | P-135 | Z (b) |
| 342 | (S)-N-[[3-[3-Fluoro-4-[4-(2-fluoroethyl)-1-piperazinyl]phenyl]-2-oxo-5-oxazolidinyl]methyl]-cyclopropanecarbothioamide | P-135 | Z (c) |
| 343 | (S)-N-[[3-[3,5-Difluoro-4-[4-(2-fluoroethyl)-1-piperazinyl]phenyl]-2-oxo-5-oxazolidinyl]methyl]-thioacetamide | P-136 | Ethyl dithio-acetate |
| 344 | (S)-N-[[3-[3,5-Difluoro-4-(2-fluoroethyl)-1-piperazinyl]phenyl]-2-oxo-5-oxazolidinyl]methyl]propanethioamide | P-136 | Z (a) |
| 345 | (S)-N-[[3-[3,5-Difluoro-4-[4-(2-fluoroethyl)-1-piperazinyl]phenyl]-2-oxo-5-oxazolidinyl]methyl]-2-methylpropanethioamide | P-136 | Z (b) |
| 346 | (S)-N-[[3-[3,5-Difluoro-4-[4-(2-fluoroethyl)-1-piperazinyl]phenyl]-2-oxo-5-oxazolidinyl]methyl]-cyclopropanecarbothioamide | P-136 | Z (c) |
| 347 | (S)-N-[[3-[4-[4-(2-fluoroethyl)-1-piperazinyl]phenyl]-2-oxo-5-oxazolidinyl]methyl]thioacetamide | P-137 | Ethyl dithio-acetate |
| 348 | (S)-N-[[3-[4-[4-(2-fluoroethyl)-1-piperazinyl]phenyl]-2-oxo-5-oxazolidinyl]methyl]propanethioamide | P-137 | Z (a) |
| 349 | (S)-N-[[3-[4-[4-(2-fluoroethyl)-1-piperazinyl]phenyl]-2-oxo-5-oxazolidinyl]methyl]-2-methylpropanethioamide | P-137 | Z (b) |

TABLE G-continued

| | | | |
|---|---|---|---|
| 350 | (S)-N-[[3-[4-[4-(2-fluoroethyl)-1-piperazinyl]phenyl]-2-oxo-5-oxazolidinyl]methyl]cyclopropane-carbothioamide | P-137 | Z (c) |
| 351 | (S)-N-[[3-[3-Fluoro-4-(4-formyl-1-piperazinyl)phenyl]-2-oxo-5-oxazolidinyl]methyl]thioacetamide; Anal calcd for $C_{17}H_{21}FN_4O_3S$: C, 53.67; H, 5.56; N, 14.73; S, 8.43. Found: C, 53.14; H, 5.42; N, 14.25; S, 8.18. | P-138 | Ethyl dithio-acetate |
| 352 | (S)-N-[[3-[3-Fluoro-4-(4-formyl-1-piperazinyl)phenyl]-2-oxo-5-oxazolidinyl]methyl]propanethioamide; mp 166–167° C.; Anal. calcd for $C_{18}H_{23}FN_4O_3S$: C, 54.81; H, 5.88; N, 14.20; S, 8.13. Found: C, 54.83; H, 6.00; N, 14.12; S, 7.96. | P-138 | Z (a) |
| 353 | (S)-N-[[3-[3-Fluoro-4-(4-formyl-1-piperazinyl)phenyl]-2-oxo-5-oxazolidinyl]methyl]-2-methylpropane-thioamide; mp 157–158° C.: Anal. calcd for $C_{19}H_{25}FN_4O_3S$: C, 55.87, H, 6.17; N, 13.72; S, 7.85. Found: C, 55.67; H, 6.19; N, 13.50; S, 7.70. | P-138 | Z (b) |
| 354 | (S)-N-[[3-[3-Fluoro-4-(4-formyl-1-piperazinyl)phenyl]-2-oxo-5-oxazolidinyl]methyl]cyclopropane-carbothioamide; mp 178-179° C.; Anal. calcd for $C_{19}H_{23}FN_4O_3S$: C, 56.14; H, 5.70; N, 13.78; S, 7.89. Found: C, 56.13; H, 5.64; N, 13.64; S. 7.75. | P-138 | Z (c) |
| 355 | (S)-N-[[3-[3,5-Difluro-4-(4-formyl-1-piperazinyl)-phenyl]-2-oxo-5-oxazolidinyl]methyl]thioacetamide | P-139 | Ethyl dithio-acetate |
| 356 | (S)-N-[[3-[3,5-Difluro-4-(4-formyl-1-piperazinyl)-phenyl]-2-oxo-5-oxazolidinyl]methyl]-propanethioamide | P-139 | Z (a) |
| 357 | (S)-N-[[3-[3,5-Difluro-4-(4-formyl-1-piperazinyl)-phenyl]-2-oxo-5-oxazolidinyl]methyl]-2-methyl-propanethioamide | P-139 | Z (b) |
| 358 | (S)-N-[[3-[3,5-Difluro-4-(4-formyl-1-piperazinyl)-phenyl]-2-oxo-5-oxazolidinyl]methyl]cyclo-propanecarbothioamide | P-139 | Z (c) |
| 359 | (S)-N-[[3-[4-(4-formyl-1-piperazinyl)phenyl]-2-oxo-5-oxazolidinyl]methyl]thioacetamide | P-140 | Ethyl dithio-acetate |
| 360 | (S)-N-[[3-[4-(4-formyl-1-piperazinyl)phenyl]-2-oxo-5-oxazolidinyl]methyl]propanethioamide | P-140 | Z (a) |
| 361 | (S)-N-[[3-[4-(4-formyl-1-piperazinyl)phenyl]-2-oxo-5-oxazolidinyl]methyl]-2-methylpropanethioamide | P-140 | Z (b) |
| 362 | (S)-N-[[3-[4-(4-formyl-1-piperazinyl)phenyl]-2-oxo-5-oxazolidinyl]methyl]cyclopropane-carbothioamide | P-140 | Z (c) |

TABLE G-continued

| Example No. | Product | Isothiocyanate Corresponding to Amine No. | Amine |
|---|---|---|---|
| 363 | (S)-N-[[3-[3-Fluoro-4-(4-acetyl-1-piperazinyl)phenyl]-2-oxo-5-oxazolidinyl]methyl]-1-azetidinecarbothioamide | | |
| 364 | (S)-N-[[3-[3-Fluoro-4-[4-(methoxyacetyl)-1-piperazinyl]phenyl]-2-oxo-5-oxazolidinyl]methyl]-1-azetidinecarbothioamide | | |
| 365 | (S)-N-[[3-[3-Fluoro-4-[4-(acetoxyacetyl)-1-piperazinyl]phenyl]-2-oxo-5-oxazolidinyl]methyl]-1-azetidinecarbothioamide | | |
| 366 | (S)-N-[[3-[3-Fluoro-4-[4-(methoxycarbonyl)-1-piperazinyl]phenyl]-2-oxo-5-oxazolidinyl]methyl]-1-azetidinecarbothioamide | | |
| 367 | (S)-N-[[3-[3-Fluoro-4-[4-(ethoxycarbonyl)-1-piperazinyl]phenyl]-2-oxo-5-oxazolidinyl]methyl]-1-azetidinecarbothioamide | | |
| 368 | (S)-N-[[3-[3-Fluoro-4-(4-sulfamoyl-1-piperazinyl)phenyl]-2-oxo-5-oxazolidinyl]methyl]-1-azetidinecarbothioamide | | |

EXAMPLE 369

(5S)-N-[[3-[3-Fluoro-4-(tetrahydro-1,4-thiazepin-4(5H)-yl)phenyl]-2-oxo-5-oxazolidinyl]methyl]thioacetamide, thiazepine S-oxide

TABLE H

| Example No. | Compound | Amine | Dithioester (from Preparation Z) |
|---|---|---|---|
| 370 | (5S)-N-[[3-[3-Fluoro-4-(tetrahydro-1,4-thiazepin-4(5H)-yl))-phenyl]-2-oxo-5-oxazolidinyl]methyl]-propanethioamide, thiazepine S-oxide | (structure shown) | Z (a) |

TABLE H-continued

| Example No. | Compound | Amine | Dithioester (from Preparation Z) |
|---|---|---|---|
| 371 | S)-N-[[3-[3-Fluoro-4-(tetrahydro-1,4-thiazepin-4(5H)-yl))-phenyl]-2-oxo-5-oxazolidinyl]methyl]-2-methylpropanethio—amide, thiazepine S-oxide. | Same as above | Z (b) |
| 372 | (5S)-N-[[3-[3-Fluoro-4-(tetrahydro-1,4-thiazepin-4(5H)-yl))-phenyl]-2-oxo-5-oxazolidinyl]methyl]-cyclopropanecarbothio-amide, thiazepine S-oxide. | Same as above | Z (c) |
| 373 | (5S)-N-[[3-[3-Fluoro-4-(tetrahydro-1,4-thiazepin-4(5H)-yl))-phenyl]-2-oxo-5-oxazolidinyl]methyl]-butanethioamide, thiazepine S-oxide | Same as above | Z (d) |
| 374 | (5S)-N-[[3-[3-Fluoro-4-(tetrahydro-1,4-thiazepin-4(5H)-yl))-phenyl]-2-oxo-5-oxazolidinyl]methyl]-3-methylbutanethioamide, thiazepine S-oxide | Same as above | Z (e) |
| 375 | (5S)-N-[[3-[3-Fluoro-4-(tetrahydro-1,4-thiazepin-4(5H)-yl))-phenyl]-2-oxo-5-oxazolidinyl]methyl]-2-methylbutanethioamide, thiazepine S-oxide | Same as above | Z (f) |
| 376 | (5S)-N-[[3-[3-Fluoro-4-(tetrahydro-1,4-thiazepin-4(5H)-yl))-phenyl]-2-oxo-5-oxazolidinyl]methyl]-3,3-dimethylbutanethio—amide, thiazepine S-oxide | Same as above | Z (g) |

TABLE H-continued

| Example No. | Compound | Amine | Dithioester (from Preparation Z) |
|---|---|---|---|
| 377 | (5S)-N-[[3-[3-Fluoro-4-(tetrahydro-1,4-thiazepin-4(5H)-yl))-phenyl]-2-oxo-5-oxazolidinyl]methyl]-cyclobutanecarbothio-amide, thiazepine S-oxide | Same as above | Z (h) |
| 378 | (5S)-N-[[3-[3-Fluoro-4-(tetrahydro-1,4-thiazepin-4(5H)-yl))-phenyl]-2-oxo-5-oxazolidinyl]methyl]-1-cyclopentanecarbothio-amide, thiazepine S-oxide | Same as above | Z (i) |
| 379 | (5S)-N-[[3-[3-Fluoro-4 -(tetrahydro-1,4-thiazepin-4(5H)-yl))-phenyl]-2-oxo-5-oxazolidinyl]methyl]-cyclohexanecarbothio-amide, thiazepine S-oxide | Same as above | Z (j) |
| 380 | (5S)-N-[[3-[3-Fluoro-4-(tetrahydro-1,4-thiazepin-4(5H)-yl))-phenyl]-2-oxo-5-oxazolidinyl]methyl]-2-cyclopropylethanethio-amide, thiazepine S-oxide | Same as above | Z (k) |
| 381 | (5S)-N-[[3-[3-Fluoro-4-(tetrahydro-1,4-thiazepin-4(5H)-yl))-phenyl]-2-oxo-5-oxazolidinyl]methyl]-2-cyclobutylethanethio-amide, thiazepine S-oxide | | |

TABLE H-continued

| Example No. | Compound | Amine | Dithioester (from Preparation Z) |
|---|---|---|---|
| 382 | (5S)-N-[[3-[3-Fluoro-4-(tetrahydro-1,4-thiazepin-4(5H)-yl))-phenyl]-2-oxo-5-oxazolidinyl]methyl]-2-cyclopentylethanethioamide, thiazepine S-oxide | | |

EXAMPLE 383

(5S)-N-[[3-[3,5-Difluoro-4-(tetrahydro-1,4-thiazepin-4(5H)-yl)phenyl]-2-oxo-5-oxazolidinyl]methyl]thioacetamide, thiazepine S-oxide

TABLE I

| Example No. | Compound | Amine | Dithioester (from Preparation Z) |
|---|---|---|---|
| 384 | (5S)-N-[[3-[3,5-Difluoro-4-(tetrahydro-1,4-thiazepin-4(5H)-yl))-phenyl]-2-oxo-5-oxazolidinyl]methyl]-propanethioamide, thiazepine S-oxide |  | Z (a) |
| 385 | (5S)-N-[[3-[3,5-Difluoro-4-(tetrahydro-1,4-thiazepin-4(5H)-yl))-phenyl]-2-oxo-5-oxazolidinyl]methyl]-2-methylpropanethioamide, thiazepine S-oxide | Same as above | Z (b) |
| 386 | (5S)-N-[[3-[3,5-Difluoro-4-(tetrahydro-1,4-thiazepin-4(5H)-yl))-phenyl]-2-oxo-5-oxazolidinyl]methyl]-cyclopropanecarbothioamide, thiazepine S-oxide | Same as above | Z (c) |

EXAMPLE 387

(5S)-N-[[3-[4-(Tetrahydro-1,4-thiazepin-4(5H)-yl)phenyl]-2-oxo-5-oxazolidinyl]methyl]thioacetamide, thiazepine S-oxide.

TABLE J

| Example No. | Compound | Amine | Dithioester (from Preparation Z) |
|---|---|---|---|
| 388 | (5S)-N-[[3-[4-(Tetrahydro-1,4-yl))-phenyl]-2-oxo-5-thiazepin-4(5H)-oxazolidinyl]methyl]-propanethioamide, thiazepine S-oxide | | Z (a) |
| 389 | (5S)-N-[[3-[4-(Tetrahydro-1,4-thiazepin-4(5H)-yl))-phenyl]-2-oxo-5-oxazolidinyl]methyl]-2-methylpropanethioamide, thiazepine S-oxide | Same as above | Z (b) |
| 390 | (5S)-N-[[3-[4-(Tetrahydro-1,4-thiazepin-4(5H)-yl))-phenyl]-2-oxo-5-oxazolidinyl]methyl]-cyclopropanecarbothioamide, thiazepine S-oxide | Same as above | Z (c) |

EXAMPLE 391

(5S)-N-[[3-[3-Fluoro-4-(tetrahydro-1,4-thiazepin-4(5H)-yl)phenyl]-2-oxo-5-oxazolidinyl]methyl]thioacetamide, thiazepine S,S-dioxide

TABLE K

| Example No. | Compound | Amine | Dithioester (from Preparation Z) |
|---|---|---|---|
| 392 | (5S)-N-[[3-[3-Fluoro-4-(4-thiomorpholinyl]-phenyl]-2-oxo-5-oxazolidinyl]methyl]propanethioamide, thiazepine S,S-dioxide | | Z (a) |

TABLE K-continued

| Example No. | Compound | Amine | Dithioester (from Preparation Z) |
|---|---|---|---|
| 393 | (5S)-N-E[3-[3-Fluoro-4-(4-thiomorpholinyl]-phenly]-2-oxo-5-oxazolidinyl]methyl]-2-methylpropanethio-amide, thiazepine S,S-dioxide | Same as above | Z (b) |
| 394 | (5S)-N-[[3-[3-Fluoro-4-(4-thiomorpholinyl]-phenyl]-2-oxo-5-oxazolidinyl]methyl]-cyclopropanecarbothio-amide, thiazepine S,S-dioxide | Same as above | Z (c) |

EXAMPLE 395

(5S)-N-[[3-[3,5-Difluoro-4-(tetrahydro-1,4-thiazepin-4(5H)-yl)phenyl]-2-oxo-5-oxazolidinyl]methyl] thioacetamide, thiazepine S,S-dioxide

TABLE L

| Example No. | Compound | Amine | Dithioester (from Preparation Z) |
|---|---|---|---|
| 396 | (5S)-N-[[3-[3,5-Difluoro-4-(4-thiomorpholinyl]-phenyl]-2-oxo-5-oxazolidinyl]methyl]-propanethioamide, thiazepine S,S-dioxide | [structure shown] | Z (a) |
| 397 | (5S)-N-[[3-[3,5-Difluoro-4-(4-thiomorpholinyl]-phenyl]-2-oxo-5-oxazolidinyl]methyl]-2-methylpropanethio-amide, thiazepine S,S-dioxide | Same as above | Z (b) |
| 398 | (5S)-N-[[3-[3,5-Difluoro-4-(4-thiomorpholinyl]-phenyl]-2-oxo-5-oxazolidinyl]methyl]-cyclopropanecarbothio-amide, thiazepine S,S-dioxide | Same as above | Z (c) |

EXAMPLE 399

(5S)-N-[[3-[4-(Tetrahydro-1,4-thiazepin-4(5H)-yl)phenyl]-2-oxo-5-oxazolidinyl]methyl]thioacetamide, thiazepine S,S-dioxide

TABLE M

| Example No. | Compound | Amine | Dithioester (From Preparation Z) |
|---|---|---|---|
| 400 | (5S)-N-[[3-[4-(tetrahydro-1,4-thiazepin-4(5H)-yl))phenyl]-2-oxo-5-ozolidinyl]-methyl]propanethioamide, thiazepine S,S-dioxide | | Z (a) |
| 401 | (5S)-N-[[3-[4-(tetrahydro-1,4-thiazepin-4(5H)-yl))phenyl]-2-oxo-5-oxazolidinyl]methyl]-2-methylpropanethioamide, thiazepine S,S-dioxide | Same as above | Z (b) |
| 402 | (5S)-N-[[3-[4-(tetrahydro-1,4-thiazepin-4(5H)-yl))phenyl]-2-oxo-5-oxazolidinyl]methyl]cyclopropane-carbothioamide, thiazepine S,S-dioxide | Same as above | Z (c) |

EXAMPLE 403

(5S)-N-[[3-[3-Fluoro-4-(tetrahydro-1,4-thiazepin-4(5H)-yl)phenyl]-2-oxo-5-oxazolidinyl]methyl]thioacetamide

TABLE N

| Example No. | Compound | Amine | Dithioester (From Preparation Z) |
|---|---|---|---|
| 404 | (5S)-N-[[3-[3-Fluoro-4-(tetrahydro-1,4-phenyl]-4(5H)-yl))-henYlJ-2-oxo-5-oxazolidinyl]methyl]-propanethioamide | | Z (a) |

TABLE N-continued

| Example No. | Compound | Amine | Dithioester (From Preparation Z) |
|---|---|---|---|
| 405 | (5S)-N-[[3-[3-Fluoro-4-(tetrahydro-1,4-thiazepin-4(5H)-yl))-phenyl]-2-oxo-5-oxazolidinyl]methyl]-2-methylpropanethioamide | Same as above | Z (b) |
| 406 | (5S)-N-[[3-[3-Fluoro-4-(tetrahydro-1,4-thiazepin-4(5H)-yl))-phenyl]-2-oxo-5-oxazolidinyl]methyl]-cyclopropanecarbothioamide | Same as above | Z (c) |
| 407 | (5S)-N-[[3-[3-Fluoro-4-(tetrahydro-1,4-thiazepin-4(5H)-yl))-phenyl]-2-oxo-5-oxazolidinyl]methyl]-butanethioamide | Same as above | Z (d) |
| 408 | (5S)-N-[[3-[3-Fluoro-4-(tetrahydro-1,4-thiazepin-4(5H)-yl))-phenyl]-2-oxo-5-oxazolidinyl]methyl]-3-methylbutanethioamide | Same as above | Z (e) |
| 409 | (5S)-N-[[3-[3-Fluoro-4-(tetrahydro-1,4-thiazepin-4(5H)-yl))-phenyl]-2-oxo-5-oxazolidinyl]methyl]-2-methylbutanethioamide | Same as above | Z (f) |
| 410 | (5S)-N-[[3-[3-Fluoro-4-(tetrahydro-1,4-thiazepin-4(5H)-yl))-phenyl]-2-oxo-5-oxazolidinyl]methyl]-3,3-dimethylbutanethioamide | Same as above | Z (g) |
| 411 | (5S)-N-[[3-[3-Fluoro-4-(tetrahydro-1,4-thiazepin-4(5H)-yl))-phenyl]-2-oxo-5-oxazolidinyl]methyl]-cyclobutanecarbothioamide | Same as above | Z (h) |

TABLE N-continued

| Example No. | Compound | Amine | Dithioester (From Preparation Z) |
|---|---|---|---|
| 412 | (5S)-N-[[3-[3-Fluoro-4-(tetrahydro-1, 4-thiazepin-4(5H)-yl))-phenyl]-2-oxo-5-oxazolidinyl]methyl]-cyclopentanecarbothio-amide | Same as above | Z (i) |
| 413 | (5S)-N-[[3-[3-Fluoro-4-(tetrahydro-1,4-thiazepin-4(5H)-yl))-phenyl]-2-oxo-5-oxazolidinyl]methyl]-cyclohexanecarbothio-amide | Same as above | Z (j) |
| 414 | (5S)-N-[[3-[3-5 Fluoro-4-(tetrahydro 1,4-thiazepin-4(5H)-yl))-phenyl]-2-oxo-5-oxazolidinyl]methyl]-2-cyclopropylethanethio-amide | Same as above | Z (k) |
| 415 | (5S)-N-[[3-[3-Fluoro-4-(tetrahydro-1,4-thiazepin-4(5H)-yl))-phenyl]-2-oxo-5-oxazolidinyl]methyl]-2-cyclobutylethanethio-amide | Same as above | Z (l) |
| 416 | (5S)-N-[[3-[3-Fluoro-4-(tetrahydro-1,4-thiazepin-4(5H)-yl))-phenyl]-2-oxo-5-oxazolidinyl]methyl]-2-cyclopentylethanethioamide | Same as above | Z (m) |

EXAMPLE 417

(5S)-N-[[3-[3,5-Difluoro-4-(tetrahydro-1,4-thiazepin-4 (5H)-yl)phenyl]-2-oxo-5-oxazolidinyl]methyl]thioacetamide

TABLE O

| Example No. | Compound | Amine | Dithio Compound (from Preparation Z) |
|---|---|---|---|
| 418 | (5S)-N-[[3-[3,5-Difluoro-4-(tetrahydro-1,4-thiazepin-phenyl]-2-oxo-5-oxazolidinyl]methyl]-propanethioamide | | Z (a) |
| 419 | (5S)-N-[[3-[3,5-Difluoro-4-(tetrahydro-1,4-thiazepin-4(5H)-yl))-phenyl]-2-oxo-5-oxazolidinyl]methyl]-2-methylpropanethioamide | Same as above | Z (b) |
| 420 | (5S)-N-[[3-[3,5-Difluoro-4-(tetrahydro-1,4-thiazepin-4(5H)-yl))-phenyl]-2-oxo-5-oxazolidinyl]methyl]-cyclopropanecarbothioamide | Same as above | Z (c) |

EXAMPLE 421

(5S)-N-[[3-[4-(Tetrahydro-1,4-thiazepin-4(5H)-yl)phenyl]-2-oxo-5-oxazolidinyl]methyl]thioacetamide

TABLE P

| Example No. | Compound | Amine | Dithio Compound (from Preparation Z) |
|---|---|---|---|
| 422 | (5S)-N-[[3-[4-(Tetrahydro-1,4-thiazepin-4(5H)-yl))-phenyl]-2-oxo-5-oxazolidinyl]-methyl]propanethioamide | | Z (a) |

TABLE P-continued

| Example No. | Compound | Amine | Dithio Compound (from Preparation Z) |
|---|---|---|---|
| 423 | (5S)-N-[[3-[4-(Tetrahydro-1,4-thiazepin-4(5H)-yl))-phenyl]-2-oxo-5-oxazolidinyl]methyl]-2-methylpropanethioamide | Same as above | Z (b) |
| 424 | (5S)-N-[[3-[4-(Tetrahydro-1,4-thiazepin-4(5H)-yl))-phenyl]-2-oxo-5-oxazolidinyl]-methyl]cyclopropanecarbothioamide | Same as above | Z (c) |
| 425 | (5S)-N-[[3-[3-Fluoro-4-(tetrahydro-1,4-thiazepin-4(5H)-yl)phenyl]-2-oxo-5-oxazolidinyl]methyl]-1-azetidinecarbothioamide, thiazepine S-oxide | | |
| 426 | (5S)-N-[[3-[3-Fluoro-4-(tetrahydro-1,4-thiazepin-4(5H)-yl)phenyl]-2-oxo-5-oxazolidinyl]methyl]-O-methylthiocarbamate, thiazepine S-oxide | | |
| 427 | (5S)-N-[[3-[3,5-Difluoro-4-(tetrahydro-1,4-thiazepin-4(5H)-yl)phenyl]-2-oxo-5-oxazolidinyl]methyl]-1-azetidinecarbothioamide, thiazepine S-oxide | | |
| 428 | (5S)-N-[[3-[4-(Tetrahydro-1,4-thiazepin-4(5H)-yl)phenyl]-2-oxo-5-oxazolidinyl]methyl]-1-azetidinecarbothioamide, thiazepine S-oxide | | |
| 429 | (5S)-N-[[3-[3-Fluoro-4-(tetrahydro-1,4-thiazepin-4(5H)-yl)phenyl]-2-oxo-5-oxazolidinyl]methyl]-1-azetidinecarbothioamide, thiazepine S,S-dioxide | | |

TABLE P-continued

| Example No. | Compound | Amine | Dithio Compound (from Preparation Z) |
|---|---|---|---|
| 430 | (5S)-N-[[3-[3,5-Difluoro-4-(tetrahydro-1,4-thiazepin-4(5H)-yl)phenyl]-2-oxo-5-oxazolidinyl]methyl]-1-azetidinecarbothioamide, thiazepine S,S-dioxide | | |
| 431 | (5S)-N-[[3-[4-(Tetrahydro-1,4-thiazepin-4(5H)-yl)phenyl]-2-oxo-5-oxazolidinyl]methyl]-1-azetidinecarbothioamide, thiazepine S,S-dioxide | | |
| 432 | (5S)-N-[[3-[3-Fluoro-4-(tetrahydro-1,4-thiazepin-4(5H)-yl)phenyl]-2-oxo-5-oxazolidinyl]methyl]-1-azetidinecarbothioamide | | |
| 433 | (5S)-N-[[3-[3,5-Difluoro-4-(tetrahydro-1,4-thiazepin-4(5H)-yl)phenyl]-2-oxo-5-oxazolidinyl]methyl]-1-azetidinecarbothioamide | | |
| 434 | (5S)-N-[[3-[4-(Tetrahydro-1,4-thiazepin-4(5H)-yl)phenyl]-2-oxo-5-oxazolidinyl]methyl]-1-azetidinecarbothioamide | | |

EXAMPLE 435

(5R)-(−)-3-[3-Fluoro-4-(4-morpholinyl)phenyl]-2-oxo-5-oxazolidinecarboxamide—Method A

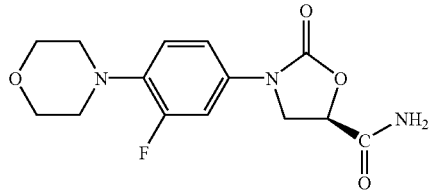

Step 1: Preparation of (5R)-(−)-3-[3-fluoro-4-(4-morpholinyl)phenyl]-2-oxo-5-oxazolidinecarboxylic acid A solution of benzyl 3-fluoro-4-(4-morpholinyl) phenylcarbamate (*J. Med. Chem.* 1996, 39(3), 673–679, 2.50 g, 7.57 mmol) in dry tetrahydrofuran (37.8 mL) at −78° C. under nitrogen was treated with n-butyllithium (1.6M in hexanes, 4.82 mL, 7.72 mmol) dropwise and stirred at −78° C. for 30 minutes. The cooling bath was removed and the mixture was allowed to slowly warm to −40° C., at which point potassium (2R)-glycidate (*J. Org. Chem.* 1992, 57(12), 3380–3387, 974 mg, 7.72 mmol) was added. After subsequent warming to ambient temperature, the resulting mixture was vigorously stirred for 2.75 days and then quenched with saturated aqueous ammonium chloride (20 mL), diluted with water (20 mL) and extracted with ethyl acetate (2×75 mL) to remove the remaining starting. The aqueous phase was adjusted to pH 2 with 1M aqueous hydrochloric acid, saturated with sodium chloride and extracted with methylene chloride (5×100 mL), and this combined organic phase was dried over anhydrous sodium sulfate and concentrated under reduced pressure to give the crude product. The product mixture was then chromatographed on a Flash 40M silica gel (90 g, 32–63 µm) cartridge, eluting with a gradient of acetonitrile/methylene chloride (10/90–40/60) containing 1% formic acid, and those fractions with an $R_f$=0.15 by TLC (acetonitrile/methylene chloride, 50/50+1% formic acid) are pooled and concentrated to give the title compound, $^1$H NMR (400 MHz, DMSO-$d_6$) δ 13.7 (bs, 1H), 7.48 (dd, 1H), 7.23 (m, 1H), 7.05 (t, 1H), 5.17 (dd, 1H), 4.30 (t, 1H), 4.06 (dd, 1H), 3.73 (m, 4H), 2.96 (m, 4H); MS (ESI+) for $C_{14}H_{15}FN_2O_5$ m/z 311 (M+H)$^+$; $[\alpha]^{25}_D$=−38° (c 0.94, DMSO).

Step 2: Preparation of (5R)-(−)-3-[3-fluoro-4-(4-morpholinyl)phenyl]-2-oxo-5-oxazolidinecarboxamide To a flame-dried flask containing (5R)-(−)-3-[3-fluoro-4-(4-morpholinyl)phenyl]-2-oxo-5-oxazolidinecarboxylic acid (Step 1, 250 mg, 0.806 mmol) under nitrogen was added oxalyl chloride (4 mL) with stirring. The flask was capped with a drying tube, and the mixture was stirred at ambient temperature for 15 hours and then concentrated under reduced pressure to give the acid chloride intermediate [MS (ESI+) m/z 325 (M+H)$^+$ observed for the methyl ester obtained by reaction of the acid chloride with methanol] which was used without further purification. This intermediate was then taken up in anhydrous tetrahydrofuran (8 mL) under nitrogen, cooled to 0° C., and ammonia (g) was bubbled in for 5 minutes. The resulting mixture was capped with a drying tube, stirred at ambient temperature for 1 hour, and then diluted with water (20 mL) and extracted with methanol/chloroform (10/90, 2×30 mL). The combined organic phase was dried over anhydrous sodium sulfate and concentrated under reduced pressure, and the product mixture was recrystallized from ethyl acetate/hexane to give the title compound, mp 185–187° C. (decomp.); MS (ESI+) for $C_{14}H_{16}FN_3O_4$ m/z 310 (M+H)$^+$; $[\alpha]^{25}_D$=−23° (c 0.89, DMSO).

EXAMPLE 436

(5R)-(−)-3-[3-Fluoro-4-(4-morpholinyl)phenyl]-N-methyl-2-oxo-5-oxazolidinecarboxamide

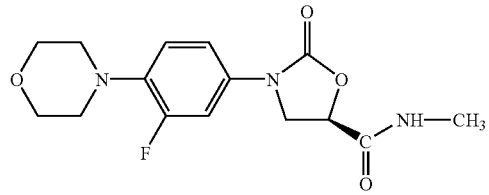

Following the general procedure of EXAMPLE 435, Step 2, and making non-critical variations but substituting methylamine for ammonia, the title compound was obtained, mp 182–183° C. (decomp.); MS (ESI+) for $C_{15}H_{18}FN_3O_4$ m/z 324 (M+H)$^+$; $[\alpha]^{25}_D$=−39° (c 0.92, DMSO).

EXAMPLE 437

(5R)-(−)-3-[3-Fluoro-4-(4-morpholinyl)phenyl]-N-allyl-2-oxo-5-oxazolidinecarboxamide

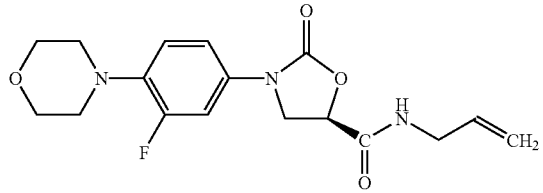

To a flame-dried flask under nitrogen was added allylamine (0.60 mL, 8.05 mmol). The flask was cooled in an ice bath, and a solution of (5R)-3-[3-fluoro-4-(4-morpholinyl)phenyl]-2-oxo-5-oxazolidinecarbonyl chloride (EXAMPLE 435, Step 2, 0.805 mmol theory) in anhydrous tetrahydrofuran (8.0 mL) was added. The resulting mixture was stirred under nitrogen for 2 hours, allowing the cooling bath to slowly expire, and was then diluted with water (10 mL) and extracted with methylene chloride (20 mL). The organic phase was washed with water (10 mL) and saline (10 mL), dried over anhydrous sodium sulfate and concentrated under reduced pressure, and the crude product was chromatographed on a Flash 40S silica gel (40 g, 32–63 µm) cartridge, eluting with a gradient of methanol/methylene chloride (0.5/99.5–2/98). Pooling and concentration of those fractions with an $R_f$=0.44 by TLC (methanol/chloroform, 5/95) provides the title compound, mp 167–169° C.; MS (ESI+) for $C_{17}H_{20}FN_3O_4$ m/z 350 (M+H)$^+$; $[\alpha]^{25}_D$=−44° (c 0.94, DMSO).

EXAMPLE 438

(5R)-(−)-3-[3-Fluoro-4-(4-morpholinyl)phenyl]-N-propyl-2-oxo-5-oxazolidinecarboxamide

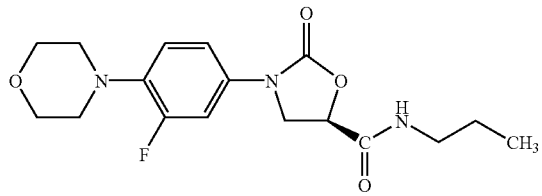

Following the general procedure of EXAMPLE 437, and making non-critical variations but substituting propylamine for allylamine and triturating and filtering the final product from methanol/diethyl ether, the title compound was obtained, mp 165–167° C.; MS (ESI+) for $C_{17}H_{22}FN_3O_4$ m/z 352 (M+H)$^+$; $[\alpha]^{25}_D$=−43° (c 1.02, DMSO).

EXAMPLE 439

(5R)-(−)-3-[3-Fluoro-4-(4-morpholinyl)phenyl]-N-methoxy-2-oxo-5-oxazolidinecarboxamide

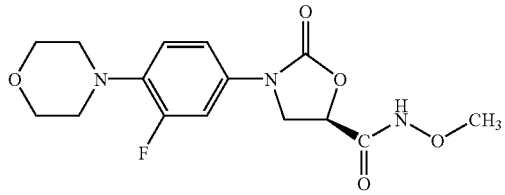

A mixture of (5R)-(−)-3-[3-fluoro-4-(4-morpholinyl)phenyl]-2-oxo-5-oxazolidinecarboxylic acid (EXAMPLE 1, Step 1, 150 mg, 0.483 mmol) and O-methylhydroxylamine hydrochloride (61 mg, 0.724 mmol) in tetrahydrofuran/water (1/1, 4.8 mL) was treated with 1-(3-dimethylaminopropyl)-3-ethylcarbodiimide hydrochloride (278 mg, 1.45 mmol), and the resulting mixture was stirred at ambient temperature for 30 minutes and was then diluted with water (10 mL) and extracted with ethyl acetate (2×20 mL). The combined organic phase was washed with water (10 mL) and saline (10 mL), dried over anhydrous sodium sulfate and concentrated under reduced pressure, and the crude product was chromatographed on a Flash 40S silica gel (40 g, 32–63 µm) cartridge, eluting with methanol/methylene chloride (2.5/97.5). Pooling and concentration of those fractions with an $R_f$=0.53 by TLC (methanol/chloroform, 10/90) gives the title compound, mp 206–208° C. (decomp.); MS (ESI+) for $C_{15}H_{18}FN_3O_5$ m/z 340 (M+H)$^+$; $[\alpha]^{25}_D$=−56° (c 0.92, DMSO).

EXAMPLE 440

(5R)-(−)-3-[3-Fluoro-4-(4-morpholinyl)phenyl]-N-hydroxy-2-oxo-5-oxazolidinecarboxamide

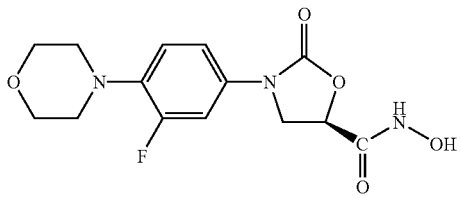

Step 1: Preparation of (5R)-(−)-3-[3-fluoro-4-(4-morpholinyl)phenyl]-N-benzyloxy-2-oxo-5-oxazolidinecarboxamide Following the general procedure of EXAMPLE 439, and making non-critical variations but substituting O-benzylhydroxylamine hydrochloride for O-methylhydroxylamine hydrochloride, the title compound was obtained, mp 191–193° C. (decomp.); MS (ESI+) for $C_{21}H_{22}FN_3O_5$ m/z 416 (M+H)$^+$; $[\alpha]^{25}_D$=−46° (c 0.93, DMSO).

Step 2: Preparation of (5R)-(−)-3-[3-fluoro-4-(4-morpholinyl)phenyl]-N-hydroxy-2-oxo-5-oxazolidinecarboxamide To a mixture of (5R)-(−)-3-[3-fluoro-4-(4-morpholinyl)phenyl]-N-benzyloxy-2-oxo-5-oxazolidinecarboxamide (Step 1, 300 mg, 0.722 mmol) in methanol (28.8 mL) was added 5% palladium-on-carbon (77 mg) under nitrogen. The resulting mixture was degassed and stirred under a hydrogen atmosphere (balloon) for 1 hour. The catalyst was then removed by filtration through Celite, rinsing with methanol (60 mL), and the filtrate was concentrated under reduced pressure. Trituration of this residue with (5% methanol/methylene chloride)/diethyl ether gives the title compound, mp 141–143° C.; MS (ESI+) for $C_{14}H_{16}FN_3O_5$ m/z 326 (M+H)$^+$; $[\alpha]^{25}_D$=−70° (c 0.99, DMSO).

EXAMPLE 441

(5R)-(−)-3-[4-(3-Pyridyl)-3-fluorophenyl]-2-oxo-5-oxazolidinecarboxamide

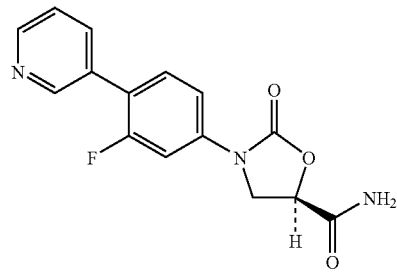

Step 1: Preparation of (5R)-(−)-3-[3-fluoro-4-iodophenyl]-5-hydroxymethyl-2-oxazolidinone A solution of isobutyl 3-fluoro-4-iodophenylcarbamate (*Org. Process Res. Dev.* 2001, 5(1), 80–83, 5.00 g, 14.83 mmol) in dry tetrahydrofuran (59 mL) at −78° C. under nitrogen was treated with lithium hexamethyldisilazide (1.0M in tetrahydrofuran, 15.6 mL, 15.57 mmol) dropwise and stirred at −78° C. for 45 minutes. Then, (R)-glycidyl butyrate (2.21 mL, 15.57 mmol) was added dropwise, and the resulting mixture was stirred at −78° C. for 1 hour and at ambient temperature for 2.75 days. The reaction mixture was then quenched with saturated aqueous ammonium chloride (20 mL), diluted with water (20 mL) and the layers are separated. The aqueous phase was extracted with ethyl acetate (25 mL), and the combined organic phase was washed with water (25 mL) and saline (25 mL), dried over anhydrous magnesium sulfate and concentrated under reduced pressure. The product mixture was then chromatographed on a Flash 40M silica gel (90 g, 32–63 µm) cartridge, eluting with a gradient of methanol/methylene chloride (1/99–2/98), and those fractions with an $R_f$=0.25 by TLC (methanol/chloroform, 5/95) are pooled and concentrated to give the title compound, mp 116–117° C.; MS (ESI+) for $C_{10}H_9FINO_3$ m/z 338 (M+H)$^+$; $[\alpha]^{25}_D$=−41 (c 0.98, DMSO)

Step 2: Preparation of (−)-methyl (5R)-3-[3-fluoro-4-iodophenyl]-2-oxo-5-oxazolidinecarboxylate A solution of (5R)-(−)-3-[3-fluoro-4-iodophenyl]-5-hydroxymethyl-2-oxazolidinone (Step 1, 7.61 g, 22.58 mmol) in acetone (150 mL) at −10° C. was treated with a mixture of $CrO_3$ (6.21 g, 62.1 mmol) in sulfuric acid (6M, 16.9 mL, 101 mmol) dropwise over 15 minutes. The resulting mixture was allowed to slowly warm to ambient temperature with vigorous stirring (slight exotherm to 35° C.) and was stirred for an additional 16 hours. The mixture was then treated with isopropanol (35 mL), diluted with saline (150 mL) and diethyl ether (150 mL), stirred until all solids are dissolved, and the layers are separated. The aqueous phase was extracted with diethyl ether (100 mL), and the combined organic phase was dried over anhydrous magnesium sulfate and concentrated under reduced pressure to give the crude carboxylic acid intermediate which was taken up in methanol (225 mL) and treated with concentrated sulfuric acid (8 drops). The resulting homogeneous mixture was stirred at ambient temperature for 20 hours and was then concentrated under reduced pressure to give the crude methyl ester product which was chromatographed on two Flash 40M 90 g silica gel (32–63 μm) cartridges, eluting with a gradient of ethyl acetate/heptane (20/80–40/60). Pooling and concentration of those fractions with an $R_f$=0.36 by TLC (ethyl acetate/hexane, 50/50) gives the title compound, mp 106–109° C.; MS (ESI+) for $C_{11}H_9FINO_4$ m/z 366 (M+H)$^+$; $[\alpha]^{25}_D$=−30 (c 0.93, DMSO).

Step 3: Preparation of (5R)-(−)-3-[3-fluoro-4-iodophenyl]-2-oxo-5-oxazolidinecarboxamide A solution of (−)-methyl (5R)-3-[3-fluoro-4-iodophenyl]-2-oxo-5-oxazolidinecarboxylate (Step 2, 6.23 g, 17.1 mmol) in acetonitrile (85 mL) was treated with concentrated ammonium hydroxide (85 mL), and the resulting mixture was stirred at ambient temperature for 1 hour. The mixture was then diluted with saline (100 mL) and extracted with methylene chloride (3×100 mL), and the combined organic phase was washed with saline (100 mL), dried over anhydrous sodium sulfate and concentrated under reduced pressure. The crude product was diluted with hot ethyl acetate (200 mL) and filtered to remove inorganic residue, and the filtrate was diluted with hexanes (300 mL). The resulting precipitate was isolated by filtration to give the title compound, mp 176–178° C.; MS (ESI+) for $C_{10}H_8FIN_2O_3$ m/z 351 (M+H)$^+$; $[\alpha]^{25}_D$=−19 (c 0.97, DMSO).

Step 4: Preparation of 3-(trimethylstannyl)pyridine

A mixture of hexamethylditin (654 mg, 1.99 mmol), 3-bromopyridine (300 mg, 1.90 mmol) and bis(triphenylphosphine)palladium(II) chloride (40 mg, 0.057 mmol) in 1,4-dioxane (9.5 ml) was degassed, heated up to 90° C. under nitrogen, stirred at this temperature for 2.5 hours and at ambient temperature overnight, and was then concentrated under reduced pressure. The product mixture was chromatographed on a Flash 40S 40 g silica gel (32–63 μm) cartridge, eluting with ethyl acetate/heptane (20/80), and those fractions with an $R_f$=0.47 by TLC (ethyl acetate/hexane, 50/50) are pooled and concentrated to give the title compound (see *Chem. Pharm. Bull.* 1982, 30(5), 1731–1737 for characterization).

Step 5: Preparation of (5R)-(−)-3-[4-(3-pyridyl)-3-fluorophenyl]-2-oxo-5-oxazolidinecarboxamide A mixture of (5R)-(−)-3-[3-fluoro-4-iodophenyl]-2-oxo-5-oxazolidinecarboxamide (Step 3, 422 mg, 1.21 mmol), 3-(trimethylstannyl)pyridine (Step 4, 350 mg, 1.45 mmol), tris(dibenzylideneacetone)dipalladium(0) (22 mg, 0.0242 mmol), triphenylarsine (59 mg, 0.194 mmol) and copper(I) iodide (9 mg, 0.0484 mmol) in N-methyl-2-pyrrolidinone (4.8 mL) under nitrogen was degassed, heated up to 50° C. and stirred at this temperature for 2 days, during which additional tris(dibenzylideneacetone)dipalladium(0) (22 mg, 0.0242 mmol), triphenylarsine (59 mg, 0.194 mmol) and copper(I) iodide (9 mg, 0.0484 mmol) are added. The resulting mixture was diluted with water (15 mL) and extracted with methylene chloride (3×20 mL), and the combined organic phase was dried over anhydrous sodium sulfate and concentrated under reduced pressure. The resulting oil was diluted with ethyl acetate (25 mL) and extracted with aqueous hydrochloric acid (1M, 25 mL), and the aqueous phase was neutralized with sodium hydroxide (s), saturated with sodium chloride and extracted with methylene chloride (3×25 mL) containing a small amount of methanol. This combined organic phase was dried over anhydrous sodium sulfate and concentrated under reduced pressure, and the residue was recrystallized from ethyl acetate/hexane to give the title compound, mp 240–242° C. (dec.); MS (ESI+) for $C_{15}H_{12}FN_3O_3$ m/z 302 (M+H)$^+$; $[\alpha]^{25}_D$=−25 (c 0.94, DMSO).

EXAMPLE 442

(5R)-(−)-3-[4-(4-Pyridyl)-3-fluorophenyl]-2-oxo-5-oxazolidinecarboxamide

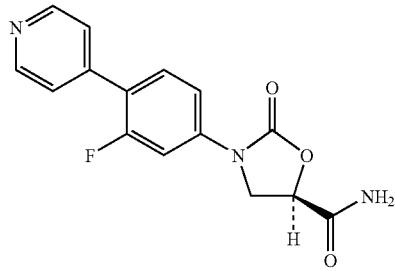

Following the general procedure of EXAMPLE 441, Step 5, and making non-critical variations but substituting 4-(trimethylstannyl)pyridine (U.S. Pat. No. 5,990,136, 23 Nov. 1999) for 3-(trimethylstannyl)pyridine, the title compound was obtained, mp 256–259° C. (dec.); MS (ESI+) for $C_{15}H_{12}FN_3O_3$ m/z 302 (M+H)$^+$; $[\alpha]^{25}_D$=−27 (c 0.94, DMSO).

EXAMPLE 443

(5R)-(−)-3-[4-(3,6-Dihydro-2H-pyran-4-yl)-3-fluorophenyl]-2-oxo-5-oxazolidinecarboxamide

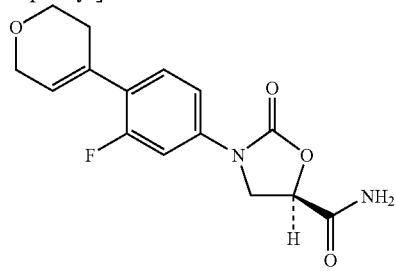

Step 1: Preparation of (5R)-3-[4-(trimethylstannyl)-3-fluorophenyl]-2-oxo-5-oxazolidinecarboxamide A mixture of (5R)-(−)-3-[3-fluoro-4-iodophenyl]-2-oxo-5-oxazolidinecarboxamide (EXAMPLE 441, Step 3, 3.50 g, 10.0 mmol), hexamethylditin (3.44 g, 10.5 mmol) and bis(triphenylphosphine)palladium(II) chloride (140 mg, 0.200 mmol) in 1,4-dioxane (50 mL) under nitrogen was degassed, heated up to 90° C. and stirred at 90° C. for 2 hours and at ambient temperature overnight. The resulting mixture was concentrated under reduced pressure to remove dioxane, diluted with methylene chloride (75 mL), washed with saline (25 mL), dried over anhydrous sodium sulfate and concentrated under reduced pressure. The residue was chromatographed on a Flash 40M 90 g silica gel (32–63 μm) cartridge, eluting with a gradient of methanol/methylene chloride (1/99–2/98), and those fractions with an $R_f$=0.26 by TLC (methanol/chloroform, 5/95) are pooled and concentrated to give the title compound, $^1$H NMR (400 MHz, CDCl$_3$) δ 7.38 (m, 2H), 7.20 (m, 1H), 6.65 (s, 1H), 5.82 (s, 1H), 5.00 (dd, 1H), 4.26 (m, 2H), 0.35 (m, 9H).

Step 2: Preparation of (5R)-(−)-3-[4-(3,6-dihydro-2H-pyran-4-yl)-3-fluorophenyl]-2-oxo-5-oxazolidinecarboxamide A mixture of 3,6-dihydro-2H-pyran-4-yl trifluoromethanesulfonic acid ester (U.S. Pat. No. 5,968,962, 19 Oct. 1999, 682 mg, 2.94 mmol), tris(dibenzylideneacetone)dipalladium(0) (54 mg, 0.0588 mmol) and triphenylarsine (144 mg, 0.470 mmol) in N-methyl-2-pyrrolidinone (14.7 mL) was degassed and stirred under nitrogen for 5 minutes. (5R)-3-[4-(trimethylstannyl)-3-fluorophenyl]-2-oxo-5-oxazolidinecarboxamide (Step 1, 1.14 g, 2.94 mmol) was then added, and the resulting mixture was stirred at ambient temperature for 5 days. The reaction mixture was then diluted with water (25 mL) and extracted with ethyl acetate (3×30 mL), and the combined organic phase was washed with water (3×30 mL) and saline (20 mL), dried over anhydrous magnesium sulfate and concentrated under reduced pressure. The crude product mixture was chromatographed on a Flash 40M 90 g silica gel (32–63 μm) cartridge, eluting with a gradient of methanol/methylene chloride (1/99–2.5/97.5), and those fractions with an $R_f$=0.40 by TLC (methanol/chloroform, 2×5/95) are pooled and concentrated to give the title compound, mp 164–169° C.; MS (ESI–) for $C_{15}H_{15}N_2O_4F$ m/z 305 (M–H)⁻; $[\alpha]^{25}_D$=–23 (c 0.96, DMSO).

EXAMPLE 444

(5R)-(–)-3-[4-(Tetrahydro-2H-pyran-4-yl)-3-fluorophenyl]-2-oxo-5-oxazolidinecarboxamide

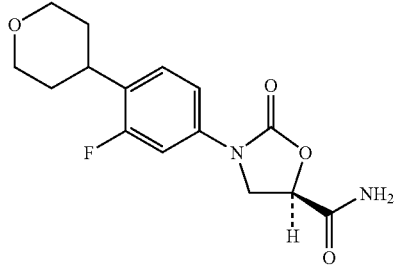

A mixture of (5R)-(–)-3-[4-(3,6-dihydro-2H-pyran-4-yl)-3-fluorophenyl]-2-oxo-5-oxazolidinecarboxamide (EXAMPLE 443, Step 2, 200 mg, 0.653 mmol) and 10% palladium-on-carbon (139 mg, 0.131 mmol) in methanol (26 mL) was shaken under a 40 psi hydrogen atmosphere on a Parr apparatus for 5 hours. The catalyst was then removed by filtration through a pad of Celite, and the filtrate was concentrated under reduced pressure and chromatographed on a Flash 40S 40 g silica gel (32–63 μm) cartridge, eluting with a gradient of methanol/methylene chloride (2/98–3/97). Pooling and concentration of those fractions with an $R_f$=0.37 by TLC (methanol/chloroform, 2×5/95) gives the title compound, mp 153–156° C.; MS (ESI–) for $C_{15}H_{17}N_2O_4F$ m/z 307 (M–H)⁻; $[\alpha]^{25}_D$=–21 (c 0.87, DMSO).

EXAMPLE 445

(5R)-3-[4-(3,6-Dihydro-2H-thiopyran-4-yl)-3-fluorophenyl]-2-oxo-5-oxazolidinecarboxamide S-oxide

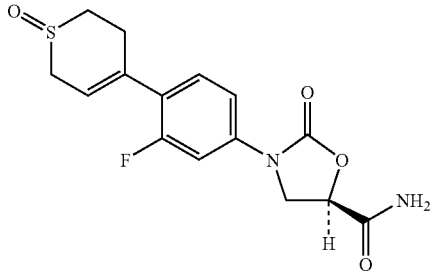

Step 1: Preparation of (–)-methyl (5R)-3-[4-(3,6-dihydro-2H-thiopyran-4-yl)-3-fluorophenyl]-2-oxo-5-oxazolidinecarboxylate Following the general procedure of EXAMPLE 435, Step 1, and making non-critical variations but substituting isobutyl 4-(3,6-dihydro-2H-thiopyran-4-yl)-3-fluorophenylcarbamate (WO 00/44741, Aug. 3, 2000) for benzyl 3-fluoro-4-(4-morpholinyl)phenylcarbamate, the crude (5R)-3-[4-(3,6-dihydro-2H-thiopyran-4-yl)-3-fluorophenyl]-2-oxo-5-oxazolidinecarboxylic acid intermediate was obtained and was used without further purification. This intermediate (540 mg crude) was taken up in methanol (16 mL), a drop of concentrated sulfuric acid was added, and the mixture was stirred at ambient temperature for 21 hours. Then, the reaction mixture was concentrated under reduced pressure and chromatographed on a Flash 40S 40 g silica gel (32–63 μm) cartridge, eluting with ethyl acetate/heptane (25/75). Pooling and concentration of those fractions with an $R_f$=0.25 by TLC (ethyl acetate/hexs, 50/50) give the title compound, mp 106–110° C.; MS (ESI+) for $C_{16}H_{16}NO_4FS$ m/z 338 (M+H)⁺; $[\alpha]^{25}_D$=–36 (c 0.99, DMSO).

Step 2: Preparation of (5R)-(–)-3-[4-(3,6-dihydro-2H-thiopyran-4-yl)-3-fluorophenyl]-2-oxo-5-oxazolidinecarboxamide Following the general procedure of EXAMPLE 441, Step 3, and making non-critical variations but substituting (–)-methyl (5R)-3-[4-(3,6-dihydro-2H-thiopyran-4-yl)-3-fluorophenyl]-2-oxo-5-oxazolidinecarboxylate (Step 1) for (–)-methyl (5R)-3-[3-fluoro-4-iodophenyl]-2-oxo-5-oxazolidinecarboxylate and purifying the product by recrystallization from methanol/diethyl ether, the title compound was obtained, mp 182–184° C. (dec.); MS (ESI–) for $C_{15}H_{15}FN_2O_3S$ m/z 321 (M–H)⁻; $[\alpha]^{25}_D$=–24 (c 0.93, DMSO).

Step 3: Preparation of (5R)-3-[4-(3,6-dihydro-2H-thiopyran-4-yl)-3-fluorophenyl]-2-oxo-5-oxazolidinecarboxamide S-oxide A mixture of (5R)-(–)-3-[4-(3,6-dihydro-2H-thiopyran-4-yl)-3-fluorophenyl]-2-oxo-5-oxazolidinecarboxamide (Step 2, 294 mg, 0.912 mmol) in methanol (18 mL) was treated with sodium periodate (205 mg, 0.958 mmol) in water (3.8 mL), and the mixture was stirred at ambient temperature for 44 hours. The resulting mixture was diluted with water (25 mL) and extracted with methylene chloride (5×30 mL), and the combined organic phase was dried over anhydrous sodium sulfate and concentrated under reduced pressure. The crude product mixture was triturated with acetone/diethyl ether and then filtered to give the title compound as a mixture of two diastereomers, ¹H NMR (400 MHz, DMSO-$d_6$) δ 7.87 (s, 1H), 7.63 (s, 1H), 7.52 (d, 1H), 7.39 (m, 2H), 5.83 (m, 1H), 5.04 (dd, 1H), 4.29 (t, 1H), 4.02 (dd, 1H), 3.65 (m, 1H), 3.39 (m, 1H), 3.10 (m, 1H), 2.92 (m, 2H), 2.54 (m, 1H); MS (ESI+) for $C_{15}H_{15}FN_2O_4S$ m/z 339 (M+H)⁺.

EXAMPLE 446

(5R)-(–)-3-[4-(3,6-Dihydro-2H-thiopyran-4-yl)-3-fluorophenyl]-2-oxo-5-oxazolidinecarboxamide S,S-dioxide

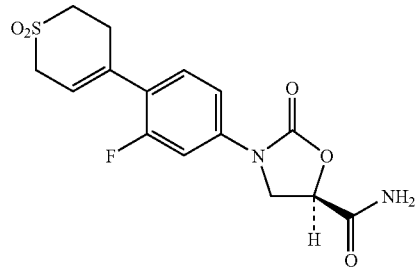

A solution of (5R)-(–)-3-[4-(3,6-dihydro-2H-thiopyran-4-yl)-3-fluorophenyl]-2-oxo-5-oxazolidinecarboxamide (EXAMPLE 445, Step 2, 209 mg, 0.648 mmol) in water/acetone (25/75, 13 mL) under nitrogen was treated with N-methylmorpholine N-oxide (190 mg, 1.62 mmol) and osmium tetroxide (2.5 wt % in tBuOH, 0.41 mL, 0.0324 mmol), and the mixture was stirred at ambient temperature for 43 hours. The reaction was then treated with ½-saturated aqueous sodium bisulfite (25 mL) and extracted with methylene chloride (3×25 mL), and the combined organic phase was dried over anhydrous sodium sulfate and concentrated under reduced pressure. The residue was chromatographed on a Flash 40S 40 g silica gel (32–63 m) cartridge, eluting with a gradient of methanol/methylene chloride (2.5/97.5–4/96), and those fractions with an $R_f$=0.48 by TLC (methanol/chloroform, 10/90) are pooled and concentrated to give the title compound, mp 206–208° C.; MS (ESI–) for $C_{15}H_{15}FN_2O_5S$ m/z 353 (M–H)$^-$; $[\alpha]^{25}_D$=–20 (c 0.98, DMSO).

EXAMPLE 447

(5R)-(–)-3-[4-(Tetrahydro-2H-thiopyran-4-yl)-3-fluorophenyl]-2-oxo-5-oxazolidinecarboxamide S,S-dioxide

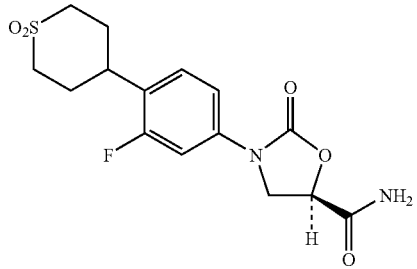

A mixture of (5R)-(–)-3-[4-(3,6-dihydro-2H-thiopyran-4-yl)-3-fluorophenyl]-2-oxo-5-oxazolidinecarboxamide S,S-dioxide (EXAMPLE 446, 73 mg, 0.206 mmol) and 10% palladium-on-carbon (44 mg, 0.0412 mmol) in methanol (21 mL) was shaken under a 40 psi hydrogen atmosphere on a Parr apparatus for 16 hours. The catalyst was then removed by filtration through a pad of Celite, rinsing with methanol and tetrahydrofuran, and the filtrate was concentrated under reduced pressure and triturated with (5% methanol/methylene chloride)/diethyl ether. Filtration then provides the title compound, mp 229–231° C. (dec.); MS (ESI–) for $C_{15}H_{17}FN_2O_5S$ m/z 355 (M–H)$^-$; $[\alpha]^{25}_D$=–20 (c 0.83, DMSO).

EXAMPLE 448

(5R)-(–)-3-[3-Fluoro-4-[4-(hydroxyacetyl)-1-piperazinyl]phenyl]-2-oxo-5-oxazolidinecarboxamide

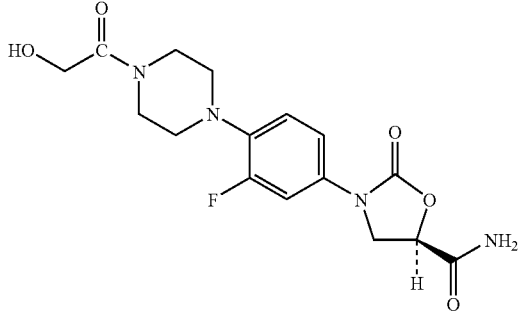

Step 1: Preparation of (–)-phenylmethyl 4-[4-[(5R)-5-(aminocarbonyl)-2-oxo-3-oxazolidinyl]-2-fluorophenyl]-1-piperazinecarboxylate Following the general procedure of EXAMPLE 435, Step 1, and making non-critical variations but substituting benzyl 4-(4-{[benzyloxycarbonyl]amino}-2-fluorophenyl)-1-piperazinecarboxylate (J. Med. Chem. 1996, 39(3), 673–679) for benzyl 3-fluoro-4-(4-morpholinyl)phenylcarbamate, the crude 1-(phenylmethyl)-4-[4-[(5R)-5-carboxy-2-oxo-3-oxazolidinyl]-2-fluorophenyl]-1-piperazinecarboxylate intermediate was obtained [MS (ESI–) for $C_{22}H_{22}N_3O_6F$ m/z 442 (M–H)$^-$] and was used without further purification. This intermediate (1.66 g crude) was taken up in methanol (75 mL), 4 drops of concentrated sulfuric acid are added, and the mixture was stirred at ambient-temperature for 19 hours. Then, the reaction mixture was concentrated under reduced pressure and chromatographed twice on a Flash 40M 90 g silica gel (32–63 μm) cartridge, eluting with a gradient of methanol/methylene chloride (1/99–2/98). Pooling and concentration of those fractions with an $R_f$=0.64 by TLC (methanol/chloroform, 5/95) provides 740 mg of the phenylmethyl 4-[2-fluoro-4-[(5R)-5-(methoxycarbonyl)-2-oxo-3-oxazolidinyl]phenyl]-1-piperazinecarboxylate intermediate [MS (ESI+) for $C_{23}H_{24}N_3O_6F$ m/z 458 (M+H)$^+$; 75–80% purity] which was used without further purification. This intermediate was taken up in 2M ammonia in methanol (13 mL), and the resulting mixture was stirred at ambient temperature for 3 hours and then concentrated under reduced pressure. The residue was chromatographed on a Flash 40M 90 g silica gel (32–63 μm) cartridge, eluting with a gradient of methanol/methylene chloride (1/99–3/97), and those fractions with an $R_f$=0.20 by TLC (methanol/chloroform, 5/95) are pooled and concentrated to give the title compound, mp 172–175° C.; MS (ESI+) for $C_{22}H_{23}N_4O_5F$ m/z 443 (M+H)$^+$; $[\alpha]^{25}_D$=–17 (c 1.04, DMSO).

Step 2: Preparation of (5R)-3-[3-fluoro-4-[4-[(phenylmethoxy)acetyl]-1-piperazinyl]phenyl]-2-oxo-5-oxazolidinecarboxamide A mixture of (–)-phenylmethyl 4-[4-[(5R)-5-(aminocarbonyl)-2-oxo-3-oxazolidinyl]-2-fluorophenyl]-1-piperazinecarboxylate (Step 1, 415 mg, 0.938 mmol) and 10% palladium-on-carbon (100 mg, 0.0938 mmol) in methanol (45 mL) was shaken under a 45 psi hydrogen atmosphere on a Parr apparatus for 4 hours. The catalyst was then removed by filtration through a pad of Celite, and the filtrate was concentrated under reduced pressure to give 290 mg (100%) of the (5R)-3-[(3-fluoro-4-piperazinyl)phenyl]-2-oxo-5-oxazolidinecarboxamide intermediate [MS (ESI+) for $C_{14}H_{17}N_4O_3F$ m/z 309 (M+H)$^+$] which was used without further purification. A mixture of this intermediate (240 mg, 0.778 mmol) in methylene chloride (7.8 mL) under nitrogen was treated with triethylamine (163 μL, 1.17 mmol) followed by benzyloxyacetyl chloride (135 μL, 0.856 mmol), and the resulting homogeneous mixture was stirred at ambient temperature for 3 hours. The reaction mixture was then diluted with water (20 mL) and methylene chloride (20 mL), the layers are separated, and the organic phase was washed with saline (10 mL), dried over anhydrous sodium sulfate and concentrated under reduced pressure to give the crude product which was then chromatographed on a Flash 40M 90 g silica gel (32–63 μm) cartridge, eluting with methanol/methylene chloride (2.5/97.5). Pooling and concentration of those fractions with an $R_f$=0.50 by TLC (methanol/chloroform, 10/90) provides the title compound, $^1$H NMR (400 MHz, DMSO-$d_6$) δ 7.85 (s, 1H), 7.61 (s, 1H), 7.52 (dd, 1H), 7.36 (m, 4H), 7.31 (m, 1H), 7.24 (m, 1H), 7.06 (m, 1H), 5.01 (dd, 1H), 4.53 (s, 2H), 4.25 (m, 3H), 3.97 (dd, 1H), 3.58 (m, 4H), 2.96 (m, 4H); MS (ESI+) for $C_{23}H_{25}FN_4O_5$ m/z 457 (M+H)$^+$.

Step 3: Preparation of (5R)-(–)-3-[3-fluoro-4-[4-(hydroxyacetyl)-1-piperazinyl]phenyl]-2-oxo-5-oxazolidinecarboxamide A mixture of (5R)-3-[3-fluoro-4-[4-[(phenylmethoxy)acetyl]-1-piperazinyl]phenyl]-2-oxo-5-oxazolidinecarboxamide (Step 2, 260 mg, 0.570 mmol) and 10% palladium-on-carbon (61 mg, 0.0570 mmol) in a mixture of methanol (5 mL) and EtOH (23 mL) was shaken under a 40 psi hydrogen atmosphere on a Parr apparatus for 22 hours. The catalyst was then removed by filtration through a pad of Celite, rinsing with tetrahydrofuran (200 mL), and the filtrate was concentrated under reduced pressure and triturated with methanol/diethyl ether. Filtration then provided the title compound, mp 232–235° C. (dec.); MS (ESI+) for $C_{16}H_{19}FN_4O_5$ m/z 367 (M+H)$^+$; $[\alpha]^{25}{}_D$=−20 (c 0.98, DMSO).

EXAMPLE 449

(5R)-(−)-3-[4-(Thiomorpholin-4-yl)-3,5-difluorophenyl]-2-oxo-5-oxazolidinecarboxamide S,S-dioxide

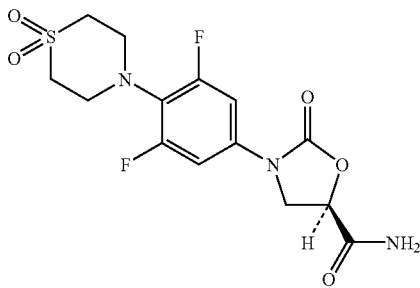

Step 1: Preparation of 4-(2,6-difluorophenyl)thiomorpholine 1,1-dioxide

Aluminum chloride (310 g, 2.3 mol) was added to chlorobenzene (2.5 L) to give a cloudy green suspension. Vinyl sulfone (230 mL, 2.3 mol) was added via funnel, followed by 2,6-difluoroaniline (250 mL, 2.3 mol). The light brown solution was heated to 110° C. Upon completion of the reaction, the heat was removed and the black solution was self-cooled to 70° C. The reaction mixture was then quenched in methylene chloride (4 L) and ice water (5 L), the aqueous phase was extracted with methylene chloride (3 L, 2 L, 2 L, 2 L) and the combined organic layers are concentrated, rediluted with branched octane (3 L), and then cooled to 0° C. for 30 minutes. The solids are filtered and washed with branched octane (2×500 mL) and are then dissolved in methylene chloride (3 L) and loaded onto a $SiO_2$ plug (1.8 kg). The column was eluted with dichloromethane (16 L) until clear. The methylene chloride solution was concentrated, and the solids are dissolved in hot ethyl acetate (3 L) followed by the addition of hexanes (900 mL). The black solution was self-cooled to room temperature overnight, and the resulting light amber crystal needles are filtered and washed with hexanes (4×250 mL). The solids are dried under reduced pressure at 50° C. overnight to give the title compound, $^1$H NMR (CDCl$_3$) (δ): 7.08 (m, 1H), 6.91 (m, 2H), 3.67 (m, 4H), 3.18 (m, 4H).

Step 2: Preparation of 4-(2,6-difluoro-4-nitrophenyl) thiomorpholine 1,1-dioxide To a suspension of 4-(2,6-difluorophenyl)thiomorpholine 1,1-dioxide (Step 1, 300 g, 1.21 mol) in 3 L of acetic acid, nitric acid (255 mL, ca. 6 mol, fuming, 90%) was added over 30 minutes at ambient temperature. A yellow precipitate forms within minutes and increases over time. The reaction was kept at room temperature for 18 hours and was then poured into 6 L of water. After stirring for 2 hours, the yellow suspension was filtered. The precipitate was washed with water (1.5 L×3) and ethanol (0.5 L×2) and dried at 50° C. overnight to give the title compound, $^1$H NMR (DMSO-d$_6$) (δ): 8.05 (m, 2H), 3.69 (m, 4H), 3.26 (m, 4H).

Step 3: Preparation of 4-(1,1-dioxido-4-thiomorpholinyl)-3,5-difluoroaniline

To an autoclave was added 4-(2,6-difluoro-4-nitrophenyl) thiomorpholine 1,1-dioxide (Step 2, 7.0 kg, 24 moles, 1.0 eq). Raney Nickel (1.4 kg) was activated and suspended in tetrahydrofuran (4 L), and the slurry was added to the autoclave followed by additional tetrahydrofuran (66 L). The mixture was heated at 40° C. under a 40 psi hydrogen atmosphere until the reaction was complete. The mixture was then filtered, and the filtrate was directly used in the next step. A small portion of the filtrate can be concentrated and recrystallized in isopropanol to give the title compound in pure form, $^1$H NMR (DMSO-d$_6$) (δ): 6.17 (m, 2H), 5.35 (s, 2H), 3.32 (m, 4H), 3.15 (m, 4H).

Step 4: Preparation of isobutyl 4-(1,1-dioxido-4-thiomorpholinyl)-3,5-difluorophenylcarbamate To a 400 L glass-lined reactor containing the 4-(1,1-dioxido-4-thiomorpholinyl)-3,5-difluoroaniline/ tetrahydrofuran solutions (Step 3, 12.6 kg, 48 moles, 1.0 eq) was added 47% potassium carbonate solution (14.1 kg, 48 moles, 1.0 eq). The mixture was heated to approximately 45° C., and isobutyl chloroformate (7.2 kg, 53 moles, 1.1 eq) was added while maintaining a reaction temperature between 45° C. and 55° C. The reaction was stirred at 45°–55° C. Once deemed complete, the reaction was quenched by slowly adding water (45 L) over 15 minutes. The reaction mixture was cooled to 25° C. and the phases are separated. The tetrahydrofuran solution was swapped to an isopropanol (150 L)/water (50 L) suspension, and the slurry was slowly cooled to 5° C. The yellow slurry was then filtered and the cake washed with cold isopropanol (2×30 L). The yellow solids are dried with 60° C. nitrogen to give the title compound, $^1$H NMR (CDCl$_3$) (δ): 7.02 (m, 2H), 6.81 (s, 1H), 3.95 (d, 2H), 3.60 (m, 4H), 3.17 (m, 4H), 1.97 (m, 1H), 0.94 (d, 6H).

Step 5: Preparation of (5R)-(−)-3-[4-(thiomorpholin-4-yl)-3,5-difluorophenyl]-2-oxo-5-oxazolidinecarboxamide S,S-dioxide Following the general procedure of EXAMPLE 448, Step 1, and making non-critical variations but substituting isobutyl 4-(1,1-dioxido-4-thiomorpholinyl)-3,5-difluorophenylcarbamate (Step 4) for benzyl 4-(4-{[benzyloxycarbonyl]amino}-2-fluorophenyl)-1-piperazinecarboxylate and purifying the final product by trituration and filtration from (10% methanol/chloroform)/ diethyl ether, the title compound was obtained, mp 245–248° C. (dec.); MS (ESI+) for $C_{14}H_{15}F_2N_3O_5S$ m/z 376 (M+H)$^+$; $[\delta]^{25}{}_D$=−22 (c 1.00, DMSO).

EXAMPLE 450

(5R)-(−)-3-[3-Fluoro-4-(4-morpholinyl)phenyl]-2-oxo-5-oxazolidinecarboxamide—Method C

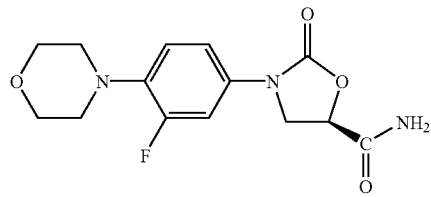

Step 1: Preparation of ethyl (5R)-3-[3-fluoro-4-(4-morpholinyl)phenyl]-2-oxo-5-oxazolidinecarboxylate A solution of 3-fluoro-4-morpholinoaniline (*J. Med. Chem.* 1996, 39(3), 673–679, 0.796 g, 4.0 mmol), ethyl 2(R)-epoxypropanoate (0.696 g, 6.0 mmol) and lithium triflate (0.97 g, 6.2 mmol) in acetonitrile (12 mL) was stirred at 50–60° C. overnight. Solvent and excess epoxide was removed under reduced pressure, and the crude amino alcohol was redissolved in dry acetonitrile (40 mL) and 1,1'-carbonyldiimidazole (1.46 g, 9.0 mmol) was added. The mixture was stirred at ambient temperature overnight, and then the solvent was removed under reduced pressure. The residue was partitioned between ethyl acetate (70 mL) and 3% aqueous citric acid (100 mL), the layers are separated, and the organic phase was washed with 3% aqueous citric acid (3×100 mL), water and saline, dried over anhydrous magnesium sulfate and concentrated under reduced pressure. The product mixture was then purified by silica gel chromatography, eluting with ethanol/methylene chloride (2/98), and the appropriate fractions are pooled and concentrated to give the title compound, MS (ESI+) for $C_{16}H_{19}N_2O_5F$ m/z 339 (M+H)$^+$.

Step 2: Preparation of (5R)-(-)-3-[3-fluoro-4-(4-morpholinyl)phenyl]-2-oxo-5-oxazolidinecarboxamide A mixture of of ethyl (5R)-3-[3-fluoro-4-(4-morpholinyl) phenyl]-2-oxo-5-oxazolidinecarboxylate (Step 1, 0.22 g, 0.65 mmol) in 2M ammonia in methanol (5–6 mL) was heated in a closed vial at 60° C. for approximately 1 hour. The resulting mixture was cooled to ambient temperature and concentrated under reduced pressure, and the crude product was recrystallized from methanol to give the title compound, MS (ESI+) for $C_{14}H_{16}N_3O_4F$ m/z 310 (M+H)$^+$.

EXAMPLE 451

(5R)-(-)-3-[3,5-Difluoro-4-(4-morpholinyl)phenyl]-2-oxo-5-oxazolidinecarboxamide

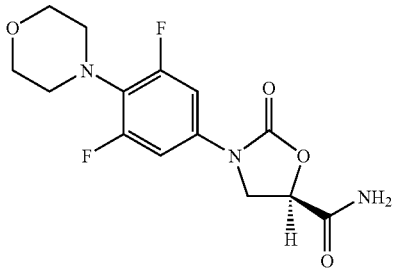

Step 1: Preparation of butyl (5R)-3-[3,5-difluoro-4-(4-morpholinyl)phenyl]-2-oxo-5-oxazolidinecarboxylate A solution of 3,5-difluoro-4-(4-morpholinyl)aniline (See U.S. Pat. No. 5,688,792, 2.00 g, 9.34 mmol), butyl 2(R)-glycidate (2.02 g, 14.0 mmol) and lithium triflate (2.18 g, 14.0 mmol) in acetonitrile (37 mL) was stirred at 60° C. under $N_2$ for 48 hrs. Solvent was removed under reduced pressure, and the residue was taken up in MeOH/CH$_2$Cl$_2$ (5/95, 100 mL), washed with water (2×25 mL) and saline (25 mL), dried over anhydrous sodium sulfate and concentrated under reduced pressure. The residue was flushed through a Flash 40M 90 g silica gel cartridge with EtOAc/CH$_2$Cl$_2$ (10/90), and the appropriate fractions were pooled and concentrated to give the amino alcohol intermediate [$R_f$=0.10 by TLC, EtOAc/hexanes (25/75)] which was contaminated with residual starting material. This intermediate (2.5 g in two lots) was then dissolved in acetonitrile (total of 70 mL) and treated with 1,1'-carbonyldiimidazole (total of 1.69 g, 10.4 mmol, 1.5 equiv.), and the reaction mixtures were stirred at ambient temperature for 6 days and then concentrated under reduced pressure. The product mixtures were each taken up in CH$_2$Cl$_2$ (50 mL), washed with 0.1M hydrochloric acid (2×20 mL) and saline (10 mL), dried over anhydrous sodium sulfate, concentrated under reduced pressure and chromatographed on a Flash 40M 90 g silica gel cartridge with EtOAc/CH$_2$Cl$_2$ (5/95). Those fractions with an $R_f$=0.16 by TLC (EtOAc/hexanes, 25/75) were pooled and concentrated to give the title compound, mp 99–100° C.; MS (ESI+) for $C_{18}H_{22}N_2O_5F_2$ m/z 385 (M+H)$^+$.

Step 2: Preparation of (5R)-(-)-3-[3,5-difluoro-4-(4-morpholinyl)phenyl]-2-oxo-5-oxazolidinecarboxamide The butyl (5R)-3-[3,5-difluoro-4-(4-morpholinyl) phenyl]-2-oxo-5-oxazolidinecarboxylate (Step 1, 350 mg, 0.910 mmol) was treated with 7N ammonia in methanol (9.1 mL) under $N_2$, and the mixture was stirred at ambient temperature for 30 mins. The reaction mixture was then concentrated under reduced pressure, and the residue was recrystallized from EtOAc/hexanes to give the title compound, mp 181–183° C.; MS (ESI+) for $C_{14}H_{15}N_3O_4F_2$ m/z 328 (M+H)$^+$; [α]$^{25}_D$ –23 (c 0.94, DMSO).

EXAMPLE 452

(5R)-(-)-3-[4-(Thiomorpholin-4-yl)phenyl]-2-oxo-5-oxazolidinecarboxamide S,S-dioxide

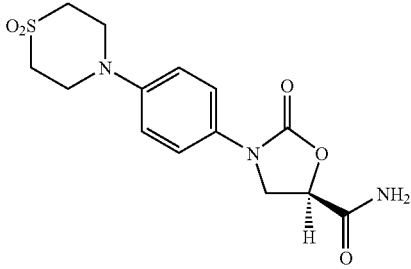

Step 1: Preparation of butyl (5R)-3-[4-(thiomorpholin-4-yl) phenyl]-2-oxo-5-oxazolidinecarboxylate A solution of 4-(4-thiomorpholinyl)aniline (See *Med. Chem. Res.* 1999, 9(3), 149–161, 2.60 g, 13.4 mmol), butyl 2(R)-glycidate (2.89 g, 20.1 mmol) and lithium triflate (3.13 g, 20.1 mmol) in acetonitrile (54 mL) was stirred at 60° C. under $N_2$ for 36 hrs. Solvent was removed under reduced pressure, and the residue was taken up in MeOH/CH$_2$Cl$_2$ (5/95, 100 mL), washed with water (50 mL) and saline (20 mL), dried over anhydrous sodium sulfate and concentrated under reduced pressure. The residue was flushed through a Flash 40M 90 g silica gel cartridge with EtOAc/CH$_2$Cl$_2$ (15/85), and the appropriate fractions were pooled and concentrated to give the amino alcohol intermediate [$R_f$= 0.19 by TLC, EtOAc/hexanes (25/75)] which was contaminated with the dialkylated by-product. This intermediate (4.25 g) was then dissolved in acetonitrile (125 mL) and treated with 1,1'-carbonyldiimidazole (3.05 g, 18.8 mmol, 1.5 equiv.), and the reaction mixture was stirred at ambient temperature for approximately 3 days and then concentrated under reduced pressure. The product mixture was taken up in CH$_2$Cl$_2$ (100 mL), washed with 0.1M hydrochloric acid (3×25 mL) and saline (25 mL), dried over anhydrous sodium sulfate, concentrated under reduced pressure and chromatographed on a Flash 40M 90 g silica gel cartridge with EtOAc/CH$_2$Cl$_2$ (15/85). Those fractions with an $R_f$=0.57 by TLC (EtOAc/hexanes, 50/50) were pooled and concentrated to give the title compound, mp 95.5–98° C.; MS (ESI+) for $C_{18}H_{24}N_2O_4S$ m/z 365 (M+H)$^+$.

Step 2: Preparation of butyl (5R)-3-[4-(thiomorpholin-4-yl) phenyl]-2-oxo-5-oxazolidinecarboxylate S,S-dioxide A solution of butyl (5R)-3-[4-(thiomorpholin-4-yl) phenyl]-2-oxo-5-oxazolidinecarboxylate (Step 1, 600 mg, 1.65 mmol) in water/acetone (25/75, 32 mL) under N₂ was treated with N-methylmorpholine N-oxide (483 mg, 4.12 mmol) and osmium tetroxide (2.5 wt % in tBuOH, 1.03 mL, 0.0825 mmol), and the mixture was stirred at ambient temperature for 18 hrs. The reaction was then treated with ½-saturated aqueous sodium bisulfite (20 mL), diluted with water (20 mL) and extracted with CH₂Cl₂ (2×50 mL). The combined organic phase was washed with saline (20 mL), dried over anhydrous sodium sulfate and concentrated under reduced pressure, and the product mixture was chromatographed on a Flash 40S 40 g silica gel cartridge with MeOH/CH₂Cl₂ (1/99). Pooling and concentration of those fractions with an $R_f$=0.5 by TLC (MeOH/CHCl₃, 5/95) followed by recrystallization from EtOAc/hexanes gave the title compound, mp 100–102° C.; MS (ESI+) for $C_{18}H_{24}N_2O_6S$ m/z 397 (M+H)⁺.

Step 3: Preparation of (5R)-(−)-3-[4-(thiomorpholin-4-yl)phenyl]-2-oxo-5-oxazolidinecarboxamide S,S-dioxide The butyl (5R)-3-[4-(thiomorpholin-4-yl)phenyl]-2-oxo-5-oxazolidinecarboxylate S,S-dioxide (Step 2, 400 mg, 1.01 mmol) was treated with 7N ammonia in methanol (10.1 mL) under N₂, and the mixture was stirred at ambient temperature for 25 mins. The resulting slurry was then diluted with diethyl ether (5 mL) and filtered to give the title compound, mp 226–228° C.; MS (ESI−) for $C_{14}H_{17}N_3O_5S$ m/z 338 (M−H)⁻; $[\alpha]^{25}_D$ −22 (c 0.94, DMSO).

EXAMPLE 453

(5R)-(−)-3-[3-Fluoro-4-(thiomorpholin-4-yl)phenyl]-2-oxo-5-oxazolidinecarboxamide S,S-dioxide

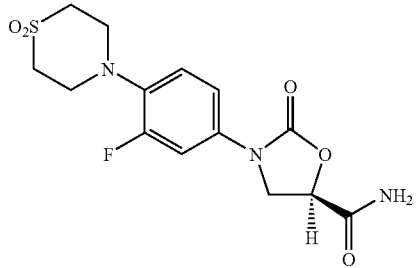

Step 1: Preparation of butyl (5R)-3-[3-fluoro-4-(thiomorpholin-4-yl)phenyl]-2-oxo-5-oxazolidinecarboxylate Following the general procedure of EXAMPLE 452, Step 1, and making non-critical variations but substituting 3-fluoro-4-(4-thiomorpholinyl)aniline (See *J. Med. Chem.* 1996, 39(3), 680–685) for 4-(4-thiomorpholinyl)aniline, the title compound was obtained, mp 128–130° C.; MS (ESI+) for $C_{18}H_{23}N_2O_4FS$ m/z 383 (M+H)⁺.

Step 2: Preparation of butyl (5R)-3-[3-fluoro-4-(thiomorpholin-4-yl)phenyl]-2-oxo-5-oxazolidinecarboxylate S,S-dioxide Following the general procedure of EXAMPLE 452, Step 2, and making non-critical variations but substituting butyl (5R)-3-[3-fluoro-4-(thiomorpholin-4-yl)phenyl]-2-oxo-5-oxazolidinecarboxylate (Step 1) for butyl (5R)-3-[4-(thiomorpholin-4-yl)phenyl]-2-oxo-5-oxazolidinecarboxylate, the title compound was obtained, mp 169–171° C. (dec.); MS (ESI+) for $C_{18}H_{23}N_2O_6FS$ m/z 415 (M+H)⁺.

Step 3: Preparation of (5R)-(−)-3-[3-fluoro-4-(thiomorpholin-4-yl)phenyl]-2-oxo-5-oxazolidinecarboxamide S,S-dioxide Following the general procedure of EXAMPLE 452, Step 3, and making non-critical variations but substituting butyl (5R)-3-[3-fluoro-4-(thiomorpholin-4-yl)phenyl]-2-oxo-5-oxazolidinecarboxylate S,S-dioxide (Step 2) for butyl (5R)-3-[4-(thiomorpholin-4-yl)phenyl]-2-oxo-5-oxazolidinecarboxylate S,S-dioxide, the title compound was obtained, mp 245–247° C. (dec.); MS (ESI+) for $C_{14}H_{16}N_3O_5FS$ m/z 358 (M+H)⁺; $[\alpha]^{25}_D$ −22 (c 0.92, DMSO).

EXAMPLE 454

(5R)-(−)-3-[3-Fluoro-4-(thiomorpholin-4-yl)phenyl]-2-oxo-5-oxazolidinecarboxamide S-oxide

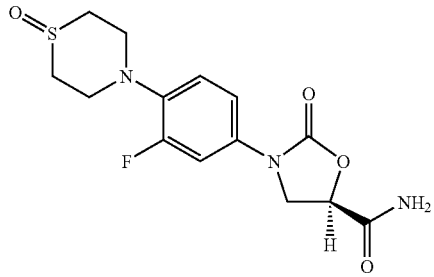

Step 1: Preparation of butyl (5R)-3-[3-fluoro-4-(thiomorpholin-4-yl)phenyl]-2-oxo-5-oxazolidinecarboxylate S-oxide A solution of sodium periodate (265 mg, 1.24 mmol) in water (5 mL) was treated with a slurry of butyl (5R)-3-[3-fluoro-4-(thiomorpholin-4-yl)phenyl]-2-oxo-5-oxazolidinecarboxylate (EXAMPLE 20, Step 1, 450 mg, 1.18 mmol) in methanol (24 mL), and the mixture was stirred at ambient temperature for 23 hrs. The resulting mixture was diluted with water (20 mL) and saline (20 mL) and extracted with CH₂Cl₂ (2×40 mL), and the combined organic phase was dried over anhydrous sodium sulfate and concentrated under reduced pressure. The residue was chromatographed on a Flash 40S 40 g silica gel cartridge, eluting with a gradient of MeOH/CH₂Cl₂ (1/99–2/98), and those fractions with an $R_f$=0.37 by TLC (MeOH/CHCl₃, 5/95) were pooled and concentrated and the residue recrystallized from EtOAc/hexanes to give the title compound, mp 128–129° C.; MS (ESI+) for $C_{18}H_{23}N_2O_5FS$ m/z 399 (M+H)⁺.

Step 2: Preparation of (5R)-(−)-3-[3-fluoro-4-(thiomorpholin-4-yl)phenyl]-2-oxo-5-oxazolidinecarboxamide S-oxide Following the general procedure of EXAMPLE 452, Step 3, and making non-critical variations, but substituting (SR)-3-[3-fluoro-4-(thiomorpholin-4-yl)phenyl]-2-oxo-5-oxazolidinecarboxamide S-oxide (Step 1) for butyl (5R)-3-[4-(thiomorpholin-4-yl)phenyl]-2-oxo-5-oxazolidinecarboxylate S,S-dioxide and purifying the product by trituration and filtration from hot acetonitrile, the title compound was obtained, mp 264–266° C. (dec.); MS (ESI+) for $C_{14}H_{16}N_3O_4FS$ m/z 342 (M+H)⁺; $[\alpha]^{25}_D$ −22 (c 0.39, DMSO).

EXAMPLE 455

(5R)-(−)-3-[3,5-Difluoro-4-(thiomorpholin-4-yl)phenyl]-2-oxo-5-oxazolidinecarboxamide S-oxide

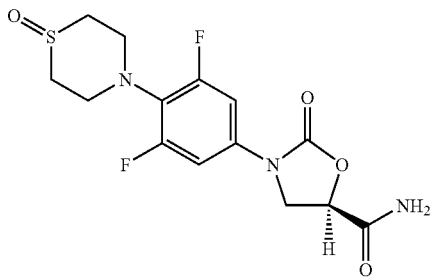

Step 1: Preparation of 4-(2,6-Difluoro-4-nitrophenyl)thiomorpholine

A solution of 3,4,5-trifluoronitrobenzene (5.00 g, 28.24 mmol) in acetonitrile (60 mL) was cooled to 0° C. and treated with N,N-diisopropylethylamine (7.38 mL, 42.35 mmol) followed by thiomorpholine (2.98 mL, 29.65 mmol). The ice bath was removed and the reaction mixture stirred at room temperature under nitrogen for approximately 24 hrs, during which additional thiomorpholine (0.1 eq) was added. The solvent was removed under reduced pressure, and the residue was diluted with ethyl acetate, washed with 1N hydrochloric acid (until the washings were acidic), saturated aqueous sodium bicarbonate and saline, dried over anhydrous sodium sulfate, and concentrated under reduced pressure to give the title compound, mp 104–105° C.

Step 2: Preparation of 3,5-difluoro-4-(4-morpholinyl)aniline

A solution of 4-(2,6-difluoro-4-nitrophenyl)thiomorpholine (3.00 g, 11.5 mmol) in tetrahydrofuran (60 mL) was added to a Parr bottle containing a mixture of Raney nickel (1 g) in water (15 mL) under $N_2$, and the reaction mixture was shaken on a Parr apparatus under a hydrogen atmosphere at 40 psi for 24 hrs. The catalyst was removed by filtration through Celite, rinsing with tetrahydrofuran and water, the filtrate was diluted with water (50 mL) and EtOAc (50 mL), and the layers were separated. The organic phase was washed with saline (25 mL), dried over anhydrous magnesium sulfate and concentrated under reduced pressure, and the resulting oil was chromatographed on a Flash 40M 90 g silica gel cartridge eluting with EtOAc/heptane (15/85). Pooling and concentration of those fractions with an Rt=0.19 by TLC (EtOAc/hexanes, 25/75) gave the title compound, mp 85–86° C.; MS (ESI+) for $C_{10}H_{12}N_2F_2S$ m/z 231 (M+H)$^+$.

Step 3: Preparation of butyl (5R)-3-[3,5-difluoro-4-(thiomorpholin-4-yl)phenyl]-2-oxo-5-oxazolidinecarboxylate Following the general procedure of EXAMPLE 452, Step 1, and making non-critical variations but substituting 3,5-difluoro-4-(4-morpholinyl)aniline (Step 2) for 4-(4-thiomorpholinyl)aniline, the title compound was obtained, mp 102–103° C.; MS (ESI+) for $C_{18}H_{22}N_2O_4F_2S$ m/z 401 (M+H)$^+$.

Step 4: Preparation of butyl (5R)-3-[3,5-difluoro-4-(thiomorpholin-4-yl)phenyl]-2-oxo-5-oxazolidinecarboxylate S-oxide Following the general procedure of EXAMPLE 454, Step 1, and making non-critical variations but substituting butyl (5R)-3-[3,5-difluoro-4-(thiomorpholin-4-yl)phenyl]-2-oxo-5-oxazolidinecarboxylate (Step 3) for butyl (5R)-3-[4-(thiomorpholin-4-yl)phenyl]-2-oxo-5-oxazolidinecarboxylate, the title compound was obtained, mp 114–116° C.; MS (ESI+) for $C_{18}H_{22}N_2O_5F_2S$ m/z 417 (M+H)$^+$.

Step 5: Preparation of (5R)-(−)-3-[3,5-Difluoro-4-(thiomorpholin-4-yl)phenyl]-2-oxo-5-oxazolidinecarboxamide S-oxide Following the general procedure of EXAMPLE 452, Step 3, and making non-critical variations, but substituting (5R)-3-[3,5-difluoro-4-(thiomorpholin-4-yl)phenyl]-2-oxo-5-oxazolidinecarboxamide S-oxide (Step 4) for butyl (5R)-3-[4-(thiomorpholin-4-yl)phenyl]-2-oxo-5-oxazolidinecarboxylate S,S-dioxide, the title compound was obtained, mp 273–276° C. (dec.); MS (ESI+) for $C_{14}H_{15}N_3O_4F_2S$ m/z 360 (M+H)$^+$; $[\alpha]^{25}_D$ −24 (c 0.96, DMSO).

EXAMPLE 456

(SR)-3-[3-Fluoro-4-(cis-tetrahydro-1-oxido-2H-thiopyran-4-yl)phenyl]-2-oxo-5-oxazolidinecarboxamide

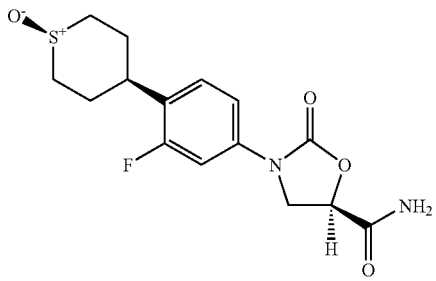

Step 1: Preparation of 2-methylpropyl [3-fluoro-4-(tetrahydro-2H-thiopyran-4-yl)phenyl]carbamate A solution of 2-methylpropyl [3-fluoro-4-(tetrahydro-4-hydroxy-2H-thiopyran-4-yl)phenyl]carbamate (See *Org. Proc. Res. Dev.* 2001, 5, 80–83, 4.00 g, 12.2 mmol) in trifluoroacetic acid (19 mL, 244 mmol) under $N_2$ was treated with triethylsilane (5.85 mL, 36.6 mmol) dropwise, stirred for 1 hr, and then added dropwise to saturated aqueous potassium carbonate (250 mL) with vigorous stirring. The mixture was extracted with diethyl ether (200 mL), and the organic phase was washed with water (2×50 mL) and saline (50 mL), dried over anhydrous magnesium sulfate and concentrated under reduced pressure. Trituration and filtration from diethyl ether/hexanes or ethyl acetate/hexanes gave the title compound, $^1$H NMR (CDCl$_3$, 400 MHz) δ 7.26 (m, 1H), 7.11 (t, 1H), 6.97 (m, 1H), 6.59 (bs, 1H), 3.95 (d, 2H), 2.85 (m, 3H), 2.68 (m, 2H), 2.09 (m, 2H), 1.98 (m, 1H), 1.84 (m, 2H), 0.96 (d, 6H).

Step 2: Preparation of 3-fluoro-4-(tetrahydro-2H-thiopyran-4-yl)benzenamine

A mixture of 2-methylpropyl [3-fluoro-4-(tetrahydro-2H-thiopyran-4-yl)phenyl]carbamate (Step 1, 2.12 g, 6.81 mmol) in ethylene glycol (25 mL) was treated with aqueous potassium hydroxide (45%, 25.5 g, 204 mmol) with vigorous stirring, and the mixture was heated to 95° C. and stirred at this temperature for 18 hrs. The reaction was then cooled to ambient temperature and diluted with water (50 mL) and CH$_2$Cl$_2$ (100 mL), the layers were separated, and the organic phase was washed with water (50 mL) and saline (20 mL), dried over anhydrous sodium sulfate and concentrated under reduced pressure. The crude product was chromatographed on a Flash 40M 90 g silica gel cartridge with a gradient of EtOAc/heptane (15/85–25/75), and those fractions with an R$_f$=0.32 by TLC (EtOAc/hexanes, 25/75) were pooled and concentrated to give the title compound, mp 96–98° C.; MS (ESI+) for $C_{11}H_{14}NFS$ m/z 212 (M+H)$^+$.

Step 3: Preparation of butyl (5R)-3-[3-fluoro-4-(tetrahydro-2H-thiopyran-4-yl)phenyl]-2-oxo-5-oxazolidinecarboxylate Following the general procedure of EXAMPLE 452, Step 1, and making non-critical variations but substituting 3-fluoro-4-(tetrahydro-2H-thiopyran-4-yl)benzenamine (Step 2) for 4-(4-thiomorpholinyl)aniline, the title compound was obtained, mp 98–100° C.; MS (ESI+) for $C_{19}H_{24}NO_4FS$ m/z 382 (M+H)$^+$.

Step 4: Preparation of butyl (5R)-3-[3-fluoro-4-(cis-tetrahydro-1-oxido-2H-thiopyran-4-yl)phenyl]-2-oxo-5-oxazolidinecarboxylate Following the general procedure of EXAMPLE 454, Step 1, and making non-critical variations but substituting butyl (5R)-3-[3-fluoro-4-(tetrahydro-2H-thiopyran-4-yl)phenyl]-2-oxo-5-oxazolidinecarboxylate (Step 3) for butyl (5R)-3-[4-(thiomorpholin-4-yl)phenyl]-2-oxo-5-oxazolidinecarboxylate, a mixture of the cis and trans sulfoxide products in approximately a 2:1 ratio was obtained. Subsequent purification by preparative HPLC (Chiralcel OD column, EtOH eluent) followed by recrystallization from EtOAc/hexanes provided the title compound, mp 142–145° C.; MS (ESI+) for $C_{19}H_{24}NO_5FS$ m/z 398 (M+H)$^+$.

Step 5: Preparation of (5R)-3-[3-fluoro-4-(cis-tetrahydro-1-oxido-2H-thiopyran-4-yl)phenyl]-2-oxo-5-oxazolidinecarboxamide Following the general procedure of EXAMPLE 452, Step 3, and making non-critical variations, but substituting butyl (SR)-3-[3-fluoro-4-(cis-tetrahydro-1-oxido-2H-thiopyran-4-yl)phenyl]-2-oxo-5-oxazolidinecarboxylate (Step 4) for butyl (5R)-3-[4-(thiomorphoilin-4-yl)phenyl]-2-oxo-5-oxazolidinecarboxylate S,S-dioxide and purifying the product by trituration and filtration from hot methanol and acetonitrile, the title compound was obtained, mp 279–281° C. (dec.); MS (ESI+) for $C_{15}H_{17}N_2O_4FS$ m/z 341 (M+H)$^+$.

EXAMPLE 457

(5R)-3-[3-Fluoro-4-(trans-tetrahydro-1-oxido-2H-thiopyran-4-yl)phenyl]-2-oxo-5-oxazolidinecarboxamide

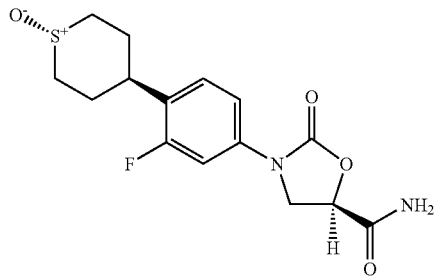

Step 1: Preparation of butyl (5R)-3-[3-fluoro-4-(trans-tetrahydro-1-oxido-2H-thiopyran-4-yl)phenyl]-2-oxo-5-oxazolidinecarboxylate Following the general procedure of EXAMPLE 454, Step 1, and making non-critical variations but substituting butyl (5R)-3-[3-fluoro-4-(tetrahydro-2H-thiopyran-4-yl)phenyl]-2-oxo-5-oxazolidinecarboxylate (EXAMPLE 23, Step 3) for butyl (5R)-3-[4-(thiomorpholin-4-yl)phenyl]-2-oxo-5-oxazolidinecarboxylate, a mixture of the cis and trans sulfoxide products in approximately a 2:1 ratio was obtained. Subsequent purification by preparative HPLC (Chiralcel OD column, EtOH eluent) followed by recrystallization from EtOAc/hexanes provided the title compound, mp 133–136° C.; MS (ESI+) for $C_{19}H_{24}NO_5FS$ m/z 398 (M+H)$^+$.

Step 2: Preparation of (5R)-3-[3-fluoro-4-(trans-tetrahydro-1-oxido-2H-thiopyran-4-yl)phenyl]-2-oxo-5-oxazolidinecarboxamide Following the general procedure of EXAMPLE 452, Step 3, and making non-critical variations, but substituting butyl (SR)-3-[3-fluoro-4-(trans-tetrahydro-1-oxido-2H-thiopyran-4-yl)phenyl]-2-oxo-5-oxazolidinecarboxylate (Step 1) for butyl (5R)-3-[4-(thiomorpholin-4-yl)phenyl]-2-oxo-5-oxazolidinecarboxylate S,S-dioxide, the title compound was obtained, mp 201–203° C.; MS (ESI+) for $C_{15}H_{17}N_2O_4FS$ m/z 341 (M+H)$^+$.

EXAMPLE 458

(5R)-(−)-3-[4-(tetrahydro-2H-thiopyran-4-yl)phenyl]-2-oxo-5-oxazolidinecarboxamide S,S-dioxide

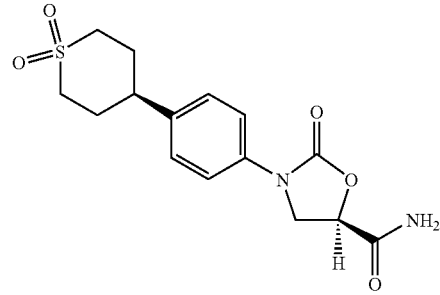

Step 1: Preparation of 2-methylpropyl 4-bromophenylcarbamate

A solution of 4-bromoaniline (10.0 g, 58.1 mmol) in tetrahydrofuran (230 mL) was treated with sodium bicarbonate (9.77 g, 116.2 mmol) and water (100 mL) followed by isobutyl chloroformate (8.3 mL, 63.9 mmol), and the mixture was stirred at ambient temperature for 2 hrs. The mixture was then diluted with water (100 mL) and EtOAc (100 mL), the layers were separated, and the organic phase was washed with water (50 mL) and saline (50 mL), dried over anhydrous magnesium sulfate and concentrated under reduced pressure. Recrystallization of the resulting solid from EtOAc/hexanes provided the title compound, mp 95–96° C.; MS (ESI−) for $C_{11}H_{14}NO_2Br$ m/z 270 (M−H)$^−$.

Step 2: Preparation of 2-methylpropyl [4-(tetrahydro-4-hydroxy-2H-thiopyran-4-yl)phenyl]carbamate A solution of 2-methylpropyl 4-bromophenylcarbamate (Step 1, 10.0 g, 36.7 mmol) in anhydrous tetrahydrofuran (184 mL) at −78° C. under $N_2$ was treated n-butyllithium (1.6M in hexanes, 48.2 mL, 77.1 mmol) dropwise over 20 mins, and the mixture was stirred at −78° C. for 45 mins. The resulting slurry was then treated with a solution of tetrahydro-2H-thiopyran-4-one (4.48 g, 38.5 mmol) in anhydrous tetrahydrofuran (38 mL) dropwise over 5 mins to give an opaque mixture which was allowed to slowly warm to 0° C. with stirring over approximately 2.5 hrs. The mixture was then quenched by the slow addition of saturated aqueous ammonium chloride (75 mL), water (75 mL) was added, and the layers were separated. The organic phase was washed with water (50 mL) and saline (50 mL), dried over anhydrous magnesium sulfate and concentrated under reduced pressure, and the crude product was recrystallized from EtOAc/hexanes to give the title compound, mp 150–151° C.; MS (ESI−) for $C_{16}H_{23}NO_3S$ m/z 308 (M−H)$^−$.

Step 3: Preparation of 2-methylpropyl [4-(tetrahydro-2H-thiopyran-4-yl)phenyl]carbamate Following the general procedure of EXAMPLE 456, Step 1, and making non-critical variations but substituting 2-methylpropyl [4-(tetrahydro-4-hydroxy-2H-thiopyran-4-yl)phenyl]carbamate (Step 2) for 2-methylpropyl [3-fluoro-4-(tetrahydro-4-hydroxy-2H-thiopyran-4-yl)phenyl]carbamate and purifying the product by recrystallization from EtOAc/hexanes, the title compound was obtained, mp 126–128° C.; MS (ESI–) for $C_{16}H_{23}NO_2S$ m/z 292 (M–H)⁻.

Step 4: Preparation of 4-(tetrahydro-2H-thiopyran-4-yl)benzenamine

Following the general procedure of EXAMPLE 456, Step 2, and making non-critical variations but substituting 2-methylpropyl [4-(tetrahydro-2H-thiopyran-4-yl)phenyl]carbamate (Step 3) for 2-methylpropyl [3-fluoro-4-(tetrahydro-2H-thiopyran-4-yl)phenyl]carbamate, the title compound was obtained, mp 103–106° C.; MS (ESI+) for $C_{11}H_{15}NS$ m/z 194 (M+H)⁺.

Step 5: Preparation of butyl (5R)-3-[4-(tetrahydro-2H-thiopyran-4-yl)phenyl]-2-oxo-5-oxazolidinecarboxylate Following the general procedure of EXAMPLE 452, Step 1, and making non-critical variations but substituting 4-(tetrahydro-2H-thiopyran-4-yl)benzenamine (Step 4) for 4-(4-thiomorpholinyl)aniline, the title compound was obtained, mp 94–96° C.; MS (ESI+) for $C_{19}H_{25}NO_4S$ m/z 364 (M+H)⁺.

Step 6: Preparation of butyl (SR)-3-[4-(tetrahydro-2H-thiopyran-4-yl)phenyl]-2-oxo-5-oxazolidinecarboxylate S,S-dioxide Following the general procedure of EXAMPLE 452, Step 2, and making non-critical variations but substituting butyl (5R)-3-[4-(tetrahydro-2H-thiopyran-4-yl)phenyl]-2-oxo-5-oxazolidinecarboxylate (Step 5) for butyl (5R)-3-[4-(thiomorpholin-4-yl)phenyl]-2-oxo-5-oxazolidinecarboxylate, the title compound was obtained, mp 176–179° C.; MS (ESI+) for $C_{19}H_{25}NO_6S$ m/z 396 (M+H)⁺.

Step 7: Preparation of (5R)-(–)-3-[4-(tetrahydro-2H-thiopyran-4-yl)phenyl]-2-oxo-5-oxazolidinecarboxamide S,S-dioxide Following the general procedure of EXAMPLE 452, Step 3, and making non-critical variations, but substituting butyl (5R)-3-[4-(tetrahydro-2H-thiopyran-4-yl)phenyl]-2-oxo-5-oxazolidinecarboxylate S,S-dioxide (Step 6) for butyl (5R)-3-[4-(thiomorpholin-4-yl)phenyl]-2-oxo-5-oxazolidinecarboxylate S,S-dioxide, the title compound was obtained, mp 211–212° C.; MS (ESI–) for $C_{15}H_{18}N_2O_5S$ m/z 337 (M–H)⁻; $[\alpha]^{25}_D$ –19 (c 0.95, DMSO)

EXAMPLE 459

(5R)-3-[4-(cis-tetrahydro-1-oxido-2H-thiopyran-4-yl)phenyl]-2-oxo-S-oxazolidinecarboxamide

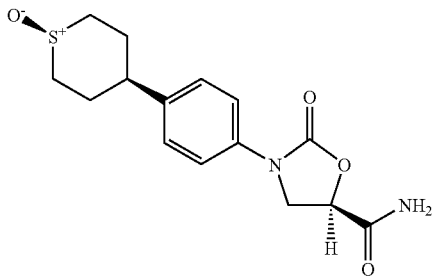

Step 1: Preparation of butyl (5R)-3-[4-(cis-tetrahydro-1-oxido-2H-thiopyran-4-yl)phenyl]-2-oxo-5-oxazolidinecarboxylate Following the general procedure of EXAMPLE 459, Step 1, and making non-critical variations but substituting butyl (SR)-3-[4-(tetrahydro-2H-thiopyran-4-yl)phenyl]-2-oxo-5-oxazolidinecarboxylate (EXAMPLE 458, Step 5) for butyl (5R)-3-[4-(thiomorpholin-4-yl)phenyl]-2-oxo-5-oxazolidinecarboxylate, a mixture of the cis and trans sulfoxide products in approximately a 2:1 ratio was obtained. Subsequent purification by preparative HPLC (Chiralcel OD column, EtOH eluent) followed by recrystallization from EtOAc/hexanes provided the title compound, mp 127–130° C.; MS (ESI+) for $C_{19}H_{25}NO_5S$ m/z 380 (M+H)⁺.

Step 2: Preparation of (5R)-3-[4-(cis-tetrahydro-1-oxido-2H-thiopyran-4-yl)phenyl]-2-oxo-5-oxazolidinecarboxamide Following the general procedure of EXAMPLE 452, Step 3, and making non-critical variations, but substituting butyl (5R)-3-[4-(cis-tetrahydro-1-oxido-2H-thiopyran-4-yl)phenyl]-2-oxo-5-oxazolidinecarboxylate (Step 1) for butyl (5R)-3-[4-(thiomorpholin-4-yl)phenyl]-2-oxo-5-oxazolidinecarboxylate S,S-dioxide, the title compound was obtained, mp 269–273° C. (dec.); MS (ESI–) for $C_{15}H_{18}N_2O_4S$ m/z 321 (M–H)⁻.

EXAMPLE 460

(SR)-3-[4-(trans-tetrahydro-1-oxido-2H-thiopyran-4-yl)phenyl]-2-oxo-5-oxazolidinecarboxamide

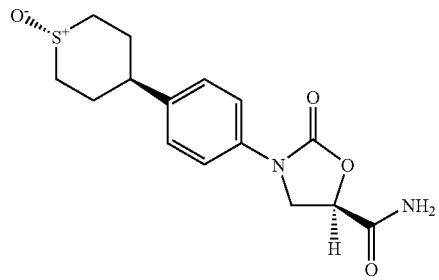

Step 1: Preparation of butyl (5R)-3-[4-(trans-tetrahydro-1-oxido-2H-thiopyran-4-yl)phenyl]-2-oxo-5-oxazolidinecarboxylate Following the general procedure of EXAMPLE 454, Step 1, and making non-critical variations but substituting butyl (SR)-3-[4-(tetrahydro-2H-thiopyran-4-yl)phenyl]-2-oxo-5-oxazolidinecarboxylate (EXAMPLE 458, Step 5) for butyl (5R)-3-[4-(thiomorpholin-4-yl)phenyl]-2-oxo-5-oxazolidinecarboxylate, a mixture of the cis and trans sulfoxide products in approximately a 2:1 ratio was obtained. Subsequent purification by preparative HPLC (Chiralcel OD column, EtOH eluent) followed by recrystallization from EtOAc/hexanes provided the title compound, mp 115–117° C.; MS (ESI+) for $C_{19}H_{25}NO_5S$ m/z 380 (M+H)⁺.

Step 2: Preparation of (5R)-3-[4-(trans-tetrahydro-1-oxido-2H-thiopyran-4-yl)phenyl]-2-oxo-5-oxazolidinecarboxamide Following the general procedure of EXAMPLE 452, Step 3, and making non-critical variations, but substituting butyl (5R)-3-[4-(trans-tetrahydro-1-oxido-2H-thiopyran-4-yl)phenyl]-2-oxo-5-oxazolidinecarboxylate (Step 1) for butyl (5R)-3-[4-(thiomorpholin-4-yl)phenyl]-2-oxo-5-oxazolidinecarboxylate S,S-dioxide, the title compound was obtained, mp 174–175° C.; MS (ESI–) for $C_{15}H_{18}N_2O_4S$ m/z 321 (M–H)⁻.

EXAMPLE 461

(5R)-3-[4-(Tetrahydro-2H-thiopyran-4-yl)-3-fluorophenyl]-2-oxo-5-oxazolidinecarboxamide S,S-dioxide—Method B

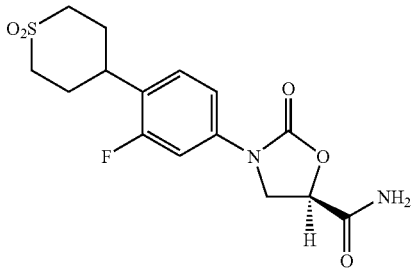

Step 1: Preparation of 2-methylpropyl [4-(tetrahydro-1,1-dioxido-2H-thiopyran-4-yl)-3-fluorophenyl]carbamate Following the general procedure of EXAMPLE 452, Step 2, and making non-critical variations but substituting 2-methylpropyl [4-(tetrahydro-2H-thiopyran-4-yl)-3-fluorophenyl]carbamate (EXAMPLE 456, Step 1) for butyl (5R)-3-[4-(thiomorpholin-4-yl)phenyl]-2-oxo-5-oxazolidinecarboxylate, the title compound is obtained, $^1$H NMR (CDCl$_3$) (δ) 7.36 (bd, 1H), 7.14 (t, 1H), 6.99 (m, 1H), 6.70 (bs, 1H), 3.95 (d, 2H), 3.14 (m, 4H), 3.07 (m, 1H), 2.38 (m, 2H), 2.18 (m, 2H), 1.95 (m,1H), 0.96 (d, 6H).

Step 2: Preparation of (5R)-3-[4-(tetrahydro-2H-thiopyran-4-yl)-3-fluorophenyl]-5-hydroxymethyl-2-oxazolidinone S,S-dioxide A solution of 2-methylpropyl [4-(tetrahydro-1,1-dioxido-2H-thiopyran-4-yl)-3-fluorophenyl]carbamate (Step 1, 2.00 g, 5.82 mmol) in dry tetrahydrofuran at −78° C. under N$_2$ was treated with n-butyllithium (1.6M in hexanes, 3.82 mL, 6.11 mmol) dropwise and stirred at −78° C. for 45 mins. Then, (R)-glycidyl butyrate (0.86 mL, 6.11 mmol) was added dropwise, and the resulting mixture was stirred at −78° C. for 30 mins and at ambient temperature for 2.75 days. The reaction mixture was then quenched with saturated aqueous ammonium chloride (15 mL), diluted with water (15 mL) and EtOAc (25 mL), and the layers were separated. The organic phase was diluted with small amounts of methylene chloride, methanol and tetrahydrofuran in an attempt to dissolve a precipitate that had formed and was then washed with water (20 mL) and saline (20 mL), dried over anhydrous sodium sulfate and concentrated under reduced pressure. The resulting solid was then diluted with hot methanol/EtOAc (1:5, 100 mL), followed by hexanes (150 mL), and filtered to give the title compound, $^1$H NMR (DMSO) (δ) 7.51 (dd, 1H), 7.37 (t, 1H), 7.30 (m, 1H), 5.21 (t, 1H), 4.70 (m, 1H), 4.07 (t, 1H), 3.81 (dd, 1H), 3.65 (m, 1H), 3.55 (m, 1H), 3.37 (m, 2H), 3.20 (m, 1H), 3.10 (m, 2H), 2.15 (m, 2H), 2.03 (m, 2H).

Step 3: Preparation of methyl (5R)-3-[4-(tetrahydro-2H-thiopyran-4-yl)-3-fluorophenyl]-2-oxo-5-oxazolidinecarboxylate S,S-dioxide A mixture of ruthenium(III) trichloride (29 mg, 0.139 mmol, 4 mol %), sodium periodate (3.21 g, 15.0 mmol), and sodium dihydrogen phosphate monohydrate (2.60 g, 18.8 mmol) in water/methylene chloride (10:1, 21 mL) was treated with a suspension of (5R)-3-[4-(tetrahydro-2H-thiopyran-4-yl)-3-fluorophenyl]-5-hydroxymethyl-2-oxazolidinone S,S-dioxide (Step 2, 1.20 g, 3.49 mmol) in acetonitrile (35 mL), and the resulting mixture was stirred at ambient temperature for 24 hrs and was then adjusted to pH 2 with aqueous hydrochloric acid (1M) and extracted with methylene chloride (3×100 mL). The combined organic phase was dried over anhydrous sodium sulfate and concentrated under reduced pressure, and the residue was flushed through a Flash 40M 90 g silica gel cartridge with a gradient of CH$_3$CN/CH$_2$Cl$_2$ (20/80–40/60) containing 1% formic acid. Those fractions containing the carboxylic acid intermediate (920 mg total) were pooled and concentrated, and the white solid was dissolved in methanol (25 mL) and treated with 3 to 4 drops of concentrated sulfuric acid. The resulting mixture was stirred at ambient temperature for 4 hrs and was then concentrated under reduced pressure and chromatographed on a Flash 40S 40 g silica gel cartridge, eluting with a gradient of MeOH/CH$_2$Cl$_2$ (1/99–2/98). Pooling and concentration of those fractions with an R$_f$=0.53 by TLC (MeOH/CH$_2$Cl$_2$, 5/95) provided the title compound as an amorphous solid, $^1$H NMR (CDCl$_3$) (δ) 7.50 (dd, 1H), 7.25 (t, 1H), 7.15 (m, 1H), 5.09 (dd, 1H), 4.27 (t, 1H), 4.13 (dd, 1H), 3.88 (s, 3H), 3.15 (m, 4H), 3.11 (m, 1H), 2.40 (m, 2H), 2.19 (m, 2H).

Step 4: Preparation of (SR)-3-[4-(tetrahydro-2H-thiopyran-4-yl)-3-fluorophenyl]-2-oxo-5-oxazolidinecarboxamide S,S-dioxide Following the general procedure of EXAMPLE 452, Step 3, and making non-critical variations but substituting methyl (5R)-3-[4-(tetrahydro-2H-thiopyran-4-yl)-3-fluorophenyl]-2-oxo-5-oxazolidinecarboxylate S,S-dioxide (Step 3) for butyl (5R)-3-[4-(thiomorpholin-4-yl)phenyl]-2-oxo-5-oxazolidinecarboxylate S,S-dioxide and purifying the product by trituration and filtration from (5% MeOH/CH$_2$Cl$_2$)/Et$_2$O, the title compound was obtained, mp 231–234° C. (dec.); MS (ESI−) for C$_{15}$H$_{17}$FN$_2$O$_5$S m/z 355 (M−H)$^−$.

Additional Examples of amide-containing compounds that can be used in the present invention are disclosed below.

EXAMPLE 462

N-{3-[3-fluoro-4-(5-oxo-5,6-dihydro-4H-[1,3,4]thiadiazin-2-yl)-phenyl]-2-oxo-oxazolidin-5(S)-ylmethyl}-acetamide

EXAMPLE 463

N-{3-[3-fluoro-4-(6(S)-methyl-5-oxo-5,6-dihydro-4H-[1,3,4]thiadiazin-2-yl)-phenyl]-2-oxo-oxazolidin-5(S)-ylmethyl}-acetamide

EXAMPLE 464

N-{3-[3-fluoro-4-(6(R)-methyl-5-oxo-5,6-dihydro-4H-[1,3,4]thiadiazin-2-yl)-phenyl]-2-oxo-oxazolidin-5(S)-ylmethyl}-acetamide

EXAMPLE 465

N-{3-[3-fluoro-4-(5-oxo-5,6-dihydro-4H-[1,3,4]thiadiazin-2-yl)-phenyl]-2-oxo-oxazolidin-5 (S)-ylmethyl}-propionamide

EXAMPLE 466 cyclopropanecarboxylic acid {3-[3-fluoro-4-(5-oxo-5,6-dihydro-4H-[1,3,4]thiadiazin-2-yl)-phenyl]-2-oxo-oxazolidin-5(S)-ylmethyl}-amide

EXAMPLE 467

N-{3-[3-fluoro-4-(5-oxo-5,6-dihydro-4H-[1,3,4]thiadiazin-2-yl)-phenyl]-2-oxo-oxazolidin-5 (S)-ylmethyl}-thioacetamide

EXAMPLE 468

N-{3-[3-fluoro-4-(5-thioxo-5,6-dihydro-4H-[1,3,4]
thiadiazin-2-yl)-phenyl]-2-oxo-oxazolidin-5 (S)-
ylmethyl}-thioacetamide

EXAMPLE 469

N-{3-[3-fluoro-4-(5-oxo-5,6-dihydro-4H-[1,3,4]
thiadiazin-2-yl)-phenyl]-2-oxo-oxazolidin-5 (S)-
ylmethyl}-acetamide

EXAMPLE 470

N-{3-[3-fluoro-4-(5-oxo-5,6-dihydro-4H-[1,3,4]
thiadiazin-2-yl)-phenyl]-2-oxo-oxazolidin-5-
ylmethyl}-3-(4-hydroxy-phenyl)-acrylamide

EXAMPLE 471

N-{3-[4-(6,6-dimethyl-5-oxo-5,6-dihydro-4H-[1,3,4]
thiadiazin-2-yl)-3-fluoro-phenyl]-2-oxo-oxazolidin-5
(S)-ylmethyl}-acetamide

EXAMPLE 472

N-{3-[3-fluoro-4-(6-ethyl-5-oxo-5,6-dihydro-4H-[1,
3,4]thiadiazin-2-yl)-phenyl]-2-oxo-oxazolidin-5(S)-
ylmethyl}-acetamide

EXAMPLE 473

N-{3-[3-fluoro-4-(9-oxo-5-thia-7,8-diaza-spiro[3.5]
non-6-en-6-yl)-phenyl]-2-oxo-oxazolidin-5(S)-
ylmethyl}-acetamide

EXAMPLE 474

N-{3-[3-fluoro-4-(5-oxo-6-phenyl-5,6-dihydro-4H-
[1,3,4]thiadiazin-2-yl)-phenyl]-2-oxo-oxazolidin-5
(S)-ylmethyl}-acetamide

EXAMPLE 475

N-{3-[3-fluoro-4-(5-oxo-5,6-dihydro-4H-[1,3,4]
thiadiazin-2-yl)-phenyl]-2-oxo-oxazolidin-5(S)-
ylmethyl}-2-hydroxy-acetamide

EXAMPLE 476

N-{3-[3-fluoro-4-(5-oxo-5,6-dihydro-4H-[1,3,4]
thiadiazin-2-yl)-phenyl]-2-oxo-oxazolidin-5(S)-
ylmethyl}-3-oxo-butyramide

EXAMPLE 477

N-{3-[3-fluoro-4-(5-oxo-5,6-dihydro-4H-[1,3,4]
thiadiazin-2-yl)-phenyl]-2-oxo-oxazolidin-5(S)-
ylmethyl}-3-(4-fluoro-phenyl)-3-oxo-propionamide,

EXAMPLE 478

N-{3-[3-fluoro-4-(5-oxo-5,6-dihydro-4H-[1,3,4]
thiadiazin-2-yl)-phenyl]-2-oxo-oxazolidin-5(S)-
ylmethyl}-3-[4-(hydroxyimino-methyl)-phenyl]-
acrylamide

EXAMPLE 479

N-{3-[3-fluoro-4-(5-oxo-5,6-dihydro-4H-[1,3,4]
thiadiazin-2-yl)-phenyl]-2-oxo-oxazolidin-5(S)-
ylmethyl}-3-[4-(methoxyimino-methyl)-phenyl]-
acrylamide

EXAMPLE 480

N-{3-[4-(6,6-dimethyl-1,1,5-trioxo-1,4,5,6-
tetrahydro-1$^{\delta6}$-[1,3,4]thiadiazin-2-yl)-3-fluoro-
phenyl]-2-oxo-oxazolidin-5(S)-ylmethyl}-acetamide

EXAMPLE 481

N-{3-[3-fluoro-4-(4-methyl-5-oxo-5,6-dihydro-4H-
[1,3,4]thiadiazin-2-yl)-phenyl]-2-oxo-oxazolidin-5
(S)-ylmethyl}-acetamide

EXAMPLE 482

N-{3-[3-fluoro-4-(5-oxo-6-propyl-5,6-dihydro-4H-
[1,3,4]thiadiazin-2-yl)-phenyl]-2-oxo-oxazolidin-5
(S)-ylmethyl}-acetamide

EXAMPLE 483

N-{3-[3-fluoro-4-(6-isopropyl-5-oxo-5,6-dihydro-
4H-[1,3,4]thiadiazin-2-yl)-phenyl]-2-oxo-
oxazolidin-5(S)-ylmethyl}-acetamide

EXAMPLE 484

N-{3-[3-fluoro-4-(6-fluoro-5-oxo-5,6-dihydro-4H-
[1,3,4]thiadiazin-2-yl)-phenyl]-2-oxo-oxazolidin-5
(S)-ylmethyl}-acetamide

EXAMPLE 485

N-{3-[3-fluoro-4-(6-hydroxymethyl-5-oxo-5,6-
dihydro-4H-[1,3,4]thiadiazin-2-yl)-phenyl]-2-oxo-
oxazolidin-5(S)-ylmethyl}-acetamide

EXAMPLE 486

N-{3-[3-fluoro-4-(6-(2-hydroxy-ethyl)-5-oxo-5,6-
dihydro-4H-[1,3,4]thiadiazin-2-yl)-phenyl]-2-oxo-
oxazolidin-5(S)-ylmethyl}-acetamide

EXAMPLE 487

N-(3-{3-fluoro-4-(6-(4-hydroxy-phenyl)-5-oxo-5,6-
dihydro-4H-[1,3,4]thiadiazin-2-yl]-phenyl}-2-oxo-
oxazolidin-5(S)-ylmethyl)-acetamide

EXAMPLE 488

N-{3-[4-(6,6-dimethyl-1,5-dioxo-1,4,5,6-tetrahydro-
1$^{\delta4}$-[1,3,4]-thiadiazin-2-yl)-3-fluoro-phenyl]-2-oxo-
oxazolidin-5(S)-ylmethyl}-acetamide

EXAMPLE 489

N-[[(5S)-3-[4-(3,4-dihydro-2H-thiopyran-4-yl)-3-
fluorophenyl]-2-oxo-5-oxazolidinyl]methyl]-2,2,2-
trifluoroacetamide

EXAMPLE 490

N-[[(5S)-3-[4-(3,4-dihydro-2H-thiopyran-4-yl)-3-
fluorophenyl]-2-oxo-5-oxazolidinyl]methyl]
acetamide

EXAMPLE 491

N-[[(5S)-3-[4-(3,4-dihydro-2H-thiopyran-4-yl)-3-
fluorophenyl]-2-oxo-5-oxazolidinyl]methyl]
ethanethioamide

EXAMPLE 492

N-[[(5S)-3-[4-(3,4-dihydro-1-oxido-2H-thiopyran-4-
yl)-3-fluorophenyl]-2-oxo-5-oxazolidinyl]methyl]
acetamide

EXAMPLE 493

N-[[(5S)-3-[4-(3,4-dihydro-1,1-dioxido-2H-
thiopyran-4-yl)-3-fluorophenyl]-2-oxo-5-
oxazolidinyl]methyl]acetamide

EXAMPLE 494

N-[[(5S)-3-[4-(3,4-dihydro-1-oxido-2H-thiopyran-4-
yl)-3-fluorophenyl]-2-oxo-5-oxazolidinyl]methyl]
ethanethioamide,

EXAMPLE 495

N-[[(5S)-3-[4-(2,3-dihydro-1,1-dioxido-4H-1,4-
thiazin-4-yl)-3-fluorophenyl]-2-oxo-5-oxazolidinyl]
methyl]acetamide

EXAMPLE 496

N-[[(5S)-3-[4-(2,3-dihydro-1,1-dioxido-4H-1,4-thiazin-4-yl)-3,5-difluorophenyl]-2-oxo-5-oxazolidinyl]methyl]acetamide

EXAMPLE 497

N-[[(5S)-3-[4-(3,4-dihydro-1,1-dioxido-2H-thiopyran-4-yl)-3-fluorophenyl]-2-oxo-5-oxazolidinyl]methyl]-2,2-difluoroacetamide

EXAMPLE 498

N-[[(5S)-3-[4-(3,4-dihydro-1,1-dioxido-2H-thiopyran-4-yl)-3-fluorophenyl]-2-oxo-5-oxazolidinyl]methyl]-2,2-difluoroethanethioamide

EXAMPLE 499

2,2-Dichloro-N-[[(5S)-3-[4-(3,4-dihydro-1,1-dioxido-2H-thiopyran-4-yl)-3-fluorophenyl]-2-oxo-5-oxazolidinyl]methyl]acetamide

EXAMPLE 500

N-[[(5S)-3-[4-(3,4-dihydro-4-hydroxy-1,1-dioxido-2H-thiopyran-4-yl)-3-fluorophenyl]-2-oxo-5-oxazolidinyl]methyl]acetamide

EXAMPLE 501

N-[[(5S)-3-[3-Fluoro-4-(4-fluoro-3,4-dihydro-1,1-dioxido-2H-thiopyran-4-yl)phenyl]-2-oxo-5-oxazolidinyl]methyl]acetamide

EXAMPLE 502

N-[[(5S)-3-[4-(3,4-dihydro-1,1-dioxido-2H-thiopyran-4-yl)phenyl]-2-oxo-5-oxazolidinyl]methyl]acetamide

EXAMPLE 503

N-[[(5S)-3-[4-(3,4-dihydro-1,1-dioxido-2H-thiopyran-4-yl)phenyl]-2-oxo-5-oxazolidinyl]methyl]-2,2-difluoroacetamide,

EXAMPLE 504

2,2-dichloro-N-[[(5S)-3-[4-(3,4-dihydro-1,1-dioxido-2H-thiopyran-4-yl)phenyl]-2-oxo-5-oxazolidinyl]methyl]acetamide

EXAMPLE 505

[[(5S)-3-[4-(3,4-dihydro-1,1-dioxido-2H-thiopyran-4-yl)phenyl]-2-oxo-5-oxazolidinyl]methyl]-2,2-difluoroethanethioamide

EXAMPLE 506

N-[[(5S)-3-[4-(3,4-dihydro-1,1-dioxido-2H-thiopyran-4-yl)phenyl]-2-oxo-5-oxazolidinyl]methyl]propionamide

EXAMPLE 507

N-[[(5S)-3-[4-(3,4-dihydro-1,1-dioxido-2H-thiopyran-4-yl)-3,5-difluorophenyl]-2-oxo-5-oxazolidinyl]methyl]acetamide

EXAMPLE 508

N-[[(5S)-3-[4-(2,3-dihydro-1,1-dioxido-4H-1,4-thiazin-4-yl)-3-fluorophenyl]-2-oxo-5-oxazolidinyl]methyl]-2,2-difluoroethanethioamide

EXAMPLE 509

2,2-dichloro-N-[[(5S)-3-[4-(2,3-dihydro-1,1-dioxido-4H-1,4-thiazin-4-yl)-3-fluorophenyl]-2-oxo-5-oxazolidinyl]methyl]acetamide

EXAMPLE 510

N-[[(5S)-3-[4-(2,3-dihydro-1,1-dioxido-4H-1,4-thiazin-4-yl)-3-fluorophenyl]-2-oxo-5-oxazolidinyl]methyl]-2,2-difluoroacetamide

EXAMPLE 511

N-[[(5S)-3-[4-(2,3-dihydro-1,1-dioxido-4H-1,4-thiazin-4-yl)phenyl]-2-oxo-5-oxazolidinyl]methyl]-2,2-difluoroethanethioamide

EXAMPLE 512

2,2-dichloro-N-[[(5S)-3-[4-(2,3-dihydro-1,1-dioxido-4H-1,4-thiazin-4-yl)phenyl]-2-oxo-5-oxazolidinyl]methyl]acetamide

EXAMPLE 513

N-[[(5S)-3-[4-(2,3-dihydro-1l1-dioxido-4H-1,4-thiazin-4-yl)phenyl]-2-oxo-5-oxazolidinyl]methyl]-2,2-difluoroacetamide

EXAMPLE 514

N-[[(5S)-3-[4-(2,3-Dihydro-1,1-dioxido-4H-1,4-thiazin-4-yl)-3,5-difluorophenyl]-2-oxo-5-oxazolidinyl]methyl]-2,2-difluoroethanethioamide

EXAMPLE 515

2,2-dichloro-N-[[(5S)-3-[4-(2,3-dihydro-1,1-dioxido-4H-1,4-thiazin-4-yl)-3,5-difluorophenyl]-2-oxo-5-oxazolidinyl]methyl]acetamide, or

EXAMPLE 516

N-[[(5S)-3-[4-(2,3-dihydro-1,1-dioxido-4H-1,4-thiazin-4-yl)-3,5-difluorophenyl]-2-oxo-5-oxazolidinyl]methyl]-2,2-difluoroacetamide

EXAMPLE 517

N-[[(5S)-3-[4-(2,3-dihydro-1,1-dioxido-4H-1,4-thiazin-4-yl)-3-fluorophenyl]-2-oxo-5-oxazolidinyl]methyl]acetamide

EXAMPLE 518

2,2-dichloro-N-[[(5S)-3-[4-(3,4-dihydro-1,1-dioxido-2H-thiopyran-4-yl)-3-fluorophenyl]-2-oxo-5-oxazolidinyl]methyl]acetamide

EXAMPLE 519

2,2-dichloro-N-[[(5S)-3-[4-(3,4-dihydro-1,1-dioxido-2H-thiopyran-4-yl)phenyl]-2-oxo-5-oxazolidinyl]methyl]acetamide

EXAMPLE 520

2,2-dichloro-N-[[(5S)-3-[4-(2,3-dihydro-1,1-dioxido-4H-1,4-thiazin-4-yl)-3-fluorophenyl]-2-oxo-5-oxazolidinyl]methyl]acetamide

EXAMPLE 521

2,2-dichloro-N-[[(5S)-3-[4-(2,3-dihydro-1,1-dioxido-4H-1,4-thiazin-4-yl)phenyl]-2-oxo-5-oxazolidinyl]methyl]acetamide

EXAMPLE 522

N-[[(5S)-3-[4-(2,3-dihydro-1,1-dioxido-4H-1,4-thiazin-4-yl)-3,5-difluorophenyl]-2-oxo-5-oxazolidinyl]methyl]acetamide

EXAMPLE 523

N-[[(5S)-3-[4-(3,4-dihydro-1,1-dioxido-2H-thiopyran-4-yl)-3-fluorophenyl]-2-oxo-5-oxazolidinyl]methyl]-2,2-difluoroacetamide

EXAMPLE 524

N-[[(5S)-3-[4-(3,4-dihydro-1,1-dioxido-2H-thiopyran-4-yl)-3-fluorophenyl]-2-oxo-5-oxazolidinyl]methyl]-2,2-difluoroethanethioamide

EXAMPLE 525

N-[[(5S)-3-[4-(3,4-dihydro-1,1-dioxido-2H-thiopyran-4-yl)phenyl]-2-oxo-5-oxazolidinyl]methyl]-2,2-difluoroacetamide

EXAMPLE 526

N-[[(5S)-3-[4-(2,3-dihydro-1,1-dioxido-4H-1,4-thiazin-4-yl)-3-fluorophenyl]-2-oxo-5-oxazolidinyl]methyl]-2,2-difluoroethanethioamide

EXAMPLE 527

N-[[(5S)-3-[4-(2,3-dihydro-1,1-dioxido-4H-1,4-thiazin-4-yl)-3-fluorophenyl]-2-oxo-5-oxazolidinyl]methyl]-2,2-difluoroacetamide

EXAMPLE 528

N-[[(5S)-3-[4-(2,3-dihydro-1,1-dioxido-4H-1,4-thiazin-4-yl)phenyl]-2-oxo-5-oxazolidinyl]methyl]-2,2-difluoroethanethioamide, or

EXAMPLE 529

2,2-dichloro-N-[[(5S)-3-[4-(2,3-dihydro-1,1-dioxido-4H-1,4-thiazin-4-yl)-3,5-difluorophenyl]-2-oxo-5-oxazolidinyl]methyl]acetamide,

EXAMPLE 530

(S)-N-[[3-[3-fluoro-4-(1,2,3,4,6,7-hexahydro-5-oxo-1,4-diazepin-1-yl)phenyl]-2-oxo-5-oxazolidinyl]methyl]acetamide

EXAMPLE 531

(S)-N-[[3-[3-fluoro-4-(1,2,3,4,6,7-hexahydro-5-oxo-1,4-diazepin-1-yl)phenyl]-2-oxo-5-oxazolidinyl]methyl]thioacetamide

EXAMPLE 532

(S)-N-[[3-[3-fluoro-4-(1,2,3,4,6,7-hexahydro-4-methyl-5-oxo-1,4-diazepin-1-yl)phenyl]-2-oxo-5-oxazolidinyl]methyl]acetamide, or

EXAMPLE 533

(S)-N-[[3-[3-fluoro-4-(1,2,3,4,6,7-hexahydro-4-methyl-5-oxo-1,4-diazepin-1-yl)phenyl]-2-oxo-5-oxazolidinyl]methyl]thioacetamide

EXAMPLE 534

N-[[(5S)-3-[3-fluoro-4-[tetrahydro-1,1-dioxido-2-(2-propenyl)-2H-1,2-thiazin-4-yl]phenyl]-2-oxo-5-oxazolidinyl]methyl]acetamide

EXAMPLE 535

N-[[(5S)-3-[3-fluoro-4-(tetrahydro-1,1-dioxido-2H-1,2-thiazin-4-yl)phenyl]-2-oxo-5-oxazolidinyl]methyl]acetamide

EXAMPLE 536

N-[[(5S)-3-[3-fluoro-4-(tetrahydro-1,1-dioxido-2H-1,2-thiazin-4-yl)phenyl]-2-oxo-5-oxazolidinyl]methyl]ethanethioamide

EXAMPLE 537

N-[[(5S)-3-[-fluoro-4-(tetrahydro-2-methyl-1,1-dioxido-2H-1,2-thiazin-4-yl)phenyl]-2-oxo-5-oxazolidinyl]methyl]ethanethioamide

EXAMPLE 538

N-[[(5S)-3-[4-(2,2-dioxido-1,2-oxathian-5-yl)-3-fluorophenyl]-2-oxo-5-oxazolidinyl]methyl]ethanethioamide,

EXAMPLE 539

N-[[(5S)-3-[4-(1,1-dioxido-4-isothiazolidinyl)-3-fluorophenyl]-2-oxo-5-oxazolidinyl]methyl]ethanethioamide, or

EXAMPLE 540

N-[[(5S)-3-[3-fluoro-4-(tetrahydro-2-methyl-1,1-dioxido-2H-1,2-thiazin-4-yl)phenyl]-2-oxo-5-oxazolidinyl]methyl]acetamide

EXAMPLE 541

N-({(5S)-3-[(2R)-1-(2-fluoroethyl)-2-methyl-2,3-dihydro-1H-indol-5-yl]-2-oxo-1,3-oxazolidin-5-yl}methyl)acetamide

EXAMPLE 542

N-{[(5S)-3-((2R)-1-glycoloyl-2-methyl-2,3-dihydro-1H-indol-5-yl)-2-oxo-1,3-oxazolidin-5-yl]methyl}acetamide

EXAMPLE 543

N-({(5S)-3-[(2R)-1-glycoloyl-2-methyl-2,3-dihydro-1H-indol-5-yl]-2-oxo-1,3-oxazolidin-5-yl}methyl)acetamide

EXAMPLE 544

N-({(5S)-3-[(2R)-1-formyl-2-methyl-2,3-dihydro-1H-indol-5-yl]-2-oxo-1,3-oxazolidin-5-yl}methyl)acetamide

EXAMPLE 545

N-({(5S)-3-[(2R)-1-formyl-2-methyl-2,3-dihydro-1H-indol-5-yl]-2-oxo-1,3-oxazolidin-5-yl}methyl)propanamide

EXAMPLE 546

N-({(5S)-3-[(2R)-1-formyl-2-methyl-2,3-dihydro-1H-indol-5-yl]-2-oxo-1,3-oxazolidin-5-yl}methyl)ethanethioamide

EXAMPLE 547

N-({(5S)-3-[(2R)-1-(2-methoxyacetyl)-2-methyl-2,3-dihydro-1H-indol-5-yl]-2-oxo-1,3-oxazolidin-5-yl}methyl)acetamide

EXAMPLE 548

N-({(5S)-3-[(2R)-1-acetyl-2-methyl-2,3-dihydro-1H-indol-5-yl]-2-oxo-1,3-oxazolidin-5-yl}methyl)acetamide

EXAMPLE 549

N-[((5S)-3-{(2R)-2-methyl-1-[(methylamino)carbothioyl]-2,3-dihydro-1H-indol-5-yl}-2-oxo-1,3-oxazolidin-5-yl)methyl]acetamide

EXAMPLE 550

N-({(5S)-3-[(2R)-1-glycoloyl-2-methyl-2,3-dihydro-1H-indol-5-yl]-2-oxo-1,3-oxazolidin-5-yl}methyl)ethanethioamide

EXAMPLE 551

N-{[(5S)-3-[(2R)-1-formyl-2-methyl-1,2,3,4-tetrahydro-6-quinolinyl]-2-oxo-1,3-oxazolidin-5-yl]methyl}acetamide

EXAMPLE 552

N-{[(5S)-3-[(2R)-1-glycoloyl-2-methyl-1,2,3,4-tetrahydro-6-quinolinyl]-2-oxo-1,3-oxazolidin-5-yl]methyl}acetamide

EXAMPLE 553

N-({(5S)-3-[(2R)-1-formyl-2-methyl-1,2,3,4-tetrahydro-6-quinolinyl]-2-oxo-1,3-oxazolidin-5-yl}methyl)acetamide

EXAMPLE 554

N-({(5S)-3-[(2R)-1-formyl-2-methyl-1,2,3,4-tetrahydro-6-quinolinyl]-2-oxo-1,3-oxazolidin-5-yl}methyl)ethanethioamide

EXAMPLE 555

N-{[(5S)-3-[(3R)$_4$-Formyl-3-methyl-3,4-dihydro-2H-1,4-benzoxazin-7-yl]-2-oxo-1,3-oxazolidin-5-yl]methyl}acetamide

EXAMPLE 556

N-({(5S)-3-[(3R)-4-Formyl-3-methyl-3,4-dihydro-2H-1,4-benzoxazin-7-yl]-2-oxo-1,3-oxazolidin-5-yl}methyl)acetamide

EXAMPLE 557

N-({(5S)-3-[(3R)-4-Formyl-3-methyl-3,4-dihydro-2H-1,4-benzoxazin-7-yl]-2-oxo-1,3-oxazolidin-5-yl}methyl)ethanethioamide

EXAMPLE 558

N-({(5S)-3-[(2R)$_2$-(fluoromethyl)-1-formyl-2,3-dihydro-1H-indol-5-yl]-2-oxo-1,3-oxazolidin-5-yl}methyl)acetamide

EXAMPLE 559

N-{[(5R)-3-(2(+)-methyl-2,3-dihydro-1-benzothien-5-yl)-2-oxo-1,3-oxazolidin-5-yl]methyl}acetamide, or

EXAMPLE 560

N-[[(5S)-3-[2-(1,1-dimethylethyl)-1-formyl-2,3-dihydro-1H-indol-5-yl]-2-oxo-5-oxazolidinyl]methyl]ethanethioamide

EXAMPLE 561

N-{[(5S)-3-(1-Methyl-2,2-dioxo-2,3-dihydro-1H-2,1-benzisothiazol-5-yl)-2-oxo-1,3-oxazolidin-5-yl]methyl}acetamide

EXAMPLE 562

N-({(5S)-3-[1-(2-Fluoroethyl)-2,2-dioxo-2,3-dihydro-1H-2,1-benzisothiazol-5-yl]-2-oxo-1,3-oxazolidin-5-yl}methyl)acetamide

EXAMPLE 563

N-({(5S)-3-[1-(2-Nitriloethyl)-2,2-dioxo-2,3-dihydro-1H-2,1-benzisothiazol-5-yl]-2-oxo-1,3-oxazolidin-5-yl}methyl)acetamide

EXAMPLE 564

N-({(5S)-3-[1-(2-Methoxyethyl)-2,2-dioxo-2,3-dihydro-1H-2,1-benzisothiazol-5-yl]-2-oxo-1,3-oxazolidin-5-yl}methyl)acetamide, or

EXAMPLE 565

N-({(5S)-3-[1-(2-Fluoroethyl)-2,2-dioxo-2,3-dihydro-1H-2,1-benzisothiazol-5-yl]-2-oxo-1,3-oxazolidin-5-yl}methyl)ethanethioamide

EXAMPLE 566

(−)-N-[[(5S)-3-[2-formyl-1,2,3,4-tetrahydro-6-isoquinolinyl]-2-oxo-5-oxazolidinyl]methyl]acetamide

EXAMPLE 567

(−)-N-[[(5S)-3-[2-[(acetyloxy)acetyl]-1,2,3,4-tetrahydro-6-isoquinolinyl]-2-oxo-5-oxazolidinyl]methyl]acetamide

EXAMPLE 568

(−)-N-[[(5S)-3-[2-[(hydroxy)acetyl]-1,2,3,4-tetrahydro-6-isoquinolinyl]-2-oxo-5-oxazolidinyl]methyl]acetamide

EXAMPLE 569

(+)-N-[[(5S)-3-[2-formyl-1,2,3,4-tetrahydro-6-isoquinolinyl]-2-oxo-5-oxazolidinyl]methyl]ethanethioamide, or

EXAMPLE 570

(+)-N-[[(5S)-3-[2-[(hydroxy)acetyl]-1,2,3,4-tetrahydro-6-isoquinolinyl]-2-oxo-5-oxazolidinyl]methyl]ethanethioamide

EXAMPLE 571

(+)-N-[[(5S)-3-[2-formyl-1,2,3,4-tetrahydro-7-isoquinolinyl]-2-oxo-5-oxazolidinyl]methyl]ethanethioamide, or

EXAMPLE 572

(+)-N-[[(5S)-3-[2-[(hydroxy)acetyl]-1,2,3,4-tetrahydro-7-isoquinolinyl]-2-oxo-5-oxazolidinyl]methyl]ethanethioamide

EXAMPLE 573

(−)-N-[[(5S)-3-(3,4-dihydro-1H-2-benzopyran-6-yl)-2-oxo-5-oxazolidinyl]methyl]acetamide

EXAMPLE 574

(+)-N-[[(5S)-3-(3,4-dihydro-1H-2-benzopyran-6-yl)-2-oxo-5-oxazolidinyl]methyl]ethanethioamide

EXAMPLE 575

(−)-N-[[(5S)-3-(3,4-dihydro-1H-2-benzothiopyran-6-yl)-2-oxo-5-oxazolidinyl]methyl]acetamide

EXAMPLE 576

(+)-N-[[(5S)-3-(3,4-dihydro-1H-2-benzothiopyran-6-yl)-2-oxo-5-oxazolidinyl]methyl]ethanethioamide, or

EXAMPLE 577

(+)-N-[[(5S)-3-(3,4-dihydro-2,2-dioxido-1H-2-benzothiopyran-6-yl)-2-oxo-5-oxazolidinyl]methyl]ethanethioamide EXAMPLE 578
(+)-N-[[(5S)-3-(3,4-dihydro-1H-2-benzopyran-7-yl)-2-oxo-5-oxazolidinyl]methyl]ethanethioamide
EXAMPLE 579
(−)-N-[[(5S)-3-(3,4-dihydro-1H-2-benzothiopyran-7-yl)-2-oxo-5-oxazolidinyl]methyl]acetamide
EXAMPLE 580
(+)-N-[[(5S)-3-(3,4-dihydro-1H-2-benzothiopyran-7-yl)-2-oxo-5-oxazolidinyl]methyl]ethanethioamide
EXAMPLE 581
(+)-N-[[(5S)-3-(3,4-dihydro-2,2-dioxido-1H-2-benzothiopyran-7-yl)-2-oxo-5-oxazolidinyl]methyl]ethanethioamide, or
EXAMPLE 582
N-[[(5S)-3-(3,4-dihydro-2-oxido-1H-2-benzothiopyran-7-yl)-2-oxo-5-oxazolidinyl]methyl]acetamide,
EXAMPLE 583
N-{[(5S)-3-(3-formyl-1,2,4,5-tetrahydro-1H-3-benzazepin-7-yl)-2-oxo-1,3-oxazolidin-5-yl]methyl}acetamide
EXAMPLE 584
N-{[(5S)-3-(3-glycoloyl-1,2,4,5-tetrahydro-1H-3-benzazepin-7-yl)-2-oxo-1,3-oxazolidin-5-yl]methyl}acetamide
EXAMPLE 585
N-{[(5S)-3-(3-glycoloyl-1,2,4,5-tetrahydro-1H-3-benzazepin-7-yl)-2-oxo-1,3-oxazolidin-5-yl]methyl}ethanethioamide
EXAMPLE 586
N-{[(5S)-3-(3-acetyl-1,2,4,5-tetrahydro-1H-3-benzazepin-7-yl)-2-oxo-1,3-oxazolidin-5-yl]methyl}acetamide
EXAMPLE 587
N-{[(5S)-3-(3-benzoyl-1,2,4,5-tetrahydro-1H-3-benzazepin-7-yl)-2-oxo-1,3-oxazolidin-5-yl]methyl}acetamide
EXAMPLE 588
N-({(5S)-3-[3-(5-amino-1,3,4-thiadiazol-2-yl)-1,2,4,5-tetrahydro-1H-3-benzazepin-7-yl]-2-oxo-1,3-oxazolidin-5-yl}methyl)acetamide
EXAMPLE 589
N-({(5S)-3-[3-(methylsulfonyl)-1,2,4,5-tetrahydro-1H-3-benzazepin-7-yl]-2-oxo-1,3-oxazolidin-5-yl}methyl)acetamide
EXAMPLE 590
N-({(5S)-3-[3-(5-methylthio-1,3,4-thiadiazol-2-yl)-1,2,4,5-tetrahydro-1H-3-benzazepin-7-yl]-2-oxo-1,3-oxazolidin-5-yl}methyl)acetamide
EXAMPLE 591
N-({(5S)-3-[3-(5-methyl-1,3,4-thiadiazol-2-yl)-1,2,4,5-tetrahydro-1H-3-benzazepin-7-yl]-2-oxo-1,3-oxazolidin-5-yl}methyl)acetamide
EXAMPLE 592
N-[((5S)-3-{3-(phenyl)acetyl-1,2,4,5-tetrahydro-1H-3-benzazepin-7-yl}-2-oxo-1,3-oxazolidin-5-yl)methyl]acetamide
EXAMPLE 593
N-[((5S)-3-{3-[5-(formylamino)-1,3,4-thiadiazol-2-yl]-1,2,4,5-tetrahydro-1H-3-benzazepin-7-yl}-2-oxo-1,3-oxazolidin-5-yl)methyl]acetamide
EXAMPLE 594
N-[5-(7-{(5S)-5-[(acetylamino)methyl]-2-oxo-1,3-oxazolidin-3-yl}-1,2,4,5-tetrahydro-3H-3-benzazepin-3-yl)-1,3,4-thiadiazol-2-yl]-2-hydroxyacetamide
EXAMPLE 595
N-[((SS)-3-{3-[(4-iodophenyl)acetyl]-1,2,4,5-tetrahydro-1H-3-benzazepin-7-yl}-2-oxo-1,3-oxazolidin-5-yl)methyl]acetamide
EXAMPLE 596
N-[((5S)-3-{3-[(3-trifluoromethyl)phenyl)acetyl]-1,2,4,5-tetrahydro-1H-3-benzazepin-7-yl}-2-oxo-1,3-oxazolidin-5-yl)methyl]acetamide
EXAMPLE 597
N-[((5S)-3-{3-[(4-trifluoromethyl)phenyl)acetyl]-1,2,4,5-tetrahydro-1H-3-benzazepin-7-yl}-2-oxo-1,3-oxazolidin-5-yl)methyl]acetamide
EXAMPLE 598
N-({(5S)-2-oxo-3-[3-(5-oxopentanoyl)-1,2,4,5-tetrahydro-1H-3-benzazepin-7-yl]-1,3-oxazolidin-5-yl}methyl)acetamide
EXAMPLE 599
N-({(5S)-2-oxo-3-[3-(5-oxohexanoyl)-1,2,4,5-tetrahydro-1H-3-benzazepin-7-yl]-1,3-oxazolidin-5-yl}methyl)acetamide
EXAMPLE 600
N-[{(5S)-3-(2-formyl-1,3,4,5-tetrahydro-1H-2-benzazepin-7-yl)-2-oxo-1,3-oxazolidin-5-yl]methyl}acetamide
EXAMPLE 601
N-{[(5S)-3-(2-glycoloyl-1,3,4,5-tetrahydro-1H-3-benzazepin-7-yl)-2-oxo-1,3-oxazolidin-5-yl]methyl}acetamide
EXAMPLE 602
N-{[(5S)-3-(2-acetyl-1,3,4,5-tetrahydro-1H-2-benzazepin-7-yl)-2-oxo-1,3-oxazolidin-5-yl]methyl}acetamide
EXAMPLE 603
7-{(5S)-5-[(acetylamino)methyl]-2-oxo-1,3-oxazolidin-3-yl}-N-phenyl-1,3,4,5-tetrahydro-2H-2-benzazepine-2-carboxamide
EXAMPLE 604
N-{[(5S)-3-(1-formyl-2,3,4,5-tetrahydro-1H-1-benzazepin-7-yl)-2-oxo-1,3-oxazolidin-5-yl]methyl}acetamide
EXAMPLE 605
N-{[(SS)-3-(1-formyl-2,3,4,5-tetrahydro-1H-1-benzazepin-7-yl)-2-oxo-1,3-oxazolidin-5-yl]methyl}ethanethioamide
EXAMPLE 606
N-[[(5S)-2-oxo-3-(1,2,4,5-tetrahydro-3-benzothiepin-7-yl)-5-oxazolidinyl]methyl]acetamide
EXAMPLE 607
N-[[(5S)-2-oxo-3-(1,2,4,5-tetrahydro-3,3-dioxido-3-benzothiepin-7-yl)-5-oxazolidinyl]methyl]acetamide
EXAMPLE 608
N-[[(5S)-2-oxo-3-(1,2,4,5-tetrahydro-3-benzothiepin-7-yl)-5-oxazolidinyl]methyl]ethanethioamide
EXAMPLE 609
N-[[(5S)-2-oxo-3-(1,2,4,5-tetrahydro-3,3-dioxido-3-benzothiepin-7-yl)-5-oxazolidinyl]methyl]ethanethioamide
EXAMPLE 610
N-({(5S)-3-[3-fluoro-4-(1-imino-1-oxido-1$^{\lambda^4}$,4-thiazinan-4-yl)phenyl]-2-oxo-1,3-oxazolidin-5-yl}methyl)ethanethioamide
EXAMPLE 611
N-({(5S)-3-[3-fluoro-4-(1-imino-1-oxido-1$^{\lambda^4}$,4-thiazinan-4-yl)phenyl]-2-oxo-1,3-oxazolidin-5-yl}methyl)propanecarbothioamide

EXAMPLE 612

N-({(5S)-3-[3-fluoro-4-(1-imino-1-oxido-1$^{\lambda4}$,4-thiazinan-4-yl)phenyl]-2-oxo-1,3-oxazolidin-5-yl}methyl)cyclopropanecarbothioamide

EXAMPLE 613

N-({(5S)-3-[3-fluoro-4-(1-imino-1-oxidohexahydro-1$^{\lambda4}$-thiopyran-4-yl)phenyl]-2-oxo-1,3-oxazolidin-5-yl}methyl)acetamide (E)-isomer

EXAMPLE 614

N-({(5S)-3-[3-fluoro-4-(1-imino-1-oxidohexahydro-1$^{\lambda4}$-thiopyran-4-yl)phenyl]-2-oxo-1,3-oxazolidin-5-yl}methyl)ethanethioamide (E)-isomer

EXAMPLE 615

N-({(5S)-3-[3-fluoro-4-(1-imino-1-oxidohexahydro-1$^{\lambda4}$-thiopyran-4-yl)phenyl]-2-oxo-1,3-oxazolidin-5-yl}methyl)propanethioamide (E)-isomer

EXAMPLE 616

N-({(5S)-3-[3-fluoro-4-(1-imino-1-oxidohexahydro-1$^{\lambda4}$-thiopyran-4-yl)phenyl]-2-oxo-1,3-oxazolidin-5-yl}methyl)cyclopropanecarbothioamide (E)-isomer,

EXAMPLE 617

N-({(5S)-3-[3-fluoro-4-(1-imino-1-oxidohexahydro-1$^{\lambda4}$-thiopyran-4-yl)phenyl]-2-oxo-1,3-oxazolidin-5-yl}methyl)acetamide (Z)-isomer

EXAMPLE 618

N-({(5S)-3-[3-fluoro-4-(1-imino-1-oxidohexahydro-1$^{\lambda4}$-thiopyran-4-yl)phenyl]-2-oxo-1,3-oxazolidin-5-yl}methyl)ethanethioamide (Z)-isomer

EXAMPLE 619

N-({(5S)-3-[3-fluoro-4-(1-imino-1-oxidohexahydro-1$^{\lambda4}$-thiopyran-4-yl)phenyl]-2-oxo-1,3-oxazolidin-5-yl}methyl)propanethioamide (Z)-isomer

EXAMPLE 620

N-({(5S)-3-[3-fluoro-4-(1-imino-1-oxidohexahydro-1$^{\lambda4}$-thiopyran-4-yl)phenyl]-2-oxo-1,3-oxazolidin-5-yl}methyl)cyclopropanethioamide (Z)-isomer

EXAMPLE 621

N-({(5S)-3-[3-fluoro-4-[1-(acetylimino)-1-oxidohexahydro-1$^{\lambda4}$-thiopyran-4-yl]phenyl]-2-oxo-1,3-oxazolidin-5-yl}methyl)acetamide, Z-isomer

EXAMPLE 622

N-({(5S)-3-[3-fluoro-4-[1-(methylimino)-1-oxidohexahydro-1$^{\lambda4}$-thiopyran-4-yl]phenyl]-2-oxo-1,3-oxazolidin-5-yl}methyl)propanethioamide, Z-isomer

EXAMPLE 623

N-({(5S)-3-[3-fluoro-4-[1-(acetylimino)-1-oxidohexahydro-1$^{\lambda4}$-thiopyran-4-yl]phenyl]-2-oxo-1,3-oxazolidin-5-yl}methyl)propanethioamide, Z-isomer

EXAMPLE 624

N-({(5S)-3-[3-fluoro-4-[1-(ethylimino)-1-oxidohexahydro-1$^{\lambda4}$-thiopyran-4-yl]phenyl]-2-oxo-1,3-oxazolidin-5-yl}methyl)propanethioamide, Z-isomer,

EXAMPLE 625

N-({(5S)-3-[3-fluoro-4-[1-[(phenylmethyl)imino]-1-oxidohexahydro-1$^{\lambda4}$-thiopyran-4-yl]phenyl]-2-oxo-1,3-oxazolidin-5-yl}methyl)propanethioamide, Z-isomer

EXAMPLE 626

N-({(5S)-3-[3-fluoro-4-[1-[(3-phenylpropyl)imino]-1-oxidohexahydro-1$^{\lambda4}$-thiopyran-4-yl]phenyl]-2-oxo-1,3-oxazolidin-5-yl}methyl)propanethioamide, Z-isomer

EXAMPLE 627

N-({(5S)-3-[3-fluoro-4-(1-{[(methylamino)carbonyl]imino}-1-oxidohexahydro-1$^{\lambda4}$-thiopyran-4-yl)phenyl]-2-oxo-1,3-oxazolidin-5-yl}methyl)propanethioamide, Z-isomer

EXAMPLE 628

N-({(5S)-3-[3-fluoro-4-(1-[(methoxycarbonyl)imino]-1-oxidohexahydro-1$^{\lambda4}$-thiopyran-4-yl)phenyl]-2-oxo-1,3-oxazolidin-5-yl}methyl)propanethioamide, Z-isomer

EXAMPLE 629

N-({(5S)-3-[3-fluoro-4-(1-[[(ethoxycarbonyl)methyl]imino]-1-oxidohexahydro-1$^{\lambda4}$-thiopyran-4-yl)phenyl]-2-oxo-1,3-oxazolidin-5-yl}methyl)propanethioamide, Z-isomer

EXAMPLE 630

N-({(5S)-3-[3-fluoro-4-(1-{[[(4-nitrophenyl)amino]carbonyl]imino}-1-oxidohexahydro-1$^{\lambda4}$-thiopyran-4-yl)phenyl]-2-oxo-1,3-oxazolidin-5-yl}methyl)propanethioamide, Z-isomer

EXAMPLE 631

N-({(5S)-3-[3-fluoro-4-[1-[(aminocarbonyl)imino]-1-oxidohexahydro-1$^{\lambda4}$-thiopyran-4-yl]phenyl]-2-oxo-1,3-oxazolidin-5-yl}methyl)propanethioamide, Z-isomer

EXAMPLE 632

N-({(5S)-3-[3-fluoro-4-[1-[[(aminocarbonyl)methyl]imino]-1-oxidohexahydro-1$^{\lambda4}$-thiopyran-4-yl]phenyl]-2-oxo-1,3-oxazolidin-5-yl}methyl)propanethioamide, Z-isomer

EXAMPLE 633
N-({(5S)-3-[3-fluoro-4-[1-[(2-hydroxyethyl) imino]-1-oxidohexahydro-1$^{\lambda 4}$-thiopyran-4-yl]phenyl]-2-oxo-1,3-oxazolidin-5-yl}methyl)propanethioamide, Z-isomer

EXAMPLE 634
N-[((5S)-3-{3-fluoro-4-[1-(methylimino)-1-oxido-1$^{\lambda 4}$,4-thiazinan-4-yl]phenyl}-2-oxo-1,3-oxazolidin-5-yl)methyl]propanethioamide

EXAMPLE 635
N-[((5S)-3-{3-fluoro-4-[1-(methylimino)-1-oxido-1$^{\lambda 4}$,4-thiazinan-4-yl]phenyl}-2-oxo-1,3-oxazolidin-5-yl) methyl]cyclopropanecarbothioamide

EXAMPLE 636
N-[((5S)-3-{3-fluoro-4-(1-[(methoxycarbonyl) imino]-1-oxido-1$^{\lambda 4}$,4-thiazinan-4-yl)phenyl}-2-oxo-1,3-oxazolidin-5-yl)methyl]propanethioamide

EXAMPLE 637
N-[((5S)-3-{3-fluoro-4-(1-[(methoxycarbonyl) imino]-1-oxido-1$^{\lambda 4}$,4-thiazinan-4-yl)phenyl}-2-oxo-1,3-oxazolidin-5-yl)methyl]cyclopropanecarbothioamide

EXAMPLE 638
N-({(5S)-3-[3-fluoro-4-[1-(methylimino)-1-oxidohexahydro-1$^{\lambda 4}$-thiopyran-4-yl]phenyl]-2-oxo-1,3-oxazolidin-5-yl}methyl) cyclopropanecarbothioamide, Z-isomer

EXAMPLE 639
N-[((5S)-3-{3-fluoro-4-[1-[(methoxycarbonyl) imino]-1-oxidohexahydro-1-thiopyran-4-yl]phenyl}-2-oxo-1,3-oxazolidin-5-yl)methyl] cyclopropanecarbothioamide, Z-isomer

EXAMPLE 640
N-[((5S)-3-{3-fluoro-4-[1-(methylimino)-1-oxidohexahydro-1$^{\lambda 4}$-thiopyran-4-yl]phenyl}-2-oxo-1,3-oxazolidin-5-yl)methyl] cyclopropanecarbothioamide, E-isomer

EXAMPLE 641
N-[((5S)-3-{3-fluoro-4-[1-(methylimino)-1-oxidohexahydro-1$^{\lambda 4}$-thiopyran-4-yl]phenyl}-2-oxo-1,3-oxazolidin-5-yl)methyl]propanethioamide, E-isomer

EXAMPLE 642
N-[((5S)-3-{3-fluoro-4-[1-[[(phenylmethoxy) carbnonyl]imino]-1-oxidohexahydro-1$^{\lambda 4}$-thiopyran-4-yl]phenyl}-2-oxo-1,3-oxazolidin-5-yl)methyl] acetamide, Z-isomer

EXAMPLE 643
N-({(5S)-3-[3-Fluoro-4-(1-{[(benzylamino) carbonyl]imino}-1-oxidohexahydro-1$^{\lambda 4}$-thiopyran-4-yl)phenyl]-2-oxo-1,3-oxazolidin-5-yl}methyl) acetamide, Z-isomer

EXAMPLE 644
N-{[(5S)-3-(3-fluoro-4-{4-[2-(methylsulfinyl) acetyl]-1-piperazinyl}phenyl)-2-oxo-1,3-oxazolidin-5-yl]methyl}propanethioamide

EXAMPLE 645
N-{[(5S)-3-(3-fluoro-4-{4-[2-(methylsulfanyl) acetyl]-1-piperazinyl}phenyl)-2-oxo-1,3-oxazolidin-5-yl]methyl}propanethioamide

EXAMPLE 646
N-{[(5S)-3-(3-fluoro-4-{4-[2-(methylsulfonyl) acetyl]-1-piperazinyl}phenyl]-2-oxo-1,3-oxazolidin-5-yl]methyl}propanethioamide

EXAMPLE 647
N-({(5S)-3-[4-(4-ethanethioyl-1-piperazinyl)-3-fluorophenyl]-2-oxo-1,3-oxazolidin-5-yl}methyl) propanethioamide

EXAMPLE 648
N-({(5S)-3-[4-(4-cyano-1-piperazinyl)-3-fluorophenyl]-2-oxo-1,3-oxazolidin-5-yl}methyl) propanethioamide

EXAMPLE 649
N-({(5S)-3-(3-fluoro-4-{4-[2-(methylaminocarbonyloxy)acetyl]-1-piperazinyl}phenyl)-2-oxo-1,3-oxazolidin-5-yl}methyl)propanethioamide

EXAMPLE 650
N-({(5S)-3-(3-fluoro-4-{4-[2-[(2-methoxyethoxy) carbonyloxy]acetyl]-1-piperazinyl}phenyl)-2-oxo-1,3-oxazolidin-5-yl}methyl)propanethioamide

EXAMPLE 651
N-[((5S)-3-{3-fluoro-4-[4-((2S)-2-hydroxy-3-methoxypropanoyl)-1-piperazinyl]phenyl}-2-oxo-1,3-oxazolidin-5-yl)methyl]propanethioamide

EXAMPLE 652
N-[((5S)-3-{3-fluoro-4-[4-((2S)-2,3-dimethyoxypropanoyl)-1-piperazinyl]phenyl}-2-oxo-1,3-oxazolidin-5-yl)methyl]propanethioamide

EXAMPLE 653
N-[((5S)-3-{3-fluoro-4-[4-((2S)-3-hydroxy-2-methyoxypropanoyl)-1-piperazinyl]phenyl}-2-oxo-1,3-oxazolidin-5-yl)methyl]propanethioamide

EXAMPLE 654
N-({(5S)-3-[3-fluoro-4-(4-acetoacetyl-1-piperazinyl) phenyl]-2-oxo-1,3-oxazolidin-5-yl}methyl) propanethioamide

EXAMPLE 655
N-({(5S)-3-[3-fluoro-4-(4-pyruvoyl-1-piperazinyl) phenyl]-2-oxo-1,3-oxazolidin-5-yl}methyl) propanethioamide

EXAMPLE 656
N-({(5S)-3-[3-fluoro-4-[4-(3-hydroxypropanoyl)-1-piperazinyl]phenyl]-2-oxo-1,3-oxazolidin-5-yl}methyl]propanethioamide

EXAMPLE 657
N-{[(5S)-3-(3-fluoro-4-{4-[(1-hydroxycyclopropyl) carbonyl]-1-piperazinyl}phenyl)-2-oxo-1,3-oxazolidin-5-yl]methyl}propanethioamide

EXAMPLE 658
N-[((5S)-3-{3-fluoro-4-[4-(2-phenoxyacetyl)-1-piperazinyl]phenyl}-2-oxo-1,3-oxazolidin-5-yl) methyl]propanethioamide

145

EXAMPLE 659

N-({(5S)-3-[3-fluoro-4-[4-((2S)-2,3-dihydroxypropanoyl)-1-piperazinyl]phenyl]-2-oxo-1,3-oxazolidin-5-yl}methyl)propanethioamide

EXAMPLE 660

N-({(5S)-3-[3-fluoro-4-[4-((2R)-2,3-dihydroxypropanoyl)-1-piperazinyl]phenyl]-2-oxo-1,3-oxazolidin-5-yl}methyl)propanethioamide

EXAMPLE 661

N-{[(5S)-3-(3-fluoro-4-{4-[3-hydroxy-2-(hydroxymethyl)-2-methylpropanoyl]-1-piperazinyl}phenyl)-2-oxo-1,3-oxazolidin-5-yl]methyl}propanethioamide

EXAMPLE 662

N-[((5S)-3-{3-fluoro-4-[4-((2S)-2-hydroxy-3-phenylpropanoyl)-1-piperazinyl]phenyl}-2-oxo-1,3-oxazolidin-5-yl)methyl]propanethioamide

EXAMPLE 663

N-[((5S)-3-{3-fluoro-4-[4-((2R)-2-hydroxy-3-phenylpropanoyl)-1-piperazinyl]phenyl}-2-oxo-1,3-oxazolidin-5-yl) methyl]propanethioamide

EXAMPLE 664

N-[((5S)-3-{3-fluoro-4-[4-((2R)-2-hydroxy-2-phenylacetyl)-1-piperazinyl]phenyl}-2-oxo-1,3-oxazolidin-5-yl)methyl]propanethioamide

EXAMPLE 665

N-[((5S)-3-{3-fluoro-4-[4-((2S)-2-acetoxy-2-phenylacetyl)-1-piperazinyl]phenyl}-2-oxo-1,3-oxazolidin-5-yl)methyl]propanethioamide In order to more fully illustrate the nature of the invention and the manner of practicing the same, the following synthesis Example is presented.

SYNTHESIS EXAMPLE

2-{(3-[Acetyl({(5S)-3-[4-(1,1-dioxidotetrahydro-2H-thiopyran-4-yl)-3-fluorophenyl]-2-oxo-1,3-oxazolidin 5-yl}methyl)amino]-1,1-dimethyl-3-oxopropyl}-3,5-dimethylphenyl Dihydrogen Phosphate.

Step 1.

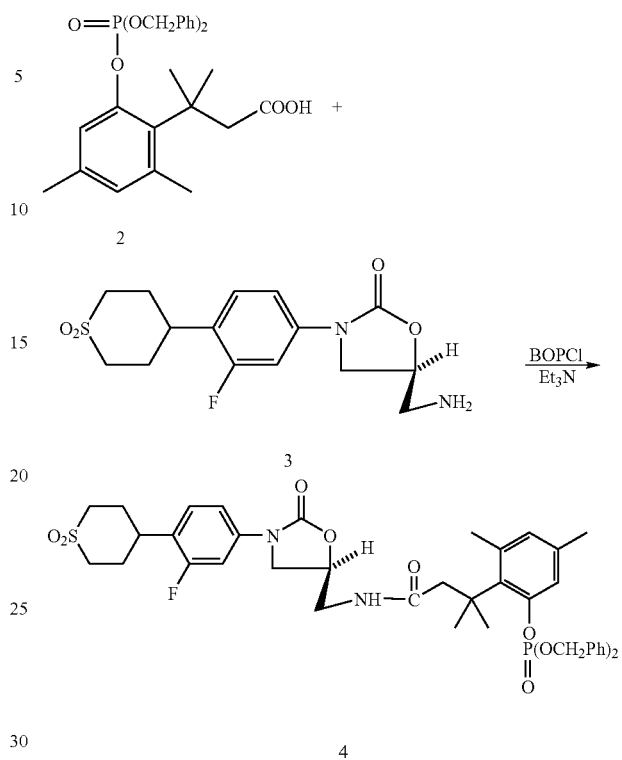

A stirred mixture of 2 (0.57 g, 1.18 mmol) (M. G. Nicolaou, C. -S. Yuan and R. T. Borchardt, *J. Org. Chem.* 1996, 61, 8636–8641), 3 (0.45 g, 1.19 mmol) (Case 6118.N CN1, Example 11, Step 1) and triethylamine (0.8 ml) in $CH_2Cl_2$ (60 ml), under nitrogen was cooled in an ice bath and treated with bis (2-oxo-3-oxazolidinyl)phosphinic chloride (0.456 g, 1.79 mmol). It was kept in the ice bath for 45 min and at ambient temperature (24° C.) for 2 h 15 min and then concentrated in vacuo. The residue was mixed with EtOAc and washed with 5% aqueous citric acid and brine, dried ($MgSO_4$) and concentrated. Chromatography of the residue on silica gel with 2.5% MeOH—$CH_2Cl_2$ gave 0.88 g of 4: $^1$H NMR (300 MHz, $CDCl_3$) δ 1.61, 1.65 (s, s, 6H), 2.08 (s, 3H), 2.15 (m, 2H), 2.37 (m, 2H), 2.48 (s, 3H), 2.56 (m, 2H), 3.13 (m, 6H), 3.35 (m, 3H), 4.28 (m, 1H), 5.12 (m, 4H), 6.66 (s, 1H), 6.98 (s, 1H), 7.13 (m, 3H), 7.36 (m, 11H); MS (ESI) m/z 807 (M+H$^+$), 829 (M+Na$^+$).

Step 2.

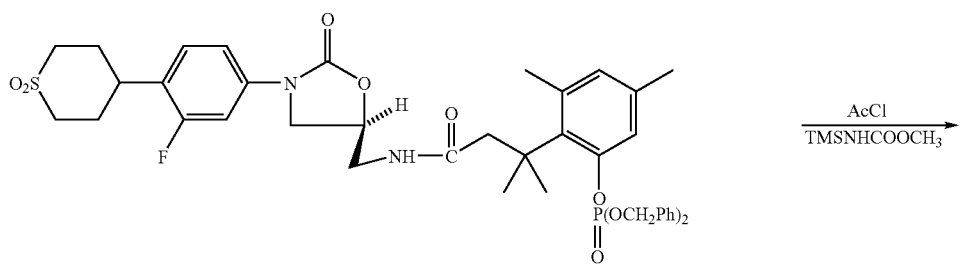

4

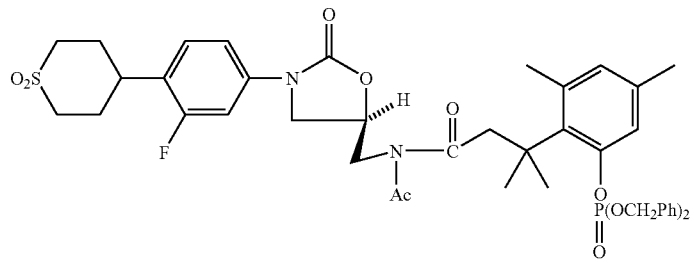

5

A stirred solution of 4 (0.85 g, 1.05 mmol) in methyl trimethylsilylcarbamate (3 ml), under nitrogen was treated, dropwise with acetyl chloride (0.25 ml, 3.5 mmol) and kept at ambient temperature (24° C.) for 3.5 h. It was then diluted with pentane to give a gum. The liquid was decanted and the residue was trituratred twice with pentane and once with Et$_2$O to give a semisolid material that was chromatographed on silica gel with 30% EtOAc —CH$_2$Cl$_2$. The product amounted to 0.62 g of 5: $^1$H NMR (300 MHz, CDCl$_3$) δ 1.55 (s, 3H), 1.62 (s, 3H), 2.16 (s, 3H), 2.20 (m, 1H), 2.23 (s, 3H), 2.42 (m, 2H), 2.57 (s, 3H), 3.17 (m, 5H), 3.52 (m, 5H), 3.87 (m, 2H), 4.61 (m, 1H), 5.05 (m, 4H), 6.79 (s, 1H), 6.98 (s, 1H), 7.11 (dd, 1H), 7.28 (m, 11H), 7.42 (dd, 1H); HRMS (FAB) calcd for C$_{44}$H$_{51}$FN$_2$O$_{10}$PS (M+H$^+$), 849.2986, found 849.2988.

Step 3.

A mixture of 5 (0.62 g), 10% palladium-on-carbon catalyst (0.16 g) and THF (20 ml) was hydrogenated at atmospheric pressure for 80 min, filtered through celite and concentrated in vacuo. The resulting foam was triturated with Et$_2$O to give 0.419 g of 1, a white powder: mp 116–124° C. (dec); MS (ESI) m/z 627 (M+H$^+$), 649 (M+Na$^+$); HRMS (FAB) calcd for C$_{28}$H$_{37}$FN$_2$O$_9$PS (M+H$^+$) 627.1941, found 627.1947.

Although the present invention has been exemplified using oxazolidinone compounds, it is understood that any amide-containing compound can be made more water-soluble using the present invention. Moreover, although the foregoing invention has been described in some detail by way of illustration and example for purposes of clarity and understanding, it would be apparent to those skilled in the art that certain changes and modifications could be made without departing from the scope and spirit of the present

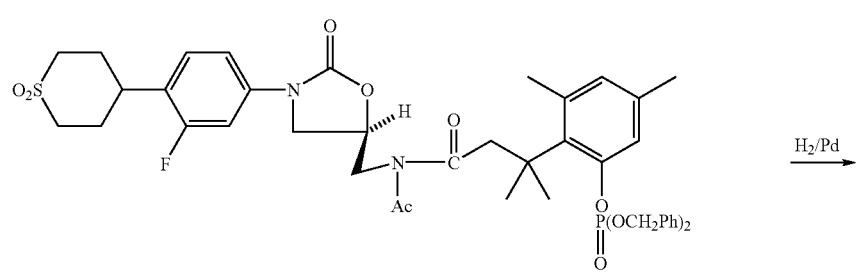

5

H$_2$/Pd →

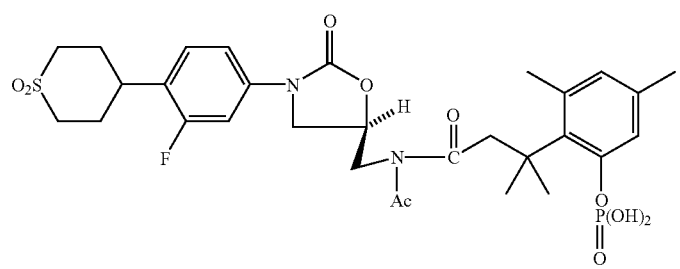

1

What is claimed is:

1. An oxazolidinone derivative of formula (I)

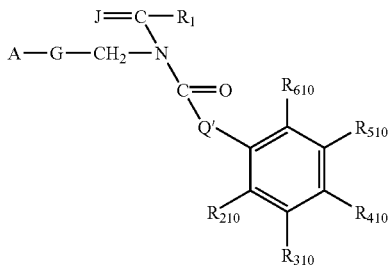

wherein J is O or S;

Q' is a) 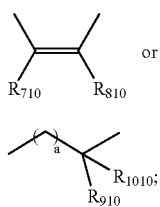 or b) 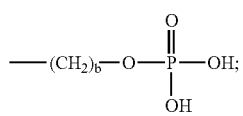

$R_{210}$ is a) 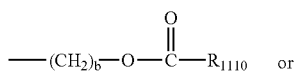 or b) —(CH$_2$)$_b$—O—P(O)(OH)—OH;

$R_{310}$, $R_{410}$ and $R_{510}$ each independently are
a) H,
b) $C_{1-4}$ alkyl,
c) halogen,
d) $C_{1-4}$ alkoxy,
e) hydroxy,
f) (CH$_2$)$_c$OP(O)(OH)$_2$,
g) $C_{1-4}$ acyloxy, or
h) $C_{1-4}$ alkyl substituted by halogen, hydroxy, acyloxy, NR$_{1210}$R$_{1310}$, or alkoxy;

$R_{610}$, $R_{710}$ and $R_{810}$ each independently are
a) H,
b) CH$_3$, or
c) C$_2$H$_5$;

$R_{910}$ and $R_{1010}$ each independently are
a) H,
b) CH$_3$,
c) C$_2$H$_5$, or
d) combine to form a $C_{3-5}$ cycloalkyl;

$R_{1110}$ is H or $C_{1-6}$ alkyl;

$R_{1210}$ and $R_{1310}$ each independently are
a) H,
b) $C_{1-4}$ alkyl, or
c) combine to form a heterocyclic ring;

wherein a is 0 or 1, b is 0 or 1, and c is 0 or 1, with the proviso that when Q' is

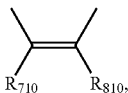

b is 0;

$R_1$ is
a) $C_{1-4}$ alkyl,
b) $C_{2-4}$ alkenyl,
c) OC$_{1-4}$ alkyl,
d) $C_{3-6}$ cycloalkyl,
e) $C_{1-4}$ alkyl substituted with one to three F, one to two Cl, CN, —COOC$_{1-4}$ alkyl or a $C_{3-6}$ cycloalkyl, or
f) H;

G is

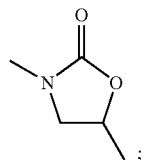

A is

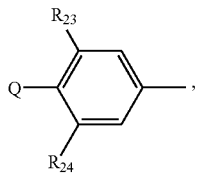

$R_{23}$ and $R_{24}$ are each independently
a) H,
b) F,
c) Cl,
d) $C_{1-2}$ alkyl,
e) CN,
f) OH,
g) $C_{1-2}$ alkoxy,
h) nitro, or
i) amino;

Q is

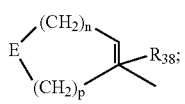

wherein " . . . " is a bond or absent;

E is
a) NR$_{39}$,
b) —S(=O)$_i$, or
a) O;

$R_{38}$ is
a) H,
c) —(CH$_2$)$_q$-aryl, or
d) F;

$R_{39}$ is
a) H,
b) $C_{1-6}$ alkyl optionally substituted with one or more OH, halo, or —CN,
c) —(CH$_2$)$_q$-aryl, d) —CO$_2$R$_{40}$,
e) —COR$_{41}$,
f) —C(=O)—(CH$_2$)$_q$—C(=O)R$_{40}$,
g) —S(=O)$_2$—C$_{1-6}$ alkyl, or
h) —S(=O)$_2$—(CH$_2$)$_q$-aryl;

R$_{40}$ is
  a) H,
  b) C$_{1-6}$ alkyl optionally substituted with one or more OH, halo, or —CN,
  c) —(CH$_2$)$_q$-aryl, or
  d) —(CH$_2$)$_q$—OR$_{42}$;

R$_{41}$ is
  a) C$_{1-6}$ alkyl optionally substituted with one or more OH, halo, or —CN,
  b) —(CH$_2$)$_q$-aryl, or
  c) —(CH$_2$)$_q$—OR$_{42}$;

R$_{42}$ is
  a) H,
  b) C$_{1-6}$ alkyl,
  c) —(CH$_2$)$_q$-aryl, or
  d) —C(=O)—C$_{1-6}$ alkyl;

aryl is
  a) phenyl, or
  b) pyridyl;

i is 0, 1, or 2;
n is 0, 1, 2, 3, 4, or 5;
p is 0, 1, 2, 3, 4, or 5; with the proviso that n and p together are 1, 2, 3, 4, or 5; and
q is 1, 2, 3, or 4.

2. The oxazolidinone derivative of claim 1 which is a compound of formula (VIII)

(VIII)

3. An oxazolidinone derivative of claim 2 wherein J is O.

4. An oxazolidinone derivative of claim 2 wherein A is wherein R$_{23}$ and R$_{24}$ are independently H or F;

wherein Q is and E is —S(=O)$_i$.

5. An oxazolidinone derivative of formula (XIII)

(XIII)

wherein J is O or S;

R$_1'$ is
  a) H,
  b) OH,
  c) C$_{1-4}$ alkyl,
  d) OC$_{1-4}$ alkyl,
  e) C$_{2-4}$ alkenyl,
  f) amino,
wherein c)–f) are optionally substituted with one to three F, one to two Cl, CN, —COOC$_{1-4}$ alkyl or a C$_{3-6}$ cycloalkyl Q' is a)

b)

Q' is a)
R$_{210}$ is a) (CH$_2$)$_b$—O—C—R$_{1110}$ or b) —(CH$_2$)$_b$—O—P(=O)(OH)—OH

R$_{310}$, R$_{410}$ and R$_{510}$ each independently are
  a) H,
  b) C$_{1-4}$ alkyl,
  c) halogen,
  d) C$_{1-4}$ alkoxy,
  e) hydroxy,
  f) (CH$_2$)$_c$OP(O)(OH)$_2$,
  g) C$_{1-4}$ acyloxy, or
  h) C$_{1-4}$ alkyl substituted by halogen, hydroxy, acyloxy, NR$_{1210}$R$_{1330}$, or alkoxy;

$R_{610}$, $R_{710}$ and $R_{810}$ each independently are
a) H,
b) $CH_3$, or
c) $C_2H_5$;

$R_{910}$ and $R_{1010}$ each independently are
a) H,
b) $CH_3$,
c) $C_2H_5$, or
d) combine to form a $C_{3-5}$ cycloalkyl;

$R_{1110}$ is H or $C_{1-6}$ alkyl;

$R_{1210}$ and $R_{1310}$ each independently are
a) H,
b) $C_{1-4}$ alkyl, or
c) combine to form a heterocyclic ring;

wherein a is 0 or 1, b is 0 or 1, and c is 0 or 1, with the proviso that when Q' is

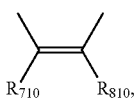

b is 0;

G is

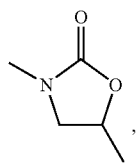

A is

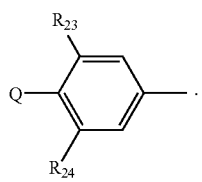

$R_{23}$ and $R_{24}$ are independently
a) H,
b) F,
c) Cl,
d) $C_{1-2}$ alkyl,
e) CN
f) OH,
g) $C_{1-2}$ alkoxy,
h) nitro, or
i) amino;

Q is

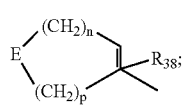

wherein " . . . " is a bond or absent;

E is
a) $NR_{39}$,
b) —S(=O)$_i$, or
c) O;

$R_{38}$ is
a) H,
b) $C_{1-6}$ alkyl,
c) —(CH$_2$)$_q$-aryl, or
d) F;

$R_{39}$ is
a) H,
b) $C_{1-6}$ alkyl optionally substituted with one or more OH, halo, or —CN,
c) —(CH$_2$)$_q$-aryl,
d) —CO$_2$R$_{40}$,
e) —COR$_{41}$,
f) —C(=O)—(CH$_2$)$_q$—C(=O)R$_{40}$,
g) —S(=O)$_2$—C$_{1-6}$ alkyl, or
h) —S(=O)$_2$—(CH$_2$)$_q$-aryl;

$R_{40}$ is
a) H,
b) $C_{1-6}$ alkyl optionally substituted with one or more OH, halo, or —CN,
c) —(CH$_2$)$_q$-aryl, or
d) —(CH$_2$)$_q$—OR$_{42}$;

$R_{41}$ is
a) $C_{1-6}$ alkyl optionally substituted with one or more OH, halo, or —CN,
b) —(CH$_2$)$_q$-aryl, or
c) —(CH$_2$)$_q$—OR$_{42}$;

$R_{42}$ is
a) H,
b) $C_{1-6}$ alkyl,
c) —(CH$_2$)$_q$-aryl, or
d) —C(=O)—C$_{1-6}$ alkyl;

aryl is
a) phenyl, or
b) pyridyl;

i is 0, 1, or 2;
n is 0, 1, 2, 3, 4, or 5;
p is 0, 1, 2, 3, 4, or 5; with the proviso that n and p together are 1, 2, 3, 4, or 5; and
q is 1, 2, 3, or 4.

6. The oxazolidinone derivative of claim 5, wherein J is O,
Q' is

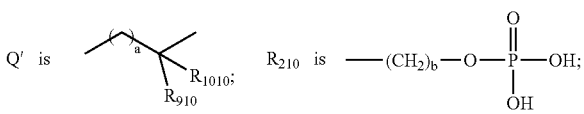

$R_{310}$ is H; $R_{410}$ is $CH_3$; $R_{510}$ is H; and $R_{610}$ is $CH_3$.

7. The oxazolidinone derivative of claim 2, wherein A is

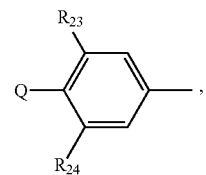

$R_{23}$ and $R_{24}$ are each independently H or F and Q is selected from the group consisting of

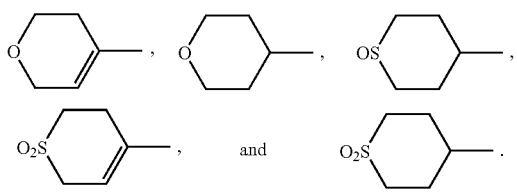

8. The oxazolidinone derivative of claim 6 wherein A is

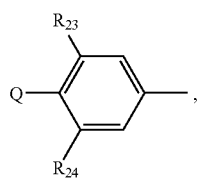

$R_{23}$ and $R_{24}$ are each independently H or F and Q is selected from the group consisting of

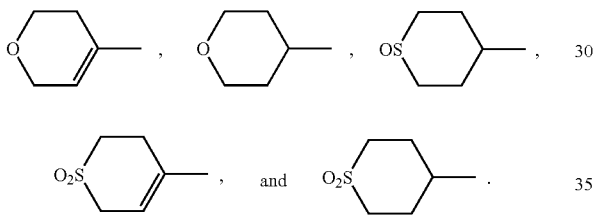

9. The oxazolidinone derivative of claim 1, wherein said derivative is 2-{3-[Acetyl({(5S)-3-[4-(1,1-dioxidotetrahydro-2H-thiopyran-4-yl)-3-fluorophenyl]-2-oxo-1,3-oxazolidin-5-yl}methyl)amino]-1,1-dimethyl-3-oxopropyl}-3,5-dimethylphenyldihydrogen phosphate.

10. A method of preparing an oxazolidinone derivative (VIII) having an improved water solubility comprising the steps of providing an amide of formula (III)

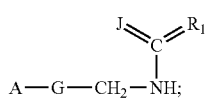

reacting the amide with a compound of formula (XIV)

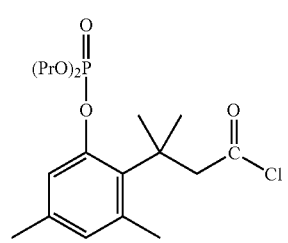

to form a compound of formula (XV)

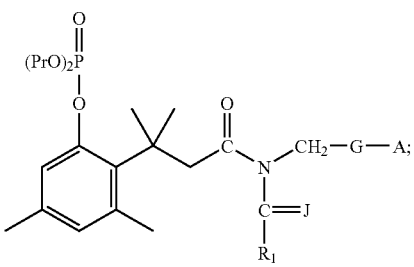

and removing the protecting groups to form a compound of formula (VIII)

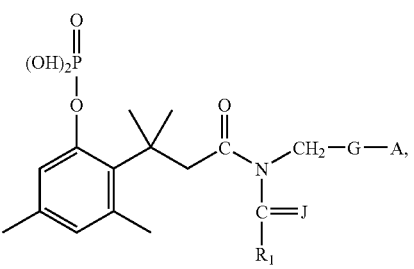

wherein J is O or S;
$R_1$ is
   a) $C_{1-4}$ alkyl,
   b) $C_{2-4}$ alkenyl,
   c) $OC_{1-4}$ alkyl,
   d) $C_{3-6}$ cycloalkyl,
   e) $C_{1-4}$ alkyl substituted with one to three F, one to two Cl, CN, —$COOC_{1-4}$ alkyl or a $C_{3-6}$ cycloalkyl; or
   f) H
Pr is a protecting group;
G is

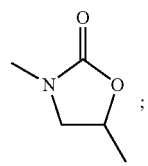

A is

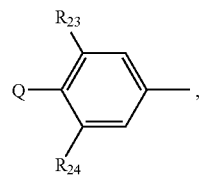

$R_{23}$ and $R_{24}$ are independently
   a) H,
   b) F,
   c) Cl,
   d) $C_{1-2}$ alkyl,
   e) CN f) OH,
g) $C_{1-2}$ alkoxy,
h) nitro, or
i) amino;

Q is

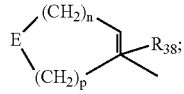

wherein " ... " is a bond or absent;
E is
  a) $NR_{39}$,
  b) —$S(=O)_i$, or
  c) O;
$R_{38}$ is
  a) H,
  b) $C_{1-6}$ alkyl,
  c) —$(CH_2)_q$-aryl, or
  d) F;
$R_{39}$ is
  a) H,
  b) $C_{1-6}$ alkyl optionally substituted with one or more OH, halo, or —CN,
  c) —$(CH_2)_q$-aryl,
  d) —$CO_2R_{40}$,
  e) —$COR_{41}$,
  f) —$C(=O)$—$(CH_2)_q$—$C(=O)R_{40}$,
  g) —$S(=O)_2$—$C_{1-6}$ alkyl, or
  h) —$S(=O)_2$—$(CH_2)_q$-aryl;
$R_{40}$ is
  a) H,
  b) $C_{1-6}$ alkyl optionally substituted with one or more OH, halo, or —CN,
  c) —$(CH_2)_q$-aryl, or
  d) —$(CH_2)_{q-OR42}$;
$R_{41}$ is
  a) $C_{1-6}$ alkyl optionally substituted with one or more OH, halo, or —CN,
  b) —$(CH_2)_q$-aryl, or
  c) —$(CH_2)_q$—$OR_{42}$;
$R_{42}$ is
  a) H,
  b) $C_{1-6}$ alkyl,
  c) —$(CH_2)_q$-alkyl, or
  d) —$C(=O)$—$C_{1-6}$ alkyl;
aryl is
  a) phenyl, or
  b) pyridyl;
i is 0, 1, or 2;
n is 0, 1, 2, 3, 4, or 5;
p is 0, 1, 2, 3, 4, or 5; with the proviso that n and p together are 1, 2, 3, 4, or 5; and
q is 1, 2, 3, or 4.

11. The method of claim 10, wherein the compound of formula (VIII) is 2-{3-[Acetyl({(5S)-3-[4-(1,1-dioxidotetrahydro-2H-thiopyran-4-yl)-3-fluorophenyl]-2-oxo-1,3-oxazolidin-5-yl}methyl)amino]-1,1-dimethyl-3-oxopropyl}-3,5-dimethylphenyldihydrogen phosphate.

12. A method of preparing an oxazolidinone derivative having an improved water solubility comprising the steps of providing an amide of formula (XVI)

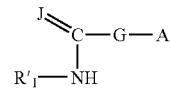

reacting the amide with a compound of formula (XIV)

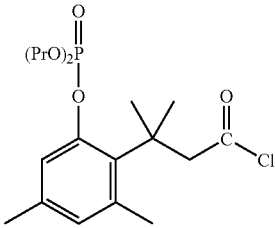

to form a compound of formula (XVII)

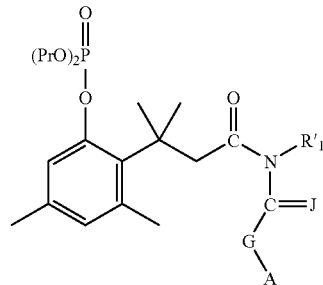

and removing the protecting groups to form a compound of formula (XVIII)

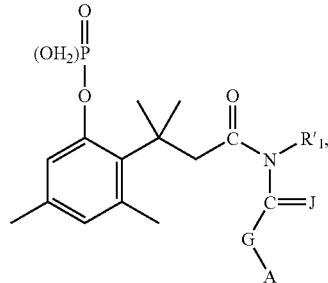

wherein J is O or S;
$R_1'$ is
  a) H,
  b) OH,
  c) $C_{1-4}$ alkyl,
  d) $OC_{1-4}$ alkyl,
  e) $C_{2-4}$ alkenyl,
  f) amino,
wherein c)–f) are optionally substituted with one to three F, one to two Cl, CN, —$COOC_{1-4}$ alkyl or a $C_{3-6}$ cycloalkyl;
Pr is a protecting group;

G is

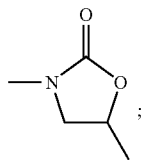;

A is

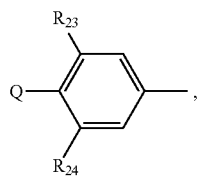, $R_{23}$ and $R_{24}$ are independently
   a) H,
   b) F,
   c) Cl,
   d) $C_{1-2}$ alkyl
   e) CN
   f) OH,
   g) $C_{1-2}$ alkoxy,
   h) nitro, or
   i) amino;
Q is

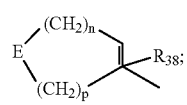

wherein " . . . " is a bond or absent;
E is
   a) $NR_{39}$,
   b) —$S(=O)_i$, or
   c) O;
$R_{38}$ is
   a) H,
   b) $Cl_{1-6}$ alkyl,
   c) —$(CH_2)_q$-aryl, or
   d) F;
$R_{39}$ is
   a) H,
   b) $_{1-6}$ alkyl optionally substituted with one or more OH, halo, or —CN,
   c) —$(CH_2)_q$-aryl
   d) —$CO_2R_{40}$,
   e) —$COR_{41}$,
   g) —$S(=O)_2$—$C_{1-6}$ alkyl, or
   h) —$S(=O)_2$—$(CH_2)_q$-aryl;
$R_{40}$ is
   a) H,
   b) $C_{1-6}$ alkyl optionally substituted with one or more OH, halo, or —CN,
   c) —$(CH_2)_q$-aryl, or
   d) —$(CH_2)_q$—$OR_{42}$;
$R_{41}$ is
   a) $C_{1-6}$ alkyl optionally substituted with one or more OH, halo, or —CN,
   b) —$(CH_2)_q$-aryl, or
   c) —$(CH_2)_q$—$OR_{42}$;
$R_{42}$ is
   a) H,
   b) $C_{1-6}$ alkyl,
   c) $(CH_2)_q$-aryl, or
   d) —$C(=O)$—$C_{1-6}$ alkyl;
aryl is
   a) phenyl, or
   b) pyridyl;
i is 0, 1, or 2;
n is 0, 1, 2, 3, 4, or 5;
p is 0, 1, 2, 3, 4, or 5; with the proviso that n and p together are 1, 2, 3, 4, or 5; and
q is 1, 2, 3, or 4.

13. The method of claim 10, wherein $R_{23}$ and $R_{24}$ are each independently H or F and Q is selected from the group consisting of

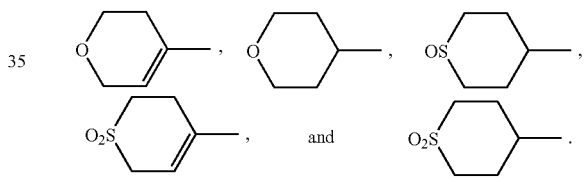

14. The method of claim 12 wherein $R_{23}$ and $R_{24}$ are each independently H or F and Q is selected from the group consisting of

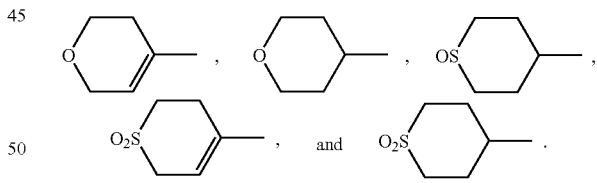

* * * * *